US012708458B2

(12) United States Patent
Johnson et al.

(10) Patent No.: US 12,708,458 B2
(45) Date of Patent: Aug. 18, 2026

(54) MULTI-PANEL GRAPHICAL USER INTERFACE FOR A ROBOTIC SURGICAL SYSTEM

(71) Applicant: Verb Surgical Inc., Santa Clara, CA (US)

(72) Inventors: Eric Mark Johnson, Pacific Grove, CA (US); Emma Essock-Burns, Mountain View, CA (US); Lawrence Edward Miller, Scotts Valley, CA (US); Francois W. Brahic, San Francisco, CA (US)

(73) Assignee: Auris Health, Inc., Santa Clara, CA (US)

(*) Notice: Subject to any disclaimer, the term of this patent is extended or adjusted under 35 U.S.C. 154(b) by 167 days.

(21) Appl. No.: 18/479,813

(22) Filed: Oct. 2, 2023

(65) Prior Publication Data

US 2024/0099790 A1 Mar. 28, 2024

Related U.S. Application Data

(63) Continuation of application No. 17/359,044, filed on Jun. 25, 2021, now Pat. No. 11,786,319, which is a (Continued)

(51) Int. Cl.
*A61B 34/00* (2016.01)
*A61B 1/00* (2006.01)
(Continued)

(52) U.S. Cl.
CPC ............ *A61B 34/25* (2016.02); *A61B 1/0005* (2013.01); *A61B 34/30* (2016.02); *A61B 34/74* (2016.02);
(Continued)

(58) Field of Classification Search
CPC ......... A61B 34/25; A61B 34/30; A61B 34/74; A61B 90/361; A61B 1/0005;
(Continued)

(56) References Cited

U.S. PATENT DOCUMENTS 6,847,336 B1 1/2005 Lemelson et al.
9,788,907 B1 10/2017 Alvi
(Continued)

FOREIGN PATENT DOCUMENTS

CN 101095635 A 1/2008
CN 101467894 A 7/2009
(Continued)

OTHER PUBLICATIONS

Examiner's Report dated May 18, 2021 issued by the Canadian Patent Office for Patent Application No. 3,079,816.
(Continued)

*Primary Examiner* — Andrew T Chiusano
(74) *Attorney, Agent, or Firm* — Aikin & Gallant, LLP

(57) ABSTRACT

A method for a robotic surgical system includes displaying a graphical user interface on a display to a user, wherein the graphical user interface includes a plurality of reconfigurable display panels, receiving a user input at one or more user input devices, wherein the user input indicates a selection of at least one software application relating to the robotic surgical system, and rendering content from the at least one selected software application among the plurality of reconfigurable display panels.

20 Claims, 37 Drawing Sheets

Related U.S. Application Data continuation of application No. 15/842,485, filed on Dec. 14, 2017, now Pat. No. 11,071,595.

(51) Int. Cl.

| | |
|---|---|
| ***A61B 17/00*** | (2006.01) |
| ***A61B 18/14*** | (2006.01) |
| ***A61B 34/10*** | (2016.01) |
| ***A61B 34/30*** | (2016.01) |
| ***A61B 34/35*** | (2016.01) |
| ***A61B 90/00*** | (2016.01) |
| ***B25J 9/16*** | (2006.01) |
| ***G06F 3/0482*** | (2013.01) |
| ***G06F 3/04845*** | (2022.01) |
| ***G09G 5/14*** | (2006.01) |

(52) U.S. Cl.

CPC ............. *A61B 90/361* (2016.02); *B25J 9/161* (2013.01); *B25J 9/1666* (2013.01); *B25J 9/1689* (2013.01); *G06F 3/0482* (2013.01); *G06F 3/04845* (2013.01); *G09G 5/14* (2013.01); *A61B 1/00045* (2013.01); *A61B 2017/00119* (2013.01); *A61B 2017/00128* (2013.01); *A61B 2017/00199* (2013.01); *A61B 2017/00203* (2013.01); *A61B 2017/00207* (2013.01); *A61B 2017/00212* (2013.01); *A61B 2017/00216* (2013.01); *A61B 2017/00221* (2013.01); *A61B 2017/00225* (2013.01); *A61B 18/1482* (2013.01); *A61B 2034/101* (2016.02); *A61B 2034/252* (2016.02); *A61B 2034/254* (2016.02); *A61B 2034/256* (2016.02); *A61B 2034/258* (2016.02); *A61B 2034/302* (2016.02); *A61B 34/35* (2016.02); *A61B 2034/741* (2016.02); *A61B 2034/743* (2016.02); *A61B 2034/744* (2016.02); *A61B 2090/065* (2016.02); *A61B 2090/365* (2016.02); *A61B 2090/372* (2016.02); *G05B 2219/45118* (2013.01); *G05B 2219/45119* (2013.01); *G09G 2340/045* (2013.01); *G09G 2340/0464* (2013.01); *G09G 2354/00* (2013.01); *G09G 2380/08* (2013.01); *Y10S 901/06* (2013.01); *Y10S 901/41* (2013.01)

(58) Field of Classification Search

CPC ........ A61B 2034/101; A61B 2034/252; A61B 2034/254; A61B 2034/256; A61B 2034/258; A61B 2034/302; A61B 34/35; A61B 2034/741; A61B 2034/743; A61B 2034/744; A61B 2090/065; A61B 2090/365; A61B 2090/372; A61B 1/00045; A61B 18/1482; A61B 2017/00119; A61B 2017/00128; A61B 2017/00199; A61B 2017/00203; A61B 2017/00207; A61B 2017/00212; A61B 2017/00216; A61B 2017/00221; A61B 2017/00225; B25J 9/161; B25J 9/1666; B25J 9/1689; G06F 3/0482; G06F 3/04845; G09G 5/14; G09G 2340/045; G09G 2340/0464; G09G 2354/00; G09G 2380/08; G05B 2219/45118; G05B 2219/45119; Y10S 901/06; Y10S 901/41

See application file for complete search history.

(56) References Cited

U.S. PATENT DOCUMENTS

| | | | | |
|---|---|---|---|---|
| 10,368,955 | B2 | 8/2019 | Cone et al. | |
| 10,661,453 | B2 | 5/2020 | Koenig et al. | |
| 10,786,327 | B2 | 9/2020 | Anderson et al. | |
| 2004/0243147 | A1 | 12/2004 | Lipow | |
| 2005/0043719 | A1 | 2/2005 | Sanchez et al. | |
| 2009/0036902 | A1 | 2/2009 | DiMaio et al. | |
| 2009/0192524 | A1 | 7/2009 | Itkowitz | |
| 2009/0221907 | A1 | 9/2009 | Bar-Tal | |
| 2009/0248036 | A1 | 10/2009 | Hoffman et al. | |
| 2009/0326556 | A1 | 12/2009 | Diolaiti | |
| 2010/0228249 | A1 | 9/2010 | Mohr et al. | |
| 2011/0187707 | A1 | 8/2011 | Kaufman | |
| 2012/0035764 | A1 | 2/2012 | Lipow et al. | |
| 2015/0317068 | A1 | 11/2015 | Marka | |
| 2016/0015471 | A1 | 1/2016 | Piron et al. | |
| 2016/0242858 | A1 | 8/2016 | Moctezuma de la Barrera | |
| 2016/0249992 | A1 | 9/2016 | Ruiz Morales et al. | |
| 2017/0337027 | A1 | 11/2017 | Chan | |
| 2018/0078034 | A1 | 3/2018 | Savall et al. | |
| 2018/0185113 | A1 | 7/2018 | Gregerson et al. | |
| 2019/0151032 | A1 | 5/2019 | Mustufa | |
| 2019/0231459 | A1* | 8/2019 | Mustufa | A61B 34/25 |
| 2019/0254759 | A1* | 8/2019 | Azizian | A61B 90/37 |
| 2019/0333626 | A1 | 10/2019 | Mansi | |
| 2020/0038125 | A1* | 2/2020 | Farlow | A61B 34/30 |
| 2020/0163731 | A1* | 5/2020 | Itkowitz | A61B 34/25 |
| 2020/0170731 | A1 | 6/2020 | Itkowitz | |
| 2020/0222138 | A1* | 7/2020 | Diolaiti | A61B 34/37 |
| 2020/0405420 | A1 | 12/2020 | Purohit | |
| 2022/0160445 | A1 | 5/2022 | Meglan | |

FOREIGN PATENT DOCUMENTS

| | | | |
|---|---|---|---|
| CN | 101530325 | A | 9/2009 |
| KR | 10-2012-0045734 | A | 5/2012 |
| WO | 2005/089065 | A2 | 9/2005 |
| WO | 2010120407 | A1 | 10/2010 |
| WO | 2014153396 | A1 | 9/2014 |

OTHER PUBLICATIONS

U.S. Appl. No. 62/432,528, filed Dec. 9, 2016.

Examination Report No. 1 of the Australian Patent Office dated Sep. 11, 2020 for related Australian Patent Application No. 2017442686.

Extended European Search Report and Search Opinion of the European Patent Office dated Sep. 15, 2020 for related European Patent Application No. 17934821.4.

MiRai, "ISBoxer—Window Layouts—The Wizard" Available Online at <https://www.youtube.com/watch?v=pA3MqP6LAAg>, Nov. 23, 2011, 1 page.

Notice of Acceptance of the Australian Patent Office dated Oct. 13, 2020 for related Australian Patent Application No. 2017442686.

International Preliminary Report on Patentability for International Application No. PCT/US2017/066489 mailed Jun. 25, 2020, 6 pages.

PCT Search Report and Written Opinion dated Feb. 21, 2018 for related PCT Application No. PCT/US2017/066489.

Advisory Action of the U.S. Patent Office dated May 8, 2020 for related U.S. Appl. No. 15/842,485.

Final Office Action of the U.S. Patent Office dated Feb. 19, 2020 for related U.S. Appl. No. 15/842,485.

Non-Final Office Action of the U.S. Patent Office dated Dec. 9, 2019 for related U.S. Appl. No. 15/842,485.

Non-Final Office Action of the U.S. Patent Office dated Nov. 4, 2020 for related U.S. Appl. No. 15/842,485.

Notice of Allowance of the U.S. Patent Office dated Feb. 24, 2021 for related U.S. Appl. No. 15/842,485.

Notice of Allowance of the U.S. Patent Office dated Jun. 28, 2021 for related U.S. Appl. No. 15/842,485.

Notice of Reasons for Rejection of the Korean Patent Office dated Jul. 26, 2021 for related Korean Patent Application No. 10-2020-7015478.

(56) References Cited

OTHER PUBLICATIONS

Non-Final Office Action of the U.S. Patent Office dated Dec. 21, 2021 for related U.S. Appl. No. 17/359,044.
First Office Action of the Chinese Patent Office dated Dec. 30, 2021 for related Chinese Patent Application No. 201780004289.6.
Office Action of the Canadian Patent Office dated Jan. 25, 2022 for related Canadian Patent Application No. 3079816.
Final Notice of Preliminary Rejection of the Korean Intellectual Property Office dated Jan. 27, 2022 for related Korean Patent Application No. 10-2020-7015478.
Final Office Action of the U.S. Patent Office dated Jul. 11, 2022 for related U.S. Appl. No. 17/359,044.
Notice of Final Rejection of the Korean Patent Office dated Jul. 19, 2022 for related Korean Patent Application No. 10-2020-7015478.
Office Action of the Canadian Patent Office dated May 18, 2021 for related Canadian Patent Application No. 3079816.
Office Action of the Korean Patent Office dated Sep. 20, 2022 for related Korean Patent Application No. 10-2020-7015478.
Second Office Action of the Chinese Patent Office dated Jun. 13, 2022 for related Chinese Patent Application No. 201780004289.6.
Notice of Allowance dated Oct. 14, 22 for Canadian Patent Application No. 3079816.
Non-Final Office Action of the U.S. Patent Office dated Nov. 25, 2022 for related U.S. Appl. No. 17/359,044.
Notification to Grant Patent Right for Invention of the Chinese Patent Office dated Sep. 15, 2022 for related Chinese Patent Application No. 201780004289.6.
Notice of Allowance of the U.S. Patent Office dated Jun. 7, 2023 for related U.S. Appl. No. 17/359,044.

* cited by examiner

| 410a | 400 | 410e |
| --- | --- | --- |
| 410b | | 410f |
| 410c | | 410g |
| 410d | | 410h |

FIG. 4A

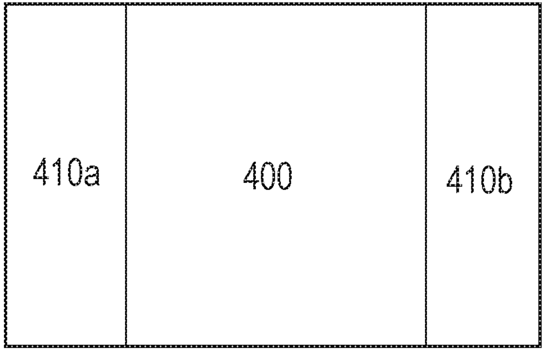
FIG. 4B
410a
400
410b
410c
410d
410e
FIG. 4C
410a
410b
FIG. 4D
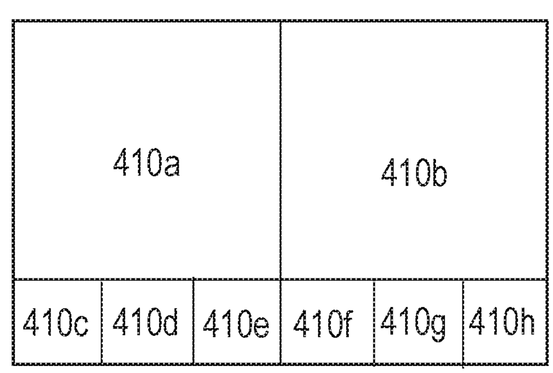
FIG. 4E

900

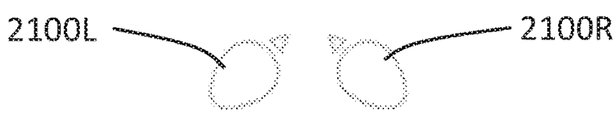

FIG. 21A

Overview of UID gestures used to control GUI.

Left UID

Right UID

Single left flick.
(Point UID to the left briefly and return to center.)

Single right flick.

Single down flick.

Single up flick.

Twist UID.
(Used to adjust items such as sliders.
Twist UID slightly in one direction to start sliding control.
Twisting further increases scroll speed.)

Use flicks to navigate.

Use flicks to navigate.
(Constrained horizontally.)

Use flicks to navigate.
(Constrained vertically.)

Single squeeze.
(Used to activate a selection.)

Double squeeze in rapid succession.
(Used to go back.)

Squeeze and hold for ~3 sec.
(Used to exit altogether.)

Squeeze and hold while rotating UID.
(Used to unlock GUI.)

FIG. 21B

MULTI-PANEL GRAPHICAL USER INTERFACE FOR A ROBOTIC SURGICAL SYSTEM

CROSS-REFERENCE TO RELATED APPLICATIONS

This application is a continuation of U.S. patent application Ser. No. 17/359,044, filed Jun. 25, 2021, which is a continuation of U.S. patent application Ser. No. 15/842,485, filed Dec. 14, 2017, now U.S. Pat. No. 11,071,595, issued Jul. 27, 2021, which are hereby incorporated by reference in their entirety.

TECHNICAL FIELD

This invention relates generally to the field of robotic surgery and more specifically to graphical user interfaces (GUIs) for a robotic surgical system.

BACKGROUND

Minimally-invasive surgery (MIS), such as laparoscopic surgery, involves techniques intended to reduce tissue damage during a surgical procedure. For example, laparoscopic procedures typically involve creating a number of small incisions in the patient (e.g., in the abdomen), and introducing one or more surgical instruments (e.g., an end effector, at least one camera, etc.) through the incisions into the patient. The surgical procedures may then be performed using the introduced surgical instruments, with the visualization aid provided by the camera.

Generally, MIS provides multiple benefits, such as reduced patient scarring, less patient pain, shorter patient recovery periods, and lower medical treatment costs associated with patient recovery. In some embodiments, MIS may be performed with robotic systems that include one or more robotic arms for manipulating surgical instruments based on commands from an operator. A robotic arm may, for example, support at its distal end various devices such as surgical end effectors, imaging devices, cannulae for providing access to the patient's body cavity and organs, etc.

In some embodiments, the operator may provide commands for manipulating surgical instruments while viewing an image that is provided by a camera and displayed on a display to the user. However, conventional display systems fall short in enabling effective operation of robotic surgical systems, which may, for example, involve oversight and coordination of a large amount of information. Thus, there is a need for graphical user interfaces for robotic surgical systems.

SUMMARY

Generally, a method for a robotic surgical system may include displaying a graphical user interface on a display to a user, wherein the graphical user interface includes a plurality of reconfigurable display panels, receiving a user input at one or more user input devices, wherein the user input indicates a selection of at least one software application relating to the robotic surgical system, and rendering content from the at least one selected software application among the plurality of reconfigurable display panels. An endoscopic image of a surgical site may additionally or alternatively be displayed on the display. In some variations, the method may further include reconfiguring a layout of at least a portion of the display panels. For example, at least one display panel may be repositioned and/or resized. As another example, content from a second selected software application may be rendered in the at least one display panel. Furthermore, in some variations, the method may include mirroring at least some of the rendered content onto a second display.

In some variations, the method may include reconfiguring a layout of at least a portion of the display panels in response to a second user input indicating a user-preferred layout, such as a second user input selecting a particular template layout or "clicking and dragging" panels and/or software application icons into a desired layout. Additionally or alternatively, the method may include detecting a surgical task in progress performed with the robotic surgical system, where reconfiguring at least a portion of the display panels may be performed automatically in response to the detected surgical task in progress.

The one or more user input devices for providing user input may, in some variations, include a handheld user input device configured to remotely control a robotic surgical instrument in the robotic surgical system. The handheld user interface may be further configured to selectively control the graphical user interface, such as by toggling between controlling the robotic surgical instrument and controlling the graphical user interface.

Furthermore, generally, a robotic surgical system may include a robotic surgical instrument, one or more handheld user input devices configured to remotely control the robotic surgical instrument, and a display configured to display a graphical user interface including a plurality of reconfigurable display panels. The one or more handheld user input devices may be further configured to selectively control receive a user input indicating a selection of at least one software application relating to the robotic surgical system. In this and in other suitable manners, the one or more handheld user input devices may be configured to selectively control the graphical user interface. The display may be configured to render content from the at least one selected software application among the plurality of reconfigurable display panels, and/or at least one endoscopic image of a surgical site. In some variations, at least some of the rendered content may be mirrored on a second display.

In some variations, the plurality of reconfigurable display panels may be reconfigurable in layout. For example, at least one of the display panels may be reconfigured by repositioning and/or resizing. Additionally or alternatively, at least one of the display panels may be reconfigured to render content from a second selected software application. In some variations, at least one of the display panels may be reconfigurable in response to a second user input indicating a user-preferred layout, and/or may be reconfigurable in response to a detected surgical task in progress.

BRIEF DESCRIPTION OF THE DRAWINGS

FIGS. 4A-4E are exemplary layouts for a multi-panel display for a GUI in a robotic surgical system.

FIG. 21A is a schematic illustration of an exemplary variation of cursors for navigating a GUI. FIG. 21B is a chart of exemplary correlations between operations of a handheld user input device and actions usable for control of a GUI.

DETAILED DESCRIPTION

Non-limiting examples of various aspects and variations of the invention are described herein and illustrated in the accompanying drawings.

Robotic Surgical System Overview

Figure 1A:
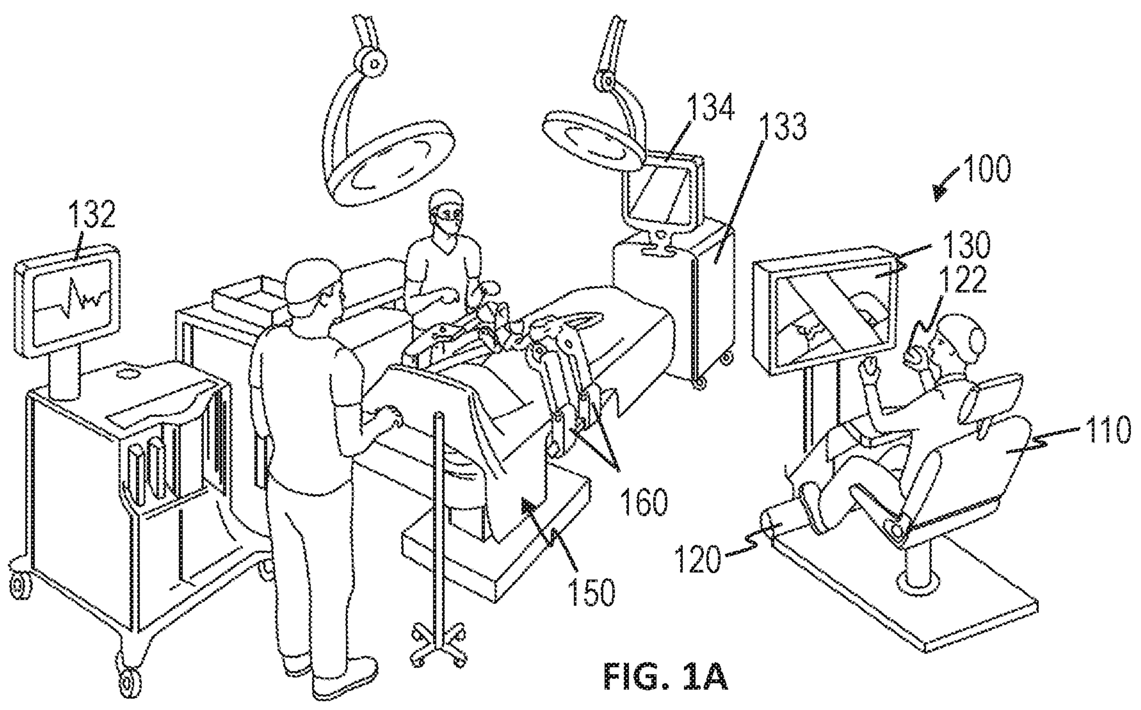
FIG. 1A depicts an example of an operating room arrangement with a robotic surgical system and a user console.

FIG. 1A is an illustration of an exemplary operating room environment with a robotic surgical system. Generally, as shown in FIG. 1A, the robotic surgical system includes a user console 100, a control tower 133, and one or more robotic arms 160 located at a robotic platform (e.g., table, bed, etc.), where surgical instruments (e.g., with end effectors) are attached to the distal ends of the robotic arms 160 for executing a surgical procedure. The robotic arms 160 are shown as a table-mounted system, but in other configurations, one or more robotic arms may be mounted to a cart, ceiling or sidewall, or other suitable support surface.

Figure 1B:
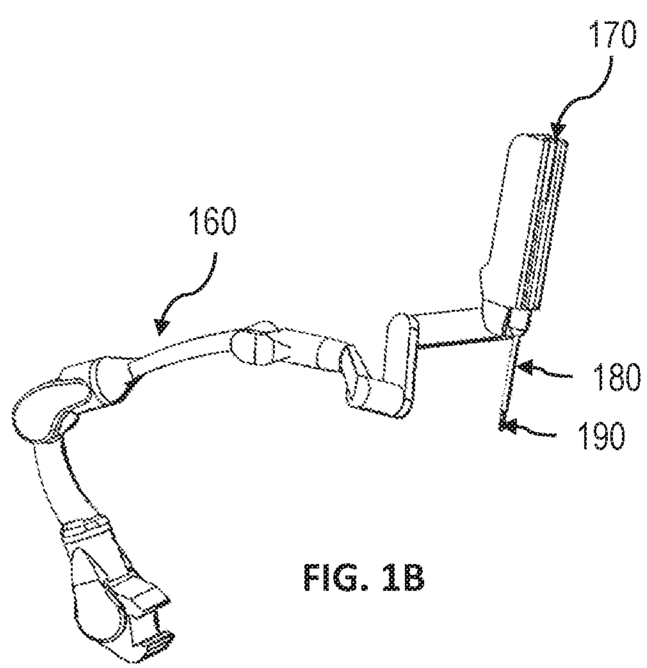
FIG. 1B is a schematic illustration of one exemplary variation of a robotic arm manipulator, tool driver, and cannula with a surgical tool.

As further illustration, as shown in the exemplary schematic of FIG. 1B, a robotic surgical system may include at least one robotic arm 160, and a tool driver 170 generally attached to a distal end of the robotic arm 160. A cannula 180 coupled to the end of the tool driver 170 may receive and guide a surgical instrument 190 (e.g., end effector, camera, etc.). Furthermore, the robotic arm 160 may include a plurality of links that are actuated so as to position and orient the tool driver 170, which actuates the surgical instrument 190. Exemplary variations of a robotic arm in a robotic surgical system are described in further detail in U.S. patent application Ser. No. 15/706,536 titled "ROBOTIC ARMS" and filed Sep. 15, 2017, which is incorporated herein in its entirety by this reference.

Generally, as shown in FIG. 1A, the user console 100 may be used to interface with the robotic surgical system 150. A user (such as a surgeon or other operator) may use the user console 100 to remotely manipulate the robotic arms 160 and/or surgical instruments (e.g., in tele-operation). The user console 100 may be located in the same operating room as the robotic system 150, as shown in FIG. 1A. In other embodiments, the user console 100 may be located in an adjacent or nearby room, or tele-operated from a remote location in a different building, city, or country. In one example, the user console 100 may comprise a seat 110, foot-operated controls 120, one or more handheld user input devices 122, and at least one user display 130 configured to display, for example, a view of the surgical site inside a patient (e.g., captured with an endoscopic camera), and/or other surgical or medical information. Exemplary variations of a user console are described in further detail in U.S. patent application Ser. No. 15/712,052 titled "USER CONSOLE SYSTEM FOR ROBOTIC SURGERY" filed on Sep. 21, 2017, which is incorporated herein in its entirety by this reference.

Figure 1C:
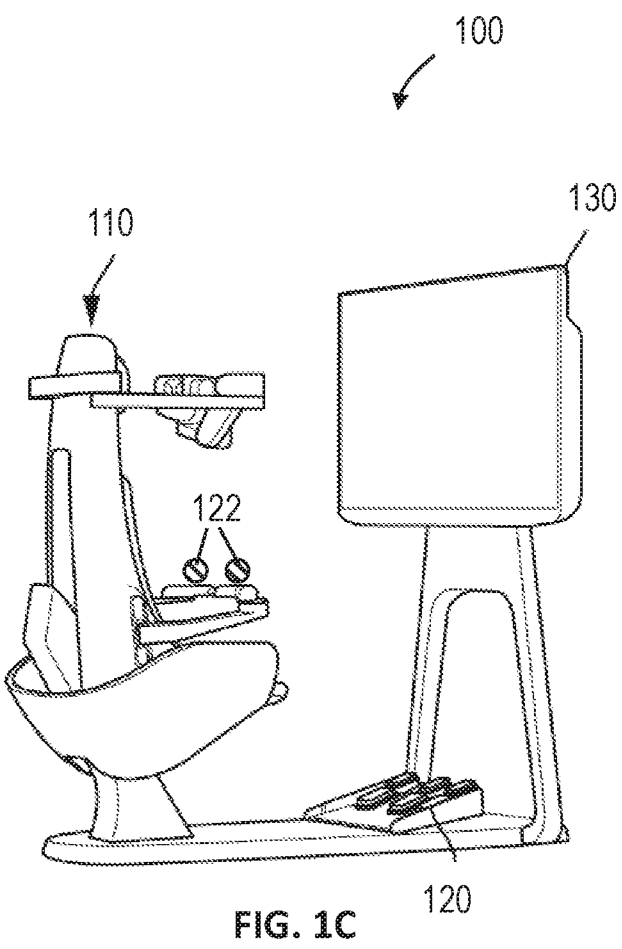
FIG. 1C is a schematic illustration of an exemplary user console.

For example, in the exemplary user console shown in FIG. 1C, a user located in the seat 110 and viewing the user display 130 may manipulate the foot-operated controls 120 and/or handheld user input devices 122 to remotely control the robotic arms 160 and/or surgical instruments mounted to the distal ends of the arm. The foot-operated controls 120 and/or handheld user input devices 122 may additionally or alternatively be used to control other aspects of the user console 100 or robotic system 150. For example, in variations in which the user generally controls (at any given time) a designated "left-hand" robotic arm/instrument and a designated "right-hand" robotic arm/instrument, the foot-operated controls 120 may enable a user to designate from among a larger group of available robotic arms/instruments which robotic arms/instruments comprise the "left-hand" and "right-hand" robotic arm/instruments (e.g., via toggle or rotation in selection among the available robotic arms/instruments). Other examples include adjusting or configuring the seat 110, the foot-operated controls 120, the user input devices 122, and/or the user display 130. Further exemplary variations of the foot-operated controls 120 are described herein.

In some variations, a user may operate the surgical robotic system in an "over the bed" (OTB) mode, in which the user is at the patient's side and simultaneously manipulating a robotically-driven instrument/end effector attached thereto (e.g., with a handheld user input device 122 held in one hand) and a manual laparoscopic tool. For example, the user's left hand may be manipulating a handheld user input device 122 to control a robotic surgical component, while the user's right hand may be manipulating a manual laparoscopic tool. Accordingly, in these variations, the user may perform both robotic-assisted MIS and manual laparoscopic surgery on a patient.

During an exemplary procedure or surgery, the patient is prepped and draped in a sterile fashion, and anesthesia may be achieved. Initial access to the surgical site may be performed manually with the robotic system 150 in a stowed configuration or withdrawn configuration to facilitate access to the surgical site. Once access is completed, initial positioning and/or preparation of the robotic system may be performed. During the surgical procedure, a surgeon or other user in the user console 100 may utilize the foot-operated controls 120, user input devices 122, and/or other suitable controls to manipulate various end effectors and/or imaging systems to perform the procedure. Manual assistance may be provided at the procedure table by other personnel, who may perform tasks including but not limited to retracting tissues, or performing manual repositioning or tool exchange involving one or more robotic arms 160. Other personnel may be present to assist the user at the user console 100. Medical and surgery-related information to aid other medical personnel (e.g., nurses) may be provided on additional displays such as a display 134 on a control tower 133 (e.g., control system for the robotic surgical system) and/or a display 132 located bedside proximate the patient. For example, as described in further detail herein, some or all information displayed to the user in the user console 100 may also be displayed on at least one additional display for other personnel and/or provide additional pathways for inter-personnel communication. When the procedure or surgery is completed, the robotic system 150 and/or user console 100 may be configured or set in a state to facilitate one or more post-operative procedures, including but not limited to robotic system 150 cleaning and/or sterilization, and/or healthcare record entry or printout, whether electronic or hard copy, such as via the user console 100.

In some variations, the communication between the robotic system 150, the user console 100, and any other displays may be through the control tower 133, which may translate user commands from the user console 100 to robotic control commands and transmit them to the robotic system 150. The control tower 133 may transmit status and feedback from the robotic system 150 back to the user console 100 (and/or other displays). The connections between the robotic system 150, the user console 100, other displays, and the control tower 133 may be via wired and/or wireless connections, and may be proprietary or performed using any of a variety of data communication protocols. Any wired connections may be built into the floor and/or walls or ceiling of the operating room. The robotic surgical system may provide video output to one or more displays, including displays within the operating room as well as remote displays accessible via the Internet or other networks. The video output or feed may be encrypted to ensure privacy, and all or one or more portions of the video output may be saved to a server, an electronic healthcare record system, or other suitable storage medium.

In some variations, additional user consoles 100 may be provided, for example to control additional surgical instruments, and/or to take control of one or more surgical instruments at a primary user console. This will permit, for example, a surgeon to take over or illustrate a technique during a surgical procedure with medical students and physicians-in-training, or to assist during complex surgeries requiring multiple surgeons acting simultaneously or in a coordinated manner.

Figure 2:
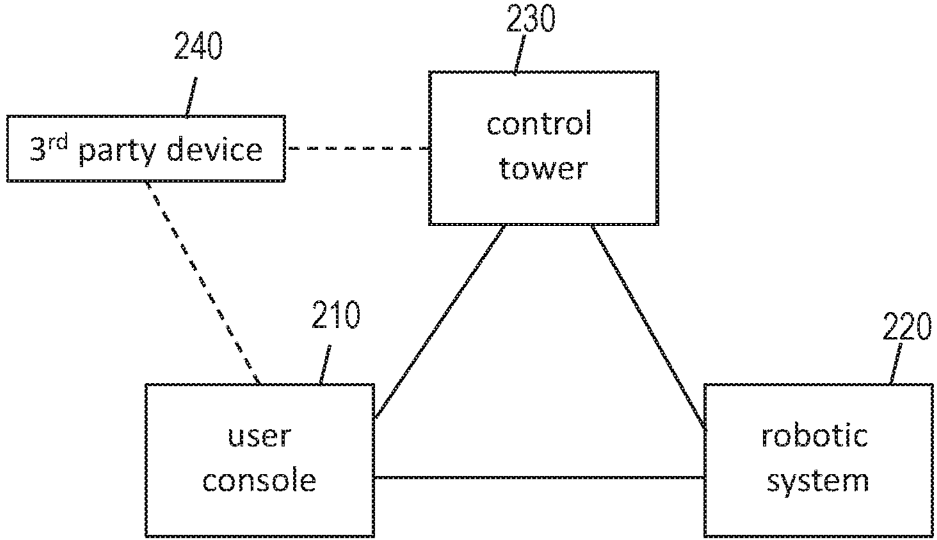
FIG. 2. is a schematic illustration of an exemplary variation of a user console for a robotic surgical system in communication with one or more third party devices.

In some variations, as shown in the schematic illustration of FIG. 2, one or more third party devices 240 may be configured to communicate with the user console 210 and/or other suitable portions of the robotic surgical system. For example, as described elsewhere herein, a surgeon or other user may sit in the user console 210, which may communicate with the control tower 230 and/or robotic instruments in a robotic system 220. Medical data (e.g., endoscopic images, patient vitals, tool status, etc.) may be displayed at the user console 210, the control tower 230, and/or other displays. At least a subset of the surgical and other medical-related information may furthermore be displayed at a third party device 240, such as a remote computer display that is viewed by a surgical collaborator in the same room or outside the room. Other communication, such as teleconferencing with audio and/or visual communication, may further be provided to and from the third party device. The surgical collaborator may be, for example, a supervisor or trainer, a medical colleague (e.g., radiologist), or other third party who may, for example, view and communicate via the third party device 240 to assist with the surgical procedure.

Figure 3:
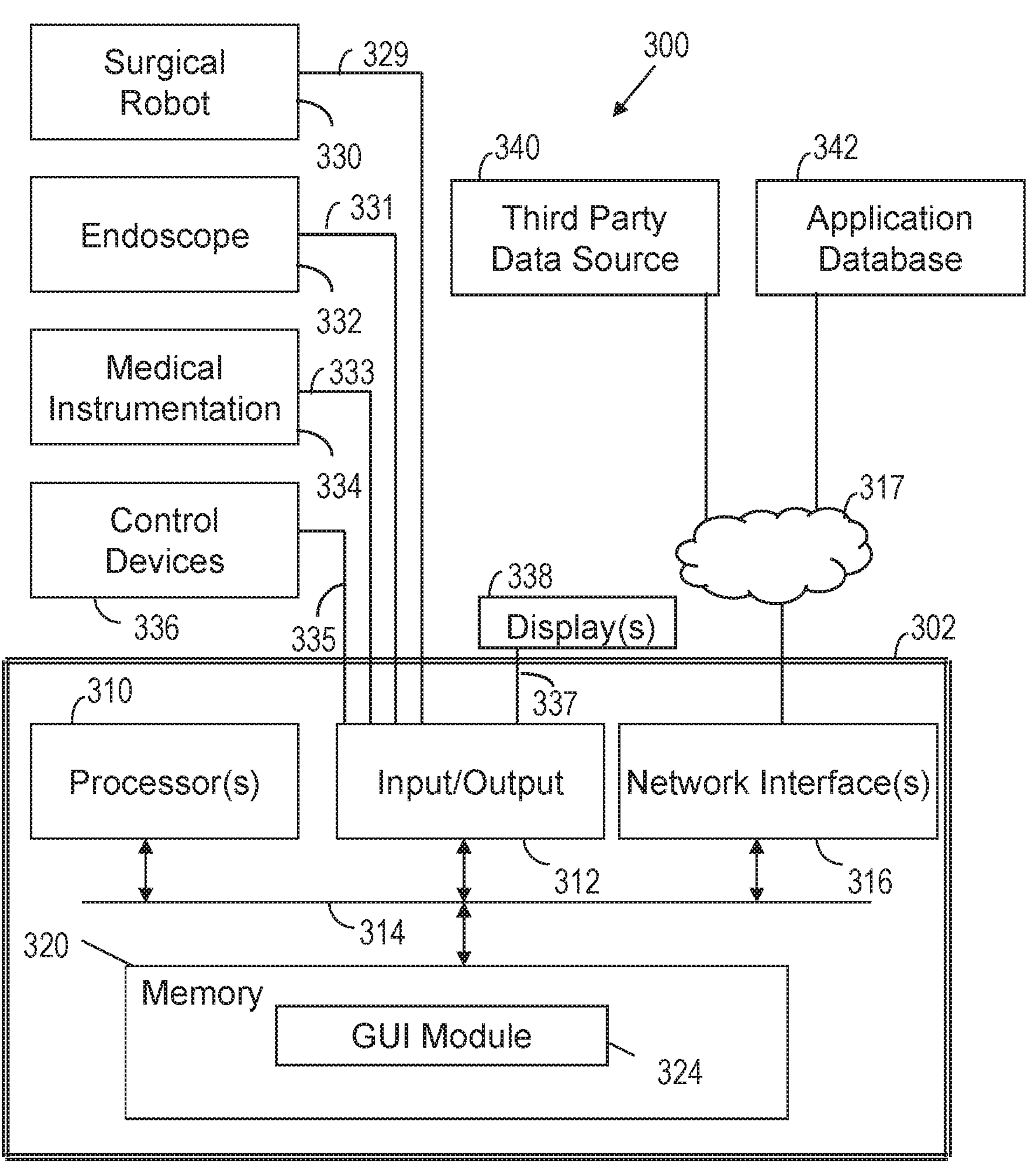
FIG. 3 is a schematic of a surgical robotic platform with a GUI module, where the surgical robotic platform is in communication with multiple medical data resources.

FIG. 3 is a schematic illustration of an exemplary variation of a system 300 including a robotic surgical system and its interaction with other devices and parties. Although a particular architecture of the various connected and communicating systems is depicted in FIG. 3, it should be understood that in other variations, other suitable architectures may be used and the arrangement shown in FIG. 3 is for illustrative purposes. The system 300 may include a surgical robotic platform 302 that facilitates the integration of medical data from discrete medical data resources generated from a variety of parties. Data from the discrete medical data resources may, for example, be used to form temporally coordinated medical data. Multi-panel displays of the temporally coordinated medical data may be configured and presented, as described further herein.

The platform 302 may be, for example, a machine with one or more processors 310 connected to one or more input/output devices 312 via a bus 314. The at least one processor may, for example, include a central processing unit, a graphics processing unit, an application specific integrated circuit, a field programmable logic device or combinations thereof.

The surgical robotic platform 302 may include one or more input ports to receive medical data from discrete medical data resources. For example, a surgical robot port 329 may receive surgical robot data from a surgical robot 330. Such data may, for example, include position data or other suitable status information. An imaging port 331 may receive imaging data from an imaging device 332, such as an endoscope, that is configured to capture images (e.g., still images, video images) of a surgical site. The endoscope may, for example, be inserted through a natural orifice or through an aperture in a surgical patient. As another example, one or more medical instrumentation ports 333 may receive patient vital information from medical instrumentation 334 (e.g., a pulse oximeter, electrocardiogram device, ultrasound device and/or the like). Additionally, as another example, one or more user control data ports 335 may receive user interaction data from one or more control devices that receive user inputs from a user for controlling the system. For example, one or more handheld user input devices, one or more foot pedals, and/or other suitable devices (e.g., eye tracking, head tracking sensors) may receive user inputs.

The surgical robotic platform 302 may further include one or more output ports 337 configured for connection to one or more displays 338. For example, the displays 338 may include an open display (e.g., monitor screen) in a user console, an immersive display or head-mounted device with a display, on supplemental displays such as on a control tower display (e.g., team display), a bedside display (e.g., nurse display), an overhead "stadium"-style screen, etc. For example, the multi-panel configurations disclosed herein may be presented on one or more displays 338. The one or more displays 338 may present three-dimensional images. In some variations, the one or more displays 338 may include a touchscreen. The one or more displays 138 may be a single display with multiple panels, with each panel presenting different content. Alternatively, the one or more displays 138 may include a collection of individual displays, where each individual display presents at least one panel.

In some variations, a network interface 316 may also be connected to the bus 314. The network interface 316 may, for example, provide connectivity to a network 317, which may be any combination of one or more wired and/or wireless networks. The network 317 may, for example, help enable communication between the surgical robotic platform 302 and other data sources or other devices. For example, one or more third party data sources 340 may also be connected to the network 317. The third party source 340 may include a third party device (e.g., another computer operated by a third party such as another doctor or medical specialist), a repository of video surgical procedure data (e.g., which may be relevant to a procedure being performed by a surgeon), or other suitable source of additional information related to a surgical procedure. For example, the third party device data may be ported to a panel that is displayed to a surgeon before, during or after a procedure.

As another example, one or more application databases 342 may be connected to the network 317 (or alternatively, stored locally within a memory 320 within the surgical robotic platform 302). The application database 342 may include software applications (e.g., as described in further detail below) that may be of interest to a surgeon during a procedure. For example, a software application may provide access to stored medical records of a patient, provide a checklist of surgical tasks for a surgical procedure, perform machine vision techniques for assisting with a procedure, perform machine learning tasks to improve surgical tasks, etc. Any suitable number of applications may be invoked. Information associated with an application may be displayed in a multi-panel display or other suitable display during a procedure. Additionally or alternatively, information provided by one or more applications may be provided by separate resources (e.g., a machine learning resource) otherwise suitably in communication with the surgical robotic platform 302.

In some variations, one or more of the software applications may run as a separate process that uses an application program interface (API) to draw objects and/or images on the display. APIs of different complexities may be used. For example, a simple API may include a few templates with fixed widget sizes and locations, which can be used by the GUI module to customize text and/or images. As another example, a more complex API may allow a software application to create, place, and delete different widgets, such as labels, lists, buttons, and images.

Additionally or alternatively, one or more software applications may render themselves for display. This may, for example, allow for a high level of customization and complex behavior for an application. For example, this approach may be implemented by allowing an application to pass frames that are rendered by a GUI module 324 (described below). Alternatively, an image buffer may be used as a repository to which an application renders itself.

In some variations, one or more software applications may run and render themselves independent of the GUI module 324. The GUI module may still, however, launch such applications, instruct the application or the operating system where the application is to be positioned on the display, etc.

As another approach, in some variations, one or more applications may run completely separate from the GUI rendered by the GUI module. For example, such applications may have a physical video connection and data connection to the system (e.g., through suitable input/output devices, network, etc.). The data connection may be used to configure video feed for an application to be the appropriate pixel dimensions (e.g., full screen, half screen, etc.).

As shown in FIG. 3, in some variations, a memory 320 may also be connected to the bus 314. The memory 320 may be configured to store data processed in accordance with embodiments of the methods and systems described herein.

In some variations, the memory 320 may be configured to store other kinds of data and/or software modules for execution. For example, a user console may include a memory 320 that stores a GUI module 324 with executable instructions to implement operations disclosed herein. The GUI module may, for example, combine and aggregate information from various software applications and/or other medical data resources for display. In some exemplary variations, one or more software applications may be incorporated into base code of the GUI module, such that the module draws graphics and displays text in the appropriate location on the display. For example, the module may fetch the images from a database, or the images may be pushed to the interface from an instrument (e.g., endoscopic camera) in the operating room, via a wired or wireless interface.

In some variations, medical data may be collected from discrete medical data resources (e.g., surgical robot 330, endoscope 332, medical instrumentation 334, control devices 336, third party data source 340, application database 342, etc.). Additionally, at least some of the medical data may be temporally coordinated such that, when necessary, time sensitive information from different medical data resources is aligned on a common time axis. For example, surgical robot position data may be time coordinated with endoscope data, which is coordinated with operator interaction data from control devices. Similarly, a networked resource, such as information provided by one or more software applications, may be presented at an appropriate point in time along with the other temporally coordinated data. Multi-panel displays, and/or other suitable displays, may be configured to communicate medical information (e.g., including the temporally coordinated medical data) as part of a graphical user interface (GUI).

Various exemplary aspects of a GUI for a robotic surgical system are described herein. In some variations, the GUI may be displayed in a multi-panel display at a user console that controls the robotic surgical system. Additionally or alternatively, the GUI may be displayed at one or more additional displays, such as at a control tower for the robotic surgical system, at a patient bedside, etc. Another example of a display on which the GUI may be displayed is an immersive display such as those described in U.S. patent application Ser. No. 15/724,185 titled "IMMERSIVE THREE-DIMENSIONAL DISPLAY FOR ROBOTIC SURGERY" which was filed Oct. 3, 2017 and is incorporated herein in its entirety by this reference. Generally, the GUI may provide for more effective communication of information to a user in the user console and/or other personnel, as well as for more effective communication and collaboration among different parties involved in a surgical procedure, as further described below.

Graphical User Interface (GUI)

A GUI for a robotic surgical system may provide informative and/or interactive content, to thereby assist a user in performing a surgical procedure with one or more robotic instruments in the robotic surgical system. For example, some of the content may be displayed via one or more software applications (e.g., modules, widgets). In some variations, at least some of the content provided by the GUI may be overlaid or displayed proximate an image of the surgical site (e.g., from an endoscopic camera), such as during a surgical procedure. Such software applications may be selectively activated by the user to display their content. Exemplary software applications, and the content they may provide, are described in further detail below. Additionally, the manner in which the selected software applications display their content (e.g., layout, size on the display) may be customized by the user. Accordingly, in some aspects, the GUI may provide an interactive, customizable experience for the user.

Layouts

In some variations, the GUI may include a multi-panel display (or on multiple adjacent displays). Various software applications within the apps may be selectively arranged on the multiple panels to display their respective content in a reconfigurable manner. For example, information relating to multiple software applications may be displayed on multiple reconfigurable panels of a display. Different layouts of the reconfigurable panels may result for example, from adjusting sizes and/or shapes of different panels. Additionally or alternatively, different layouts may result from the population of different content (e.g., different applications) in the multiple display panels.

Figure 5A:
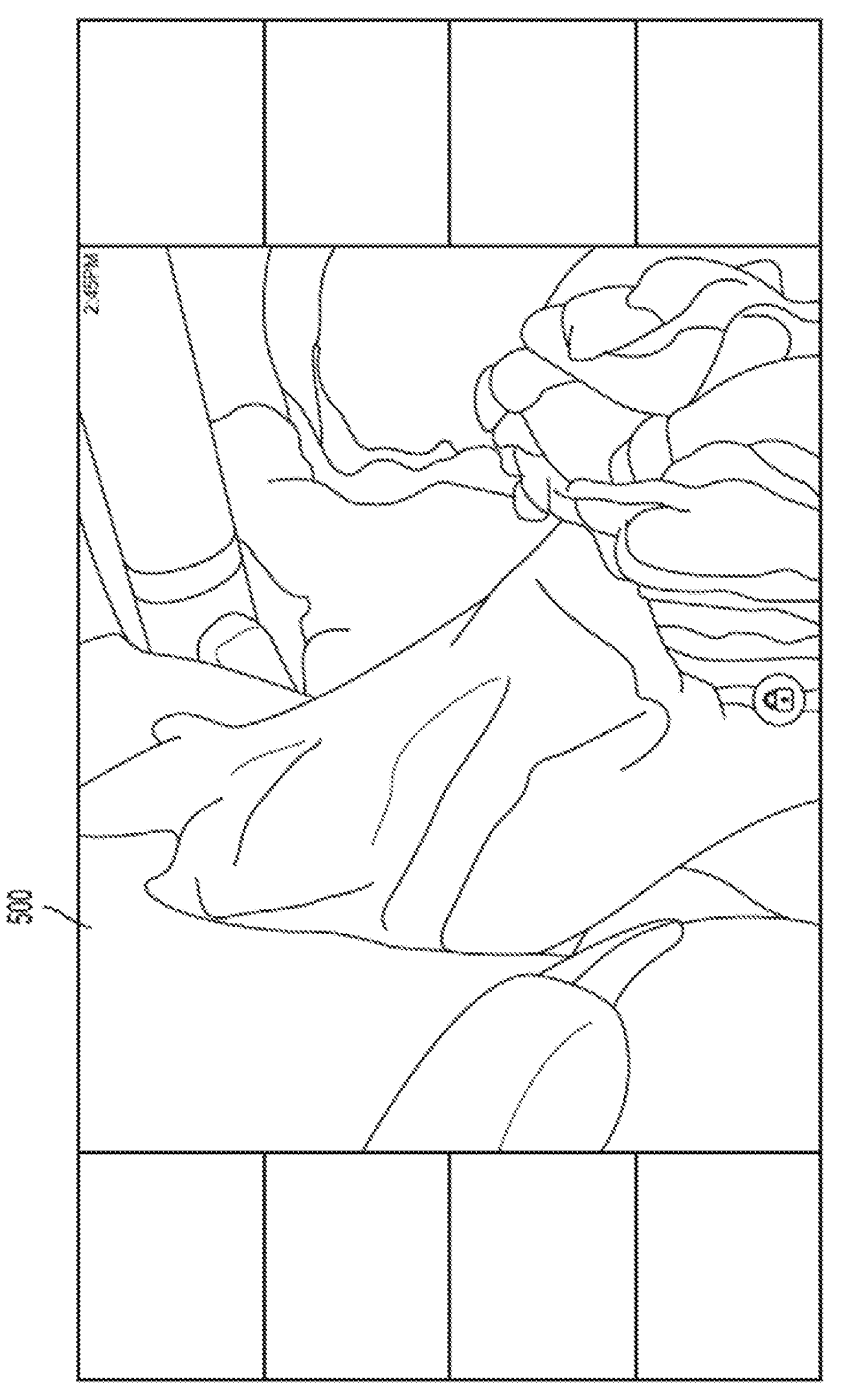
FIGS. 5A-5F are exemplary variations of different layouts for a multi-panel display for a GUI in a robotic surgical system.
Figure 5B:
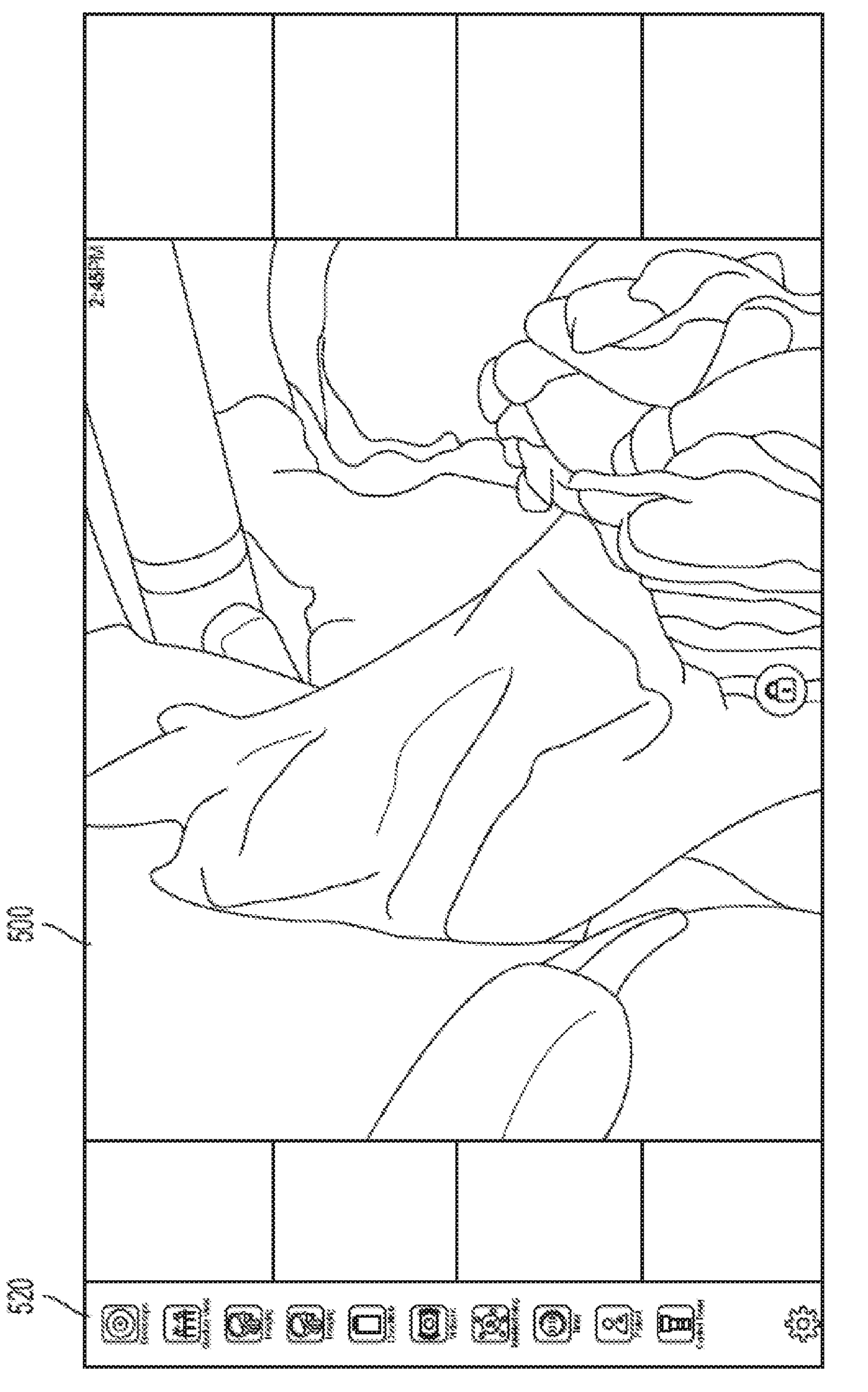

Generally, a user (e.g., surgeon, other surgical staff) may populate various panels of a display with different applications, by selecting, for example, which applications are visible and where within an application layout they are placed on the multi-panel display. Accordingly, the user may define his or her application environment as displayed on at least one multi-panel display. For example, as shown in FIG. 5B, a user may access an application tool bar 520 that is populated with selectable icons representing various applications. The application tool bar 520 may be hidden by default and pulled up for display when a user wishes to set up a display layout, swap between applications for display, etc. Using one or more input devices (e.g., handheld user input device, foot pedal) and/or through other sensors such as eye-tracking or head-tracking sensors, a user may select desired applications from the application tool bar 520 to become rendered on the display. Selected applications may be rendered on a display according to a template layout. The user may additionally or alternatively rearrange and/or resize the displayed applications (e.g., by clicking and dragging) to a desired layout. In some variations, a user may similarly set up one or more various panels of a display through a web portal or other online environment. In these variations, for example, the user may predefine the application environment on the multi-panel display before the entering the operating room. Furthermore, the application environment may be defined or predefined in different manners (e.g., which applications and their layout) for different screens, such as a first layout for an open display in a surgeon console, a second layout for a control tower display, a third layout for a bedside nurse display, and/or a fourth layout for an overhead "stadium"-style screen, etc.

Furthermore, the GUI layout may be dynamic throughout a surgical procedure. For example, the importance of various content may differ depending on surgeon needs, what is happening during a surgical procedure, etc. Accordingly, as it may become more useful to have content from different applications or data sources be presented in a larger viewing area, the layout may change from time to time. In some variations, the user may manually move location and/or size of different panels, such as by clicking or dragging, by voice command, by eye-tracking and/or head-tracking sensors, etc.

In some variations, the layout may change automatically. For example, if the system detects that a user is controlling handheld user input devices to control a robotic surgical instrument in a surgical site, the GUI may automatically display an endoscopic image of the surgical site in a large panel in order to provide a large viewing area for the user to see in better detail what is happening at the surgical site. As another example, if the system subsequently detects that the user has paused control of the robotic surgical system and detects (e.g., through an eye-tracking sensor) that the user is viewing a DICOM image, the GUI may automatically move the endoscopic image to a smaller panel, and move the imaging application to a larger panel to make the image easier to analyze. As yet another example, the system may detect that the user has completed a particular surgical task in a surgical procedure (e.g., through machine vision techniques) while viewing the endoscopic image in a large panel and the procedure template application in a small panel. In response, the GUI may automatically briefly swap the panel locations of the procedure template application and the endoscopic image, such as to more prominently indicate completion of the surgical task for a predetermined period of time before resuming display of the endoscopic image in the larger panel and the procedure template application in a small panel. As another example, if the system detects that a collision between robotic arms imminent, the GUI may automatically display a rendering of the robotic arms in a stadium view application (described below) in a larger panel in order to more prominently alert the user to the existence and nature of the collision. Other suitable events may trigger an automatic change in the layout of the GUI.

FIGS. 4A-4E are schematic illustrations of exemplary layouts for a multi-panel GUI. As shown in FIG. 4A, one exemplary layout for a multi-panel GUI includes one large, main panel 400 located centrally or in the middle of the display. The main panel 400 may be flanked by four left-side panels 410*a*-410*d* and four right-side panels 410*e*-410*h*. This layout may be useful, for example, to a user desiring to display content of primary interest (e.g., an image of a surgical site) in a large panel and supplemental content (e.g., from applications such as those described below) in smaller panels. An exemplary implementation of this layout is shown in FIG. 5A, which depicts a central panel 500 configured to display an endoscopic image of a surgical worksite including tissue and surgical tools, and four panels on each side of the central panel 500, where the side panels are available to be populated by content from applications. It should be understood that smaller panels may additionally or alternatively be displayed along a top edge of the display and/or along a bottom edge of the display.

Figure 5C:
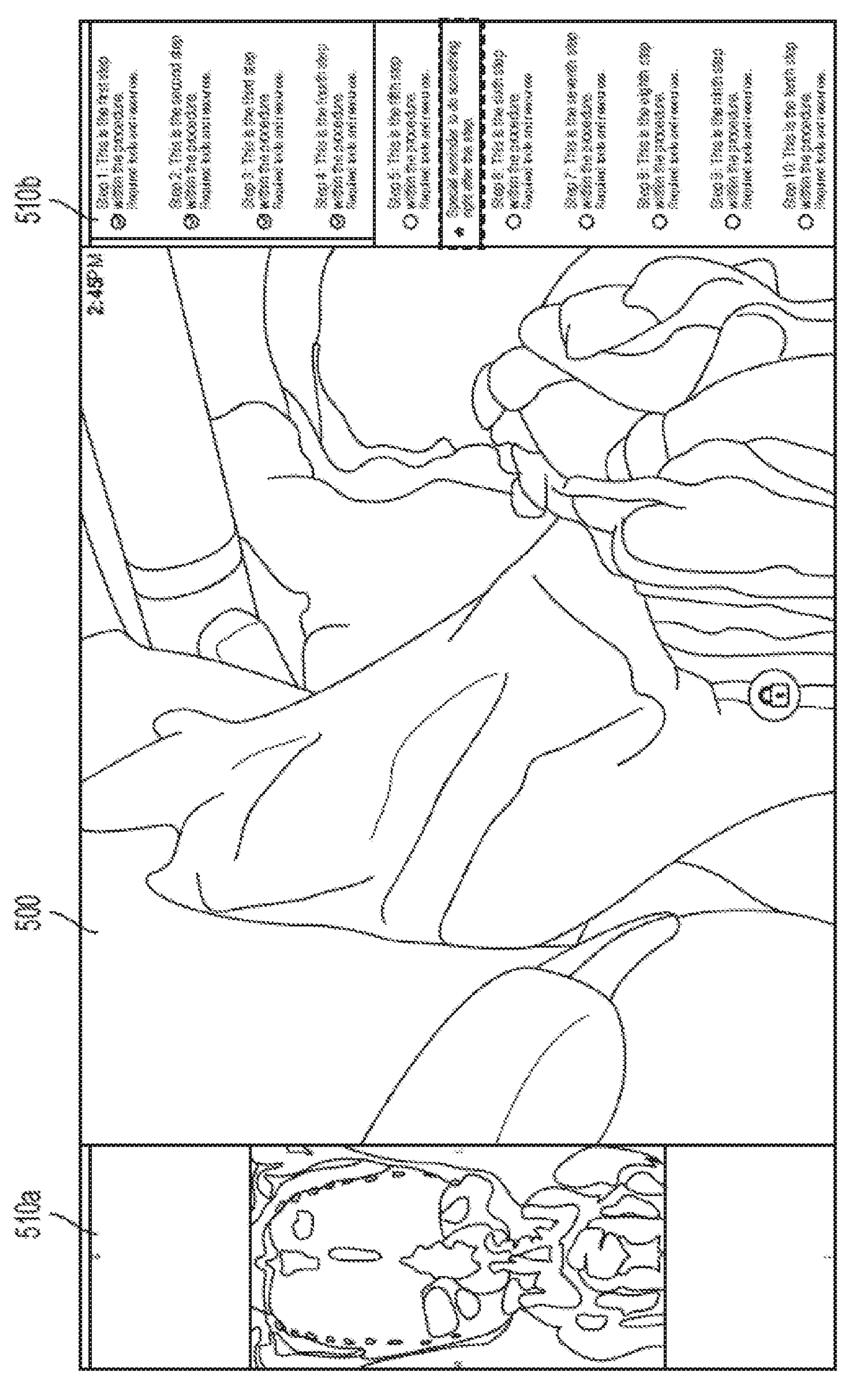

Although FIG. 4A shows four panels on each side of the main panel 400 for displaying information from applications, it should be understood that in other variations the left and right sides may include any suitable number of additional panels of suitable sizes. For example, as shown in the schematic of FIG. 4B, a main panel 400 may be flanked by a single left-side panel 410*a* and a single right-side panel 410*b*. The left- and right-side panels may be larger than those in FIG. 4A, in order to facilitate better viewing of content from applications displayed in the side panels. An exemplary implementation of this layout is shown in FIG. 5C, which depicts a central panel 500 configured to display an endoscopic image of a surgical worksite, a single left-side panel 510*a* configured to display content from an image viewer application (described below), and a single right-side panel 510*b* configured to display content from a procedure template application (described below).

Figure 5D:
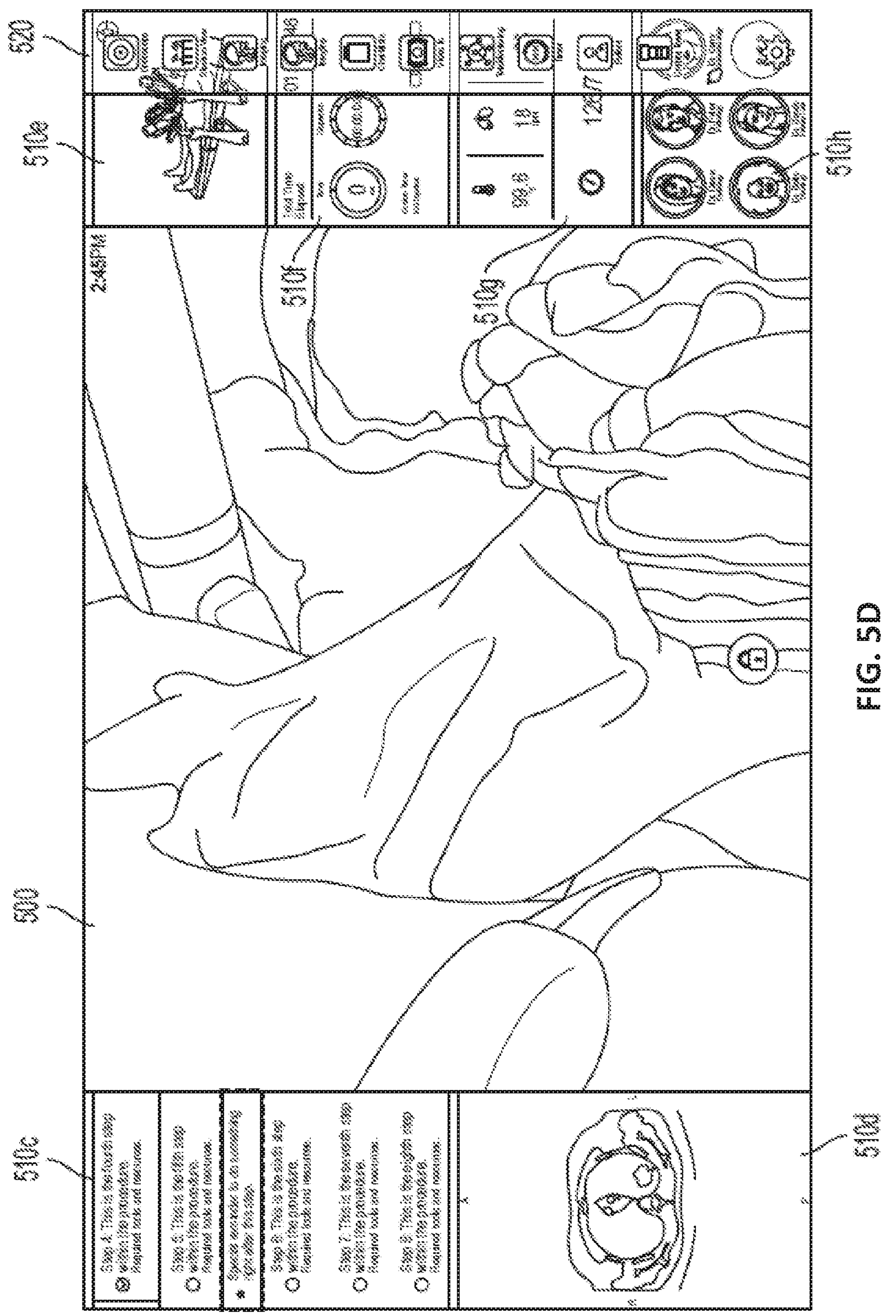

Additionally, the number of applications displayed on a left side of the main panel may be different than the number of applications displayed on a right side of the main panel. For example, as shown in FIG. 5D, a left side of the main panel 500 may include two panels 510*c* and 510*d* for displaying content from a procedure template application and an image viewer application, respectively, while a right side of the main panel may include four panels 510*e*-510*h* for displaying content from a stadium view application, a timer application, a patient vitals viewer application, and a teleconferencing application (all described below).

In some variations, smaller panels may be collected on one side of a main panel, rather than flanking the main panel on two sides. For example, as shown in the schematic shown in FIG. 4C, a main panel 400 may be displayed with a group of smaller, left-side panels 410*a*-410*e*. Furthermore, some of left-side panels may be different sizes (e.g., side panel 410*a* is a medium-sized panel, while side panels 410*b*-410*e* are smaller panels arranged in quadrants) to enable different viewing areas for various content of the applications displayed in the left-side panels. It should be understood that smaller panels may alternatively be displayed on the right side of the display, along a top edge of the display, along a bottom edge of the display, and/or other suitable location.

Figure 5E:
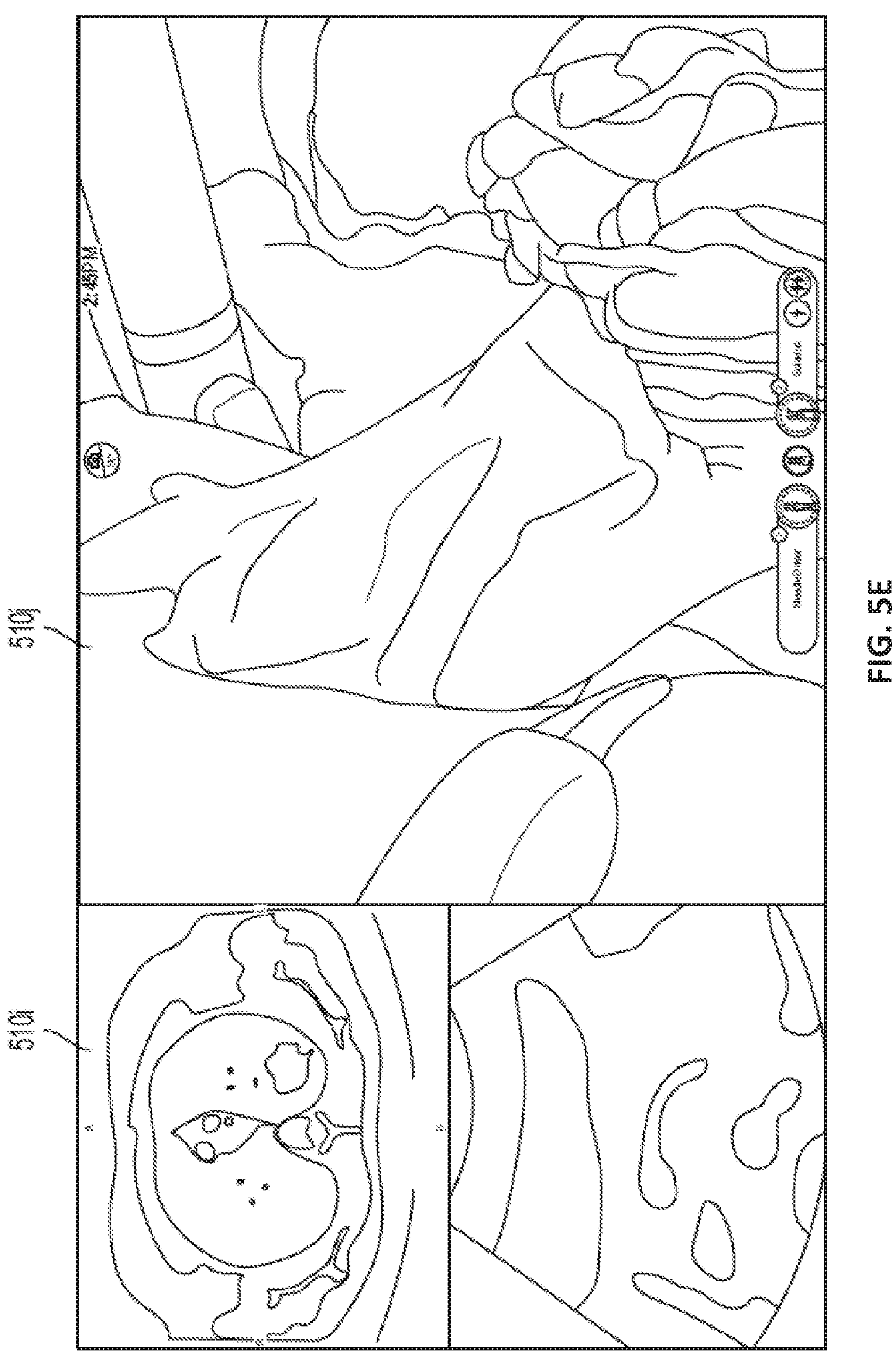
Figure 5F:
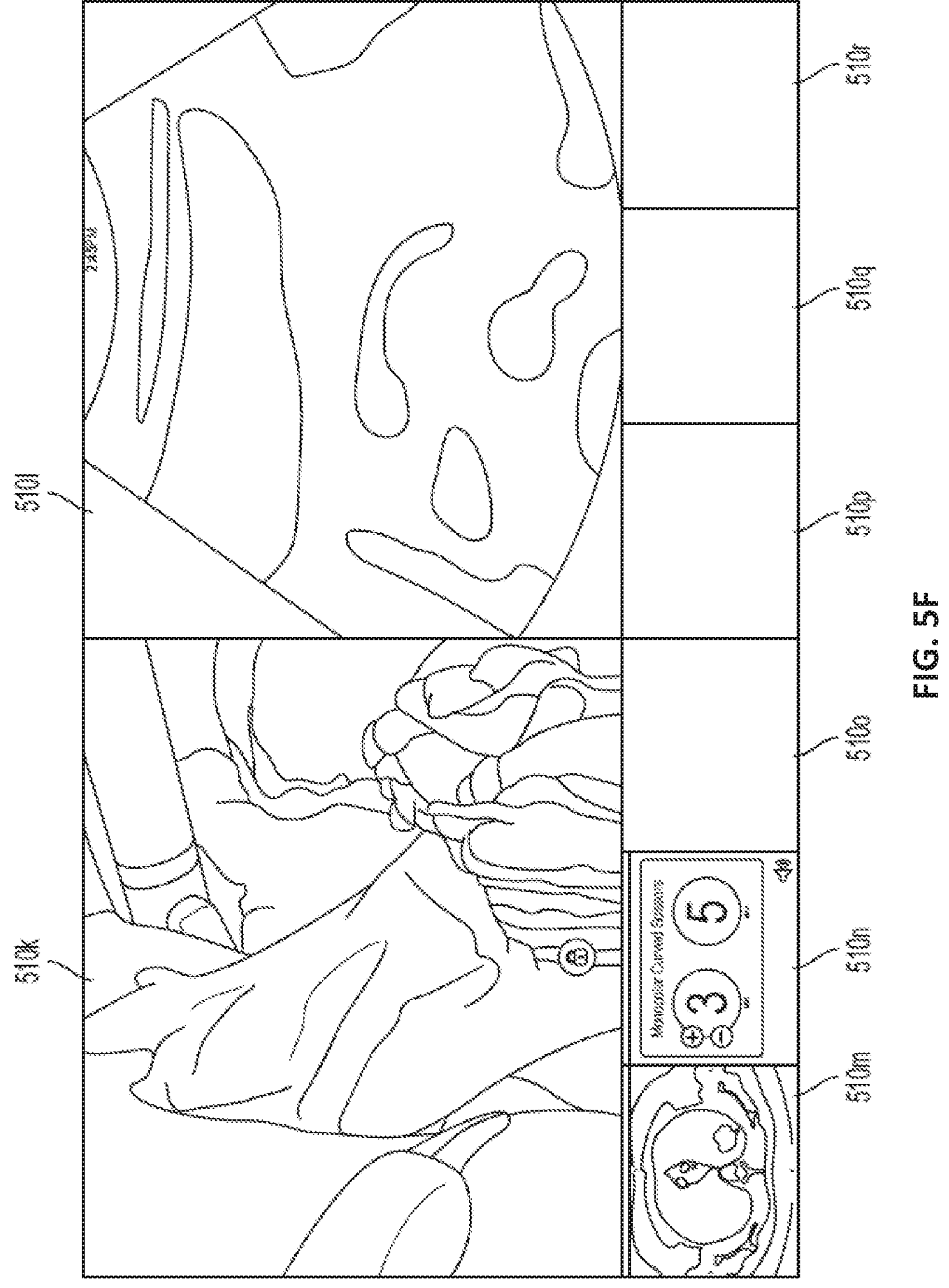

Some of the panels in the GUI may be sized to provide large viewing areas of content for multiple data sources. For example, as shown in the schematic of FIG. 4D, each of two large panels 410*a* and 410*b* is displayed on about half of the available viewing area, and may collectively occupy substantially all of the available viewing area of the display. Although FIG. 4D depicts the two large panels being substantially equal sizes, in other variations, one of the larger panels may be slightly larger than the other (e.g., one panel may be between about 50% and about 75% of the viewing area of the display, while the other panel may be between about 25% and about 50% of the viewing area of the display). Additionally or alternatively, the larger panels may be arranged vertically, with one on the top and the other on the bottom of the display. An exemplary implementation of two large side-by-side panels is shown in FIG. 5E, which depicts a left-side panel 510*i* that is configured to display content from an image viewer app that occupies about 25% of the viewing area, and a right-side panel 510*j* that is configured to display an endoscopic image that occupies about 75% of the viewing area of the display. It should be understood that fewer (e.g., a single main panel) or more (e.g., three panels, four panels, etc.) may collectively occupy substantially all of the available viewing area of the display. For example, as shown in the schematic of FIG. 4E, two large panels 410*a* and 410*b* may occupy the majority of the viewing area of the display, while six smaller panels 410*c*-41*h* may be arranged along the bottom edge of the display (or alternatively the top). An exemplary implementation of this layout is shown in FIG. 5F, which depicts larger side-by-side panels 510*k* and 510*l* configured to show an endoscopic image and content from an image viewer app, respectively, as well as smaller panels 510*m*-510*r* arranged beneath the panels 510*k* and 510*l*.

The above-described layouts are illustrative examples only. In some variations, a user may customize the number of panels, the size of panels, and/or the shape of the panels to obtain a GUI layout that differs from these examples. At least some of the layouts described herein may be stored as template layouts that may be selected by a user. For example, in some variations, one or more of the template layouts may be associated with one or more surgical procedure types (e.g., as a default or preferred layout for a particular kind of surgical procedure). As another example, one or more of the template layouts may be associated with one or more user profiles (e.g., so a user-preferred layout may be automatically recalled and rendered upon a user login to the system or other suitable user identification). As yet another example, one or more of the template layouts may be associated with one or more user types, such as a simplified layout (e.g., fewer panels) for an inexperienced user or a more complicated layout (e.g., more panels) for an experienced user.

Applications

As described above, the GUI may be configured to display specialized content from one or more selected software applications. A user may access an application tool bar and select, via an input device or interaction with other suitable sensors, one or more desired applications for display in a multi-panel display. Applications may be represented by graphical icons in the application tool bar, and may be arranged in any suitable order, such as grouped by relevance or functionality (e.g., relating to the surgical procedure, relating to the patient, relating to team collaboration), alphabetically, user-selected "favorites," most popular, etc. Various exemplary kinds of software applications are described below, though it should be understood that other variations of software applications may be provided in a GUI.

Figure 6:
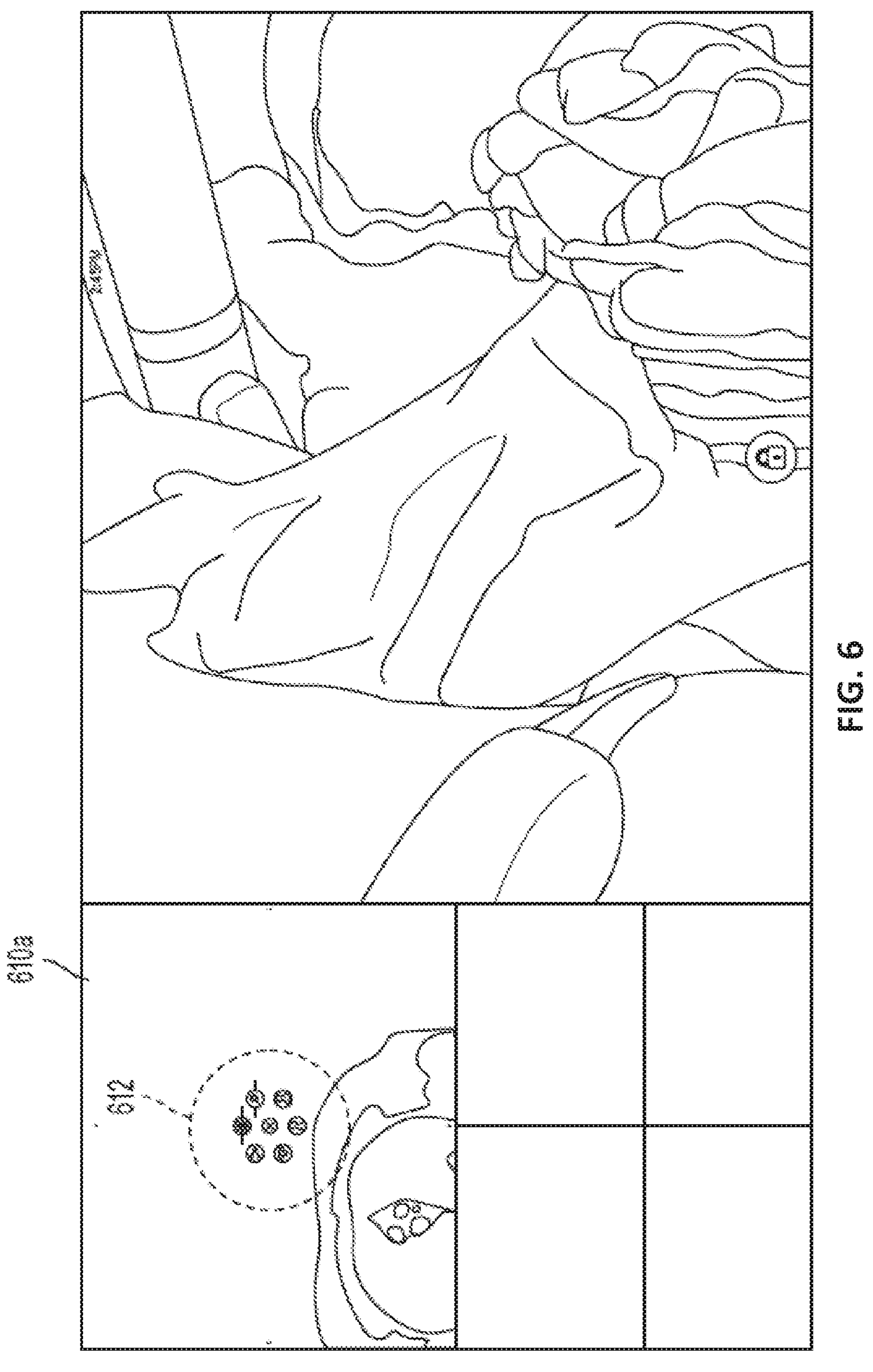
FIG. 6 is an exemplary variation of a GUI depicting an application submenu.

At least some of the software applications may have navigable content. In some variations, one or more of the software applications may be navigable with a submenu. For example, as shown in FIG. 6, a software application (e.g., image viewer application) may include a submenu 612 with a plurality of icons, where each icon is associated with a respective functionality or operation within the application. As shown in FIG. 6, the icons are arranged generally in a ring, but may alternatively be arranged in any suitable manner. Furthermore, any suitable tree hierarchy in submenu items may be provided in a software application, such that selection of a submenu icon may prompt display of one or more second-submenu icons relating to the selected submenu icon, and so on.

Some submenu functionalities may be generally applicable across many applications. For example, one exemplary submenu functionality is a search function, which may enable a user to perform a search for specific content provided by the application (e.g., in an image viewer application, a user may search for pre-operative images from a desired date). Another exemplary submenu functionality is a share function, which may enable a user to share the displayed content of that application with another party (e.g., with another display in the room such as a bedside display, with a third party device outside the room, etc.). Additionally or alternatively, some submenu functionalities may be particular to the selected application to which the submenu belongs. For example, an image viewer application may include a submenu with interactive tools for image adjustment (e.g., contrast, saturation, sharpness, etc.). In some variations, certain submenu items may be "saved" by a user to be displayed automatically per user preference, and/or may be reordered in tree hierarchy depending on surgical procedure type or any suitable factor.

Image Viewer Application

One variation of an application for the GUI is an image viewer application. The image viewer application may be in communication with a medical records database or other suitable repository such that the image viewer application may receive medical images relating to the surgical procedure. For example, the image viewer application may receive and display pre-operative images (e.g., X-ray, CT, MRI, ultrasound, etc.) of the patient. Such display of pre-operative images may allow a surgeon and/or other user(s) to easily view pre-operative images before, during, and/or after a surgical procedure and may help the surgical team make better, more informed decisions relating to the surgical procedure. For example, pre-operative images may be displayed via the image viewer application in order to facilitate pre-operative planning, such as the surgical team reviewing a surgical plan at the outset of a case. As another example, pre-operative images may be displayed via the image viewer application side-by-side with real-time, intra-operative images obtained with an endoscopic (e.g., to assess margins of a tumor to be excised). As another example, pre-operative images may be shared via the image viewer application with other parties, such as another display in the operating room or a third-party device outside the room. As yet another example, pre-operative images may be reviewed post-operatively to assess whether surgical treatment goals have been met.

Figure 7:
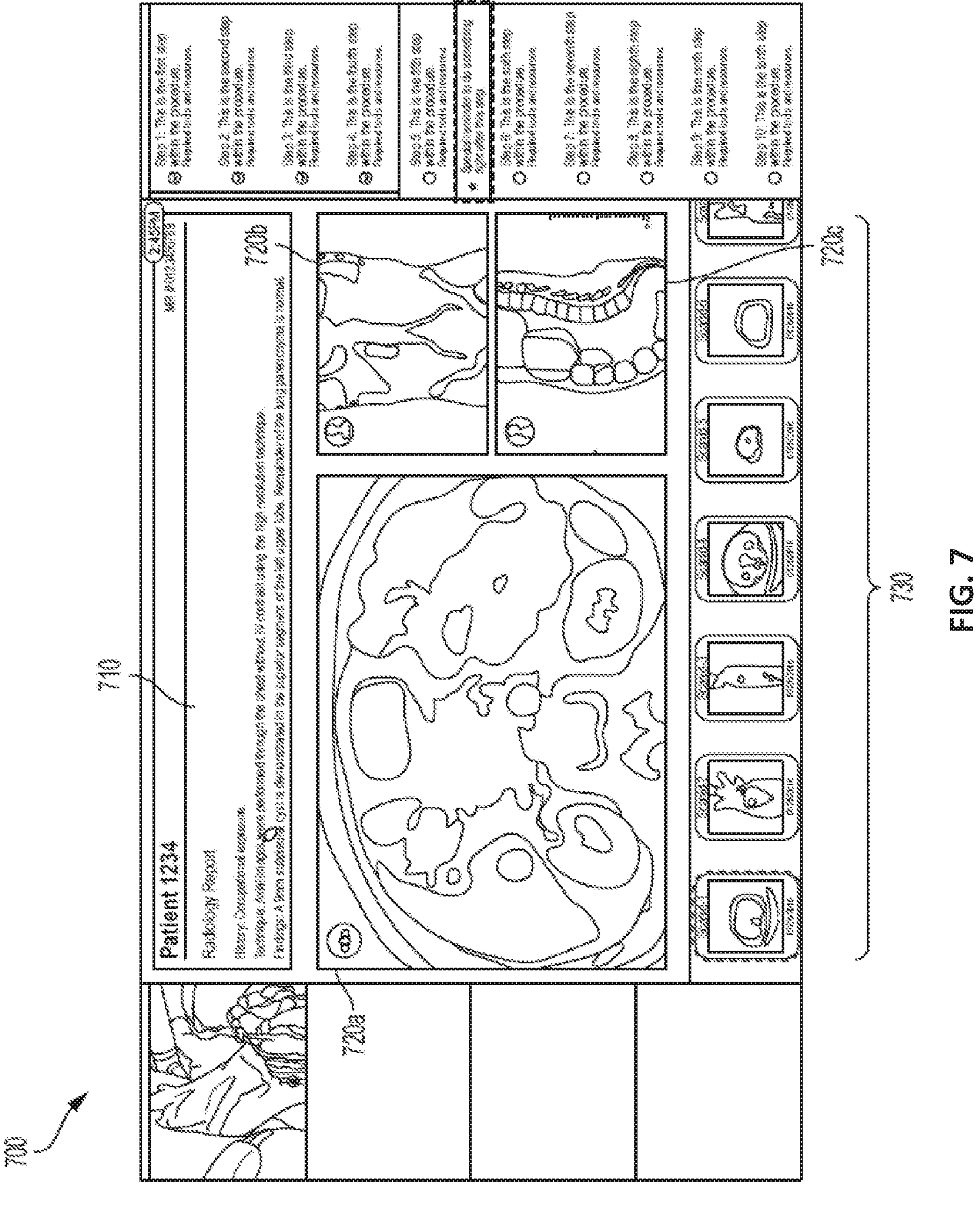
FIG. 7 is an exemplary variation of a GUI including an image viewer application.

As shown in the exemplary implementation of an image view application 700 of FIG. 7, the image viewer application may include multiple subpanels displaying various images and/or image-related information. In this example, a subpanel 710 may display image identifying information such as patient name, patient medical records number, type of image, method by which the image was taken, and date of image. Other related information such as diagnostic information or other findings based on pre-operative analysis information may also be provided.

One or more subpanels (shown as subpanels 720*a*-720*c*) may display the pre-operative images. Multiple subpanels may simultaneously show multiple images, such as different views of a volume of tissue (e.g., sagittal, transverse and/or coronal views). Each respective view of tissue may be labeled, such as with words or a graphical icon representing the view. Additionally or alternatively, thumbnail views of other images may be displayed in subpanel 730. Each thumbnail may be associated with a single image, or may be associated with an image series (e.g., multiple images taken on the same date). The image view application may permit a user to scroll through the thumbnail views, such as with a handheld user input device as described below, or in any suitable manner. In response to a selection (or clicking and dragging, etc.) of any one or more of the thumbnails, the image view application may display one or more images associated with the selected thumbnail in a larger subpanel. In some variations, the image viewer application may automatically resize the size of the larger subpanels in response to the addition of another image selected to be viewed. For example, if one of the thumbnails in the subpanel 730 is selected, the image viewer application may automatically reduce the sizes of the subpanels 720*a*-720*c* to accommodate the display of a fourth image associated with the selected thumbnail.

Real-Time Video Application

Another variation of an application for the GUI is a video application configured to receive and display one or more real-time image data from devices capturing images of a surgical worksite during a surgical procedure. In some variations, the real-time video application is configured to receive and display information in addition to an endoscopic video feed from the robotic surgical system, such as through additional (e.g., third-party) endoscopic devices, ultrasound machines, etc. Display of additional real-time data streams to a user may, for example, help enable surgical staff to view more information (e.g., from different angles or perspectives, with different imaging aids such as ICG or other imaging agents, etc.) that may help them make better treatment decisions. In some variations, the real-time video application may additionally or alternatively receive image data from an endoscopic video feed from the robotic surgical system.

Patient Vitals Application

Another variation of an application for the GUI is a patient vitals application. The patient vitals application may be in communication with one or more sensors tracking patient vital signs (or in communication with a memory device storing the same) such as pulse, blood pressure, oximetry data, respiratory rate, temperature, and the like. The display of patient vitals on the display may provide a surgeon and/or other user with easy access to a status of the patient (e.g., without having to ask a present anesthesiologist). The display of patient vital signs in the patient vitals application may, for example, help enable a surgeon react more quickly to emergency situations. Furthermore, the patient vitals application may provide a visual and/or audio alert for trigger events, such as a patient vital meeting a predetermined threshold value (e.g., heart rate exceeding a predetermined value).

An exemplary implementation of a patient vitals application is shown in panel 510*g* in FIG. 5D. As shown in FIG. 5D, in some variations, patient vitals may be accompanied by graphical representative icons relating to the patient vitals, such as a thermometer to indicate that a value is for patient temperature.

In some variations, the patient vitals application may additionally receive and display information relating to vitals, biometrics, etc. of a user (e.g., a surgeon at a user console, or another member of the surgical team) in order track status of the user. For example, user vitals such as pulse rate, blood pressure, breathing rate, etc. may be tracked and displayed to help enable monitoring of a user for any signs of an adverse state such as stress, fatigue, inebriation, or any suitable health characteristic. Additionally or alternatively, user vitals may be received and displayed by a separate user vitals application which may be similar to the patient vitals application. For example, as described above, a software application may provide a visual and/or audio alert for triggering events relating to user vitals, such that one or more corrective actions (e.g., swapping in another surgeon, pausing a surgical task or surgical procedure, etc.) may be taken.

Procedure Template Application

One variation of an application for a GUI is a procedure template application. The procedure template application may be in communication with a procedure database stored in memory, such that it may receive data relating to procedure planning. The procedure template application may generate a list of items relating to performance of a surgical procedure. For example, the procedure template application may display a checklist of surgical tasks that are part of a surgical procedure, list of equipment or tools needed for the surgical procedure, list of operating room setup tasks, a schematic diagram of port location and arm/surgical instrument setup, etc. In some variations, a checklist may be a template list, or may be customized (e.g., a template checklist that has been fine-tuned or adjusted for a particular patient, or an otherwise customized list). The procedure template application may, for example, provide a way for the surgical team to view procedure steps, equipment, and/or setup tasks before or at the outset of a surgical procedure.

At least some of the items on a procedure template may include notes relating to the item. For example, notes may be associated with one or more items on the list in order to customize a template list to a particular patient. Notes may include, for example, comments relating to pre-operative findings (e.g., specific location of a tumor, aberrant anatomy, adhesion, tumor margins, lymph node involvement, etc.), links to relevant pre-operative images (e.g., in communication with an image viewer application, one or more images depicting tumor margins, regions of interest, image overlays, etc.), more detailed description of a surgical task, video clips of surgical tasks, etc. In some variations, one or more of the items may include secondary items organized hierarchically under a larger item. For example, a general surgical task such as "create incision in patient" may include secondary tasks such as "locate desired port location," "sterilize desired port location," "cut into patient," etc. As another example, a general surgical task may additionally or alternatively include one or more secondary items that are related to subsequent tasks for procedure planning purposes. For example, while a first general surgical task may utilize a first surgical instrument attached to a particular arm (e.g., scalpel), a second general surgical task may utilize a second surgical instrument (stapler) to be attached to the same arm after the first surgical instrument is no longer needed. In this example, the procedure template application may display the first general surgical task and display a secondary item relating to replacing the first surgical instrument with the second surgical instrument (e.g., "Swap scalpel with stapler") organized under the first general surgical task, even though the second instrument is not needed to perform the first surgical task.

In some variations, the displayed items on the checklist may be sequentially ordered, such as in an anticipated order of performance or relevance of the items. The display of items may be filtered, such as according to a category type. For example, in variations in which a procedure template includes an indication of equipment or tools needed for a particular surgical procedure, the user may select a filter to include only display of items relating to required equipment or tools (e.g., such that at the outset of a surgical procedure, the surgical team may quickly identify all equipment or tools that will be needed during the procedure and ensure all are available).

An exemplary implementation of a procedure template application is shown in panel 510*c* of FIG. 5D. For example, a full list of procedure template items for a surgical procedure may be displayed in a panel of the GUI. Alternatively, only a partial list of procedure template items for a surgical procedure may be displayed. For example, the current surgical task in progress may be displayed, along with a predetermined number (e.g., five) of subsequent surgical tasks, or along with a set of subsequent surgical tasks expected to be performed within a predetermined period of time (e.g., within the next thirty minutes or within the next hour).

In some variations, items currently relevant during a procedure, such as a current surgical task in progress, may be highlighted in the procedure template application display, while displayed items relating to the future may be dimmed in the procedure template application display. Data for expected duration of surgical tasks may be determined, for example, based on previous instances of the same type of surgical procedure performed. For example, this timing data for surgical tasks may be gathered via the timer application described below.

In some variations, during a surgical procedure, the procedure template application may incorporate or access machine vision techniques to identify when one or more items on the checklist are completed or otherwise no longer relevant. For example, machine vision techniques may identify in an endoscopic image feed when a certain surgical task is completed, and in response to identifying that the task is complete, the procedure template application may cross off that task (e.g., strikethrough or dim the display of that task, highlight the next task, etc.). Additionally or alternatively, a member of the surgical team may manually indicate that a particular item is complete. Furthermore, machine vision techniques and/or feedback from the surgical team regarding status or progress of the surgical procedure may be received by the procedure template application, which may trigger other suitable action items based on the status or progress of the surgical procedure. For example, based on current progress of the surgical procedure, the procedure template application may anticipate when a particular piece of equipment is needed for a particular task, and provide an alert or notification to the surgical team that the particular piece of equipment should be obtained (e.g., in advance of its associated task, so as not to slow down the surgical procedure).

Figure 22:
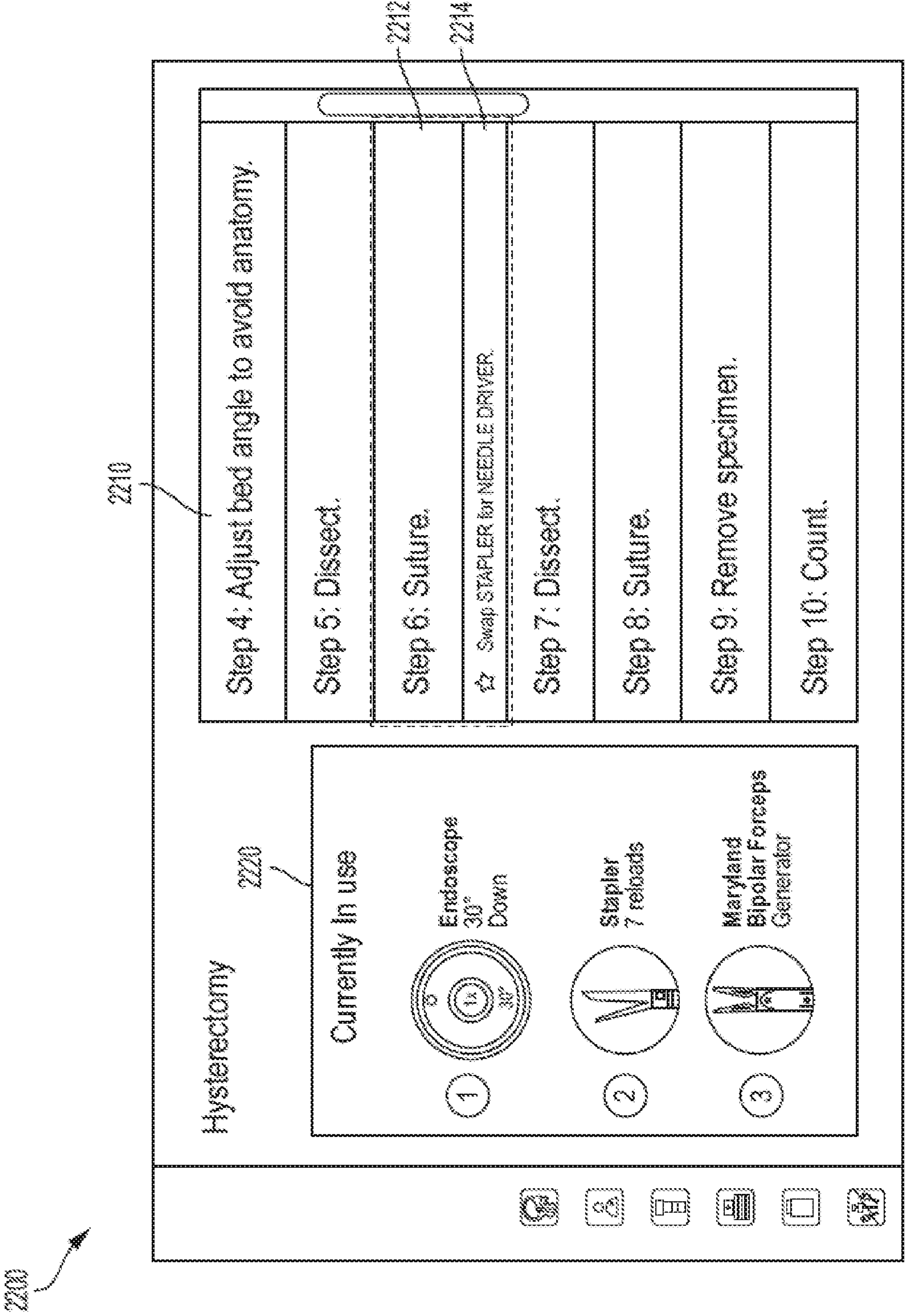
FIG. 22 is an exemplary variation of a GUI including a procedure template application with a surgical task checklist.

One exemplary implementation of a procedure template application is shown in FIG. 22. As shown in the procedure template application 2200, a surgical task checklist 2210 with one or more surgical tasks 2212 may be displayed. The surgical task checklist 2210 may include, for example, multiple steps (e.g., Step 4 through Step 10 as illustrated in FIG. 22) that are listed in sequential order of planned performance. At least one of the surgical tasks 2212 (e.g., "Step 6: Suture") may include one or more secondary items 2214 (e.g., "Swap STAPLER for NEEDLE DRIVER") that indicates another task organized hierarchically under a general surgical task. As shown in FIG. 22, in some variations, the procedure template application may additionally include other helpful information relating to the surgical procedure. For example, the procedure template application may display a surgical instrument list 2220 that indicates to which robotic arms the relevant surgical instruments are attached.

Figure 23:
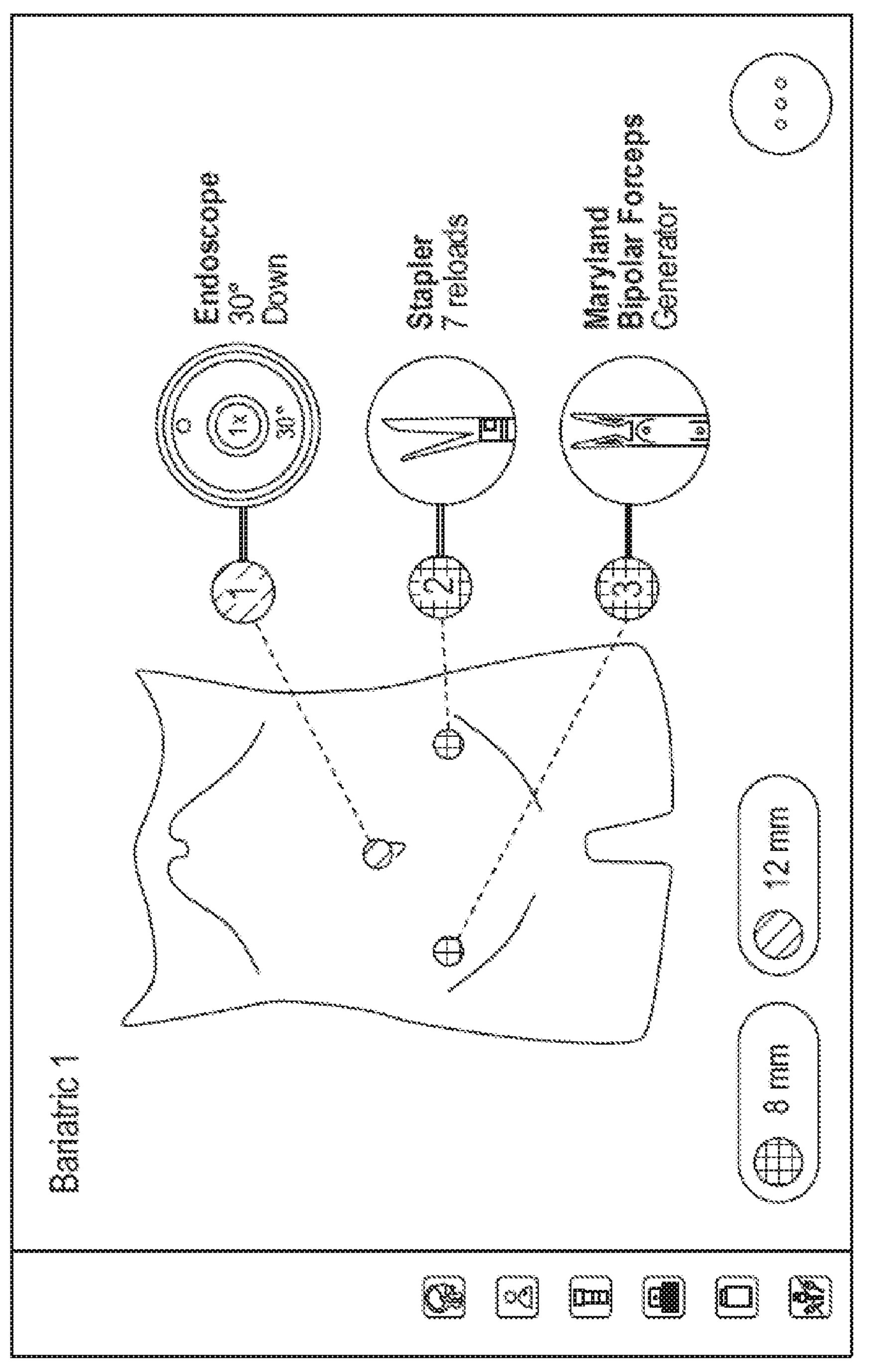
FIG. 23 is an exemplary variation of a GUI including a procedure template application with a port placement schematic diagram.

Another exemplary implementation of a procedure template application is shown in FIG. 23. As shown in the procedure template application 2300, a schematic diagram of surgical port locations on a patient may be displayed. The surgical port locations may map the relative locations of ports for entry of surgical instruments into the patient. Additionally or alternatively, one or more icons or graphical representations of surgical instruments may be displayed and associated with a respective port (e.g., via color coding and/or lines, etc.) to illustrate what kind of surgical instruments are currently in use, and where they are located. Such a map may, for example, be used to help guide the surgical team during setup before a procedure, during a surgical procedure to track type and location of the surgical instruments, etc. In some variations, the schematic diagram may also indicate anticipatory tool changes. For example, if a particular surgical instrument is to be swapped for another in accordance with a surgical task checklist, the icon for the surgical instrument to be swapped may change color, become animated (e.g., pulsate or blink), or change appearance in any suitable manner to confirm which surgical instrument is to be swapped. Similarly, as described elsewhere herein, the schematic diagram may display alert or other notifications if, for example, there are instrument errors or other faults.

As a surgical procedure progresses, the procedure template application (or a related application receiving an indication from the procedure template application) may in some variations cause display of an augmented version of the endoscopic image or other portion of the GUI. For example, if a current surgical task in progress relates to an incision placed at a particular location in patient tissue, the procedure template application may provide (or trigger another application to provide) an indication on the endoscopic image directing a user where to cut, such as with a dotted line and/or a labeled arrow. In other variations, any suitable kind of augmented images or displays may be triggered by progress of a surgical procedure that is tracked by the procedure template application or in any other suitable manner.

Timer Application

Another variation of an application for a GUI is a timer application. The timer application may, for example, track duration of the surgical procedure and/or duration of segments of the surgical procedure (e.g., individual surgical tasks and other tasks performed, and/or groups thereof). In some variations, the timer application may provide a way for medical staff to easily monitor progress of the surgical procedure intraoperatively. Additionally or alternatively, the timer application may analyze (or facilitate analysis of) performance of the surgical procedure post-operatively to help enable the surgical team identify possible ways to improve efficiency, communication, etc. In some variations, data gathered via the timer application may be displayed on other displays (e.g., additional displays in the operating room) and/or communicated and stored for later analysis. For example, data gathered via the timer application may be uploaded to a web portal or database to help enable an intra-operative and/or post-operative review of the surgical procedure.

Various time-related icons and/or metrics may be displayed within the timer application. For example, the timer application may provide one or more stopwatch timers to track elapsed time from one or more specific events. Such stopwatch timers may be user-activated (e.g., selection of a button, voice-activated) and/or automatically activated (e.g., in response to sensors or machine vision techniques identifying when a specific event has commenced). As another example, the timer application may provide a countdown timer for a specific event. Other charts or graphs may indicate performance metrics for the surgeon (e.g., progress of the procedure relative to previously performed procedures of the same type).

Figure 8:
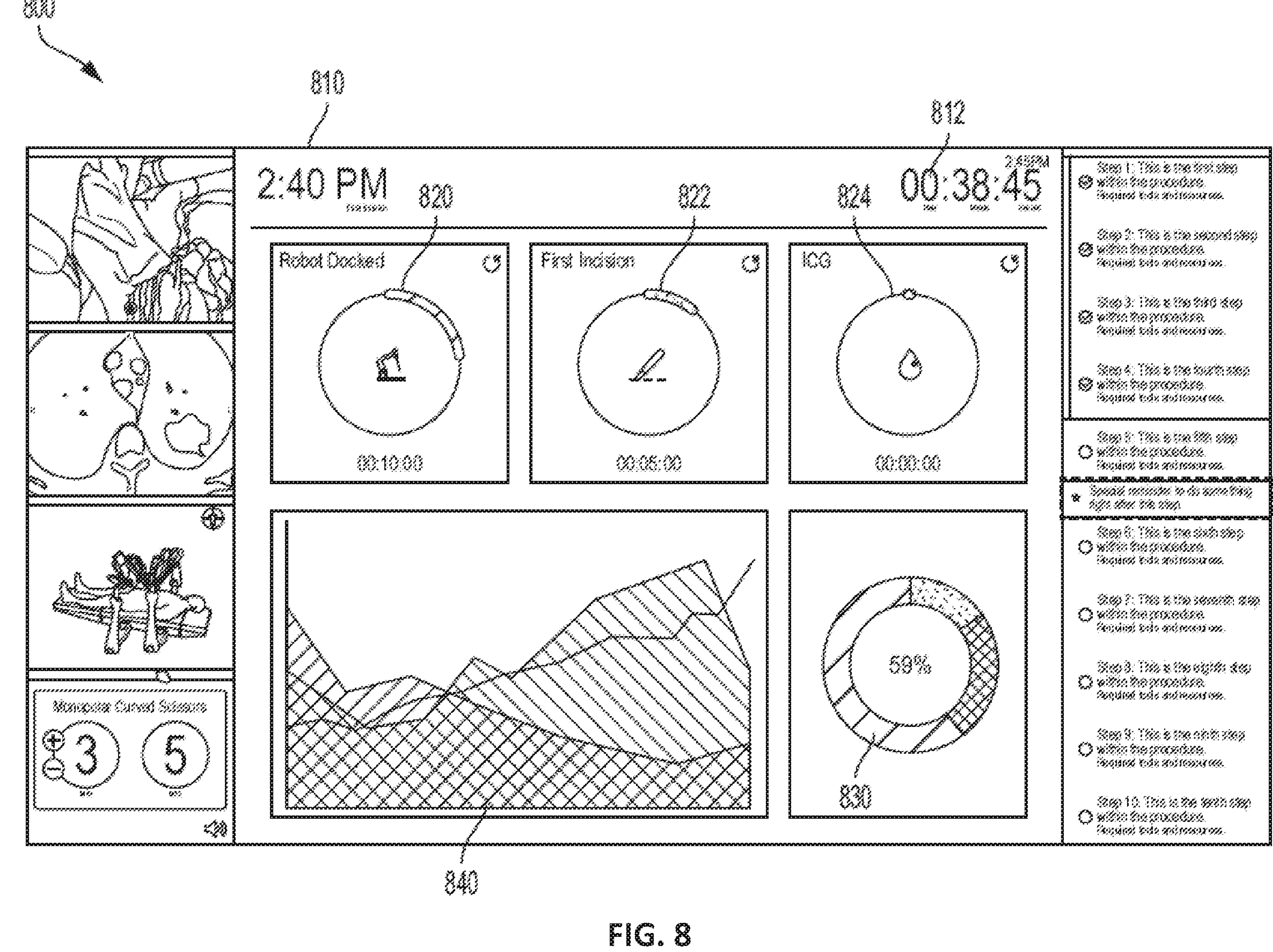
FIG. 8 is an exemplary variation of a GUI including a timer application.

An exemplary implementation of the timer application is shown in FIG. 8. As shown in this example, the timer application 800 may display a clock time of first incision 810 and/or an ongoing stopwatch timer for duration of the procedure 812. A first stopwatch timer 820 may track elapsed time since all robotic arms have been docked (coupled) to the patient. A second stopwatch timer 822 may track elapsed time since first incision. A third stopwatch timer 824 may track elapsed time since introduction of indocyanine green (ICG) or another suitable imaging agent into the patient.

A timer application may display a pie chart 830 or other suitable graphic that indicates the relative duration of separate events. For example, different segments of the pie chart 830 may be color-coded or otherwise indicated as associated with respective events (e.g., one segment associated with time elapsed for robot docking, another segment associated with time elapsed since introduction of an imaging agent, etc.). Although a circular pie chart 830 is depicted in FIG. 8, it should be understood that in other variations, data relating to events in the surgical procedure may be presented in any suitable manner.

A timer application may display a time chart 840 or suitable graphic that indicates performance metrics, such as progress of the current surgical procedure relative to previous procedures. For example, the current surgical procedure may be compared to other procedures of the same type, other procedures performed by the same user or similar users, other procedures performed on the same patient or similar patients, other procedures performed at the same hospital or other geographical category, etc. For example, the exemplary time chart 840 shown in FIG. 8 may include a line graph indicating progress of the current surgical procedure compared to background shaded graphs indicating progress of previous procedures. Progress of a surgical procedure may be measured in any suitable manner, including but not limited to number of surgical tasks completed for a given elapsed period of time (e.g., time to remove adhesion, time since ICG injection, etc.). In some variations, timer data may be used to track and aggregate training time (e.g., a user has completed 1000 hours of robotic surgery). As described above, in some variations, performance metrics may be communicated to a web portal or database for review and further analysis. In some variations, data from the timer application may additionally or alternatively be used by hospital administration users to develop operational metrics such as expected duration of a surgical procedure, such as to more efficiently or accurately plan an operating room schedule, and/or adjusting expected duration of a surgical procedure when certain portions of a procedure take longer than expected. As another example, data from the timer application may be used to provide recommendations for how to optimize operating room time (e.g., identifying and suggesting corrective action when a port placement segment of a procedure routinely takes longer in one operating room compared to another operating room).

Stadium View Application

Another variation of an application for a GUI is a stadium view application that provides a real-time view of the robotic system, patient table or bed, and/or staff in an operating room during a procedure. The stadium view application may, in some variations, receive real-time or near real-time information relating to a current position of the robotic arms, patient table, and/or staff and the like, generate a rendering (graphical representation) of the operating room environment based on the received information, and display the rendering to the user. In some variations, the rendering may be in 3D, but may alternatively be in 2D. Alternatively, the rendering may be generated by a remote device (e.g., a separate processor) and passed to the stadium view application for display. Accordingly, the displayed rendering may provide the user with an "outside-the-patient-body" view of the robotic surgical system, the patient, and/or staff, etc. in the operating room. The user may, for example, monitor status of the robotic system such as tool status, potential collisions, etc. and communicate to other members of the surgical team about such status and resolution of any issue. Furthermore, in some variations, the user may interact with the graphical representation within the stadium view application and effect one or more changes in the robotic surgical system, as described below.

The rendering of the operating room environment may be generated using various kinds of information. For example, a rendering of a robotic arm may be based at least in part on one or more kinematic algorithms that control a robotic arm. The one or more kinematic algorithms may be fed into a modeling module that transforms the kinematic information into a rendered 3D (or 2D) model. As another example, the rendering of a robotic arm, patient table, and/or staff (or other portion of the operating room environment) may be based at least partially on one or more sensors (e.g., position sensors in an arm, IR sensors around the room tracking markers placed on the arm, table, or surgical staff, etc.).

Figure 9A:
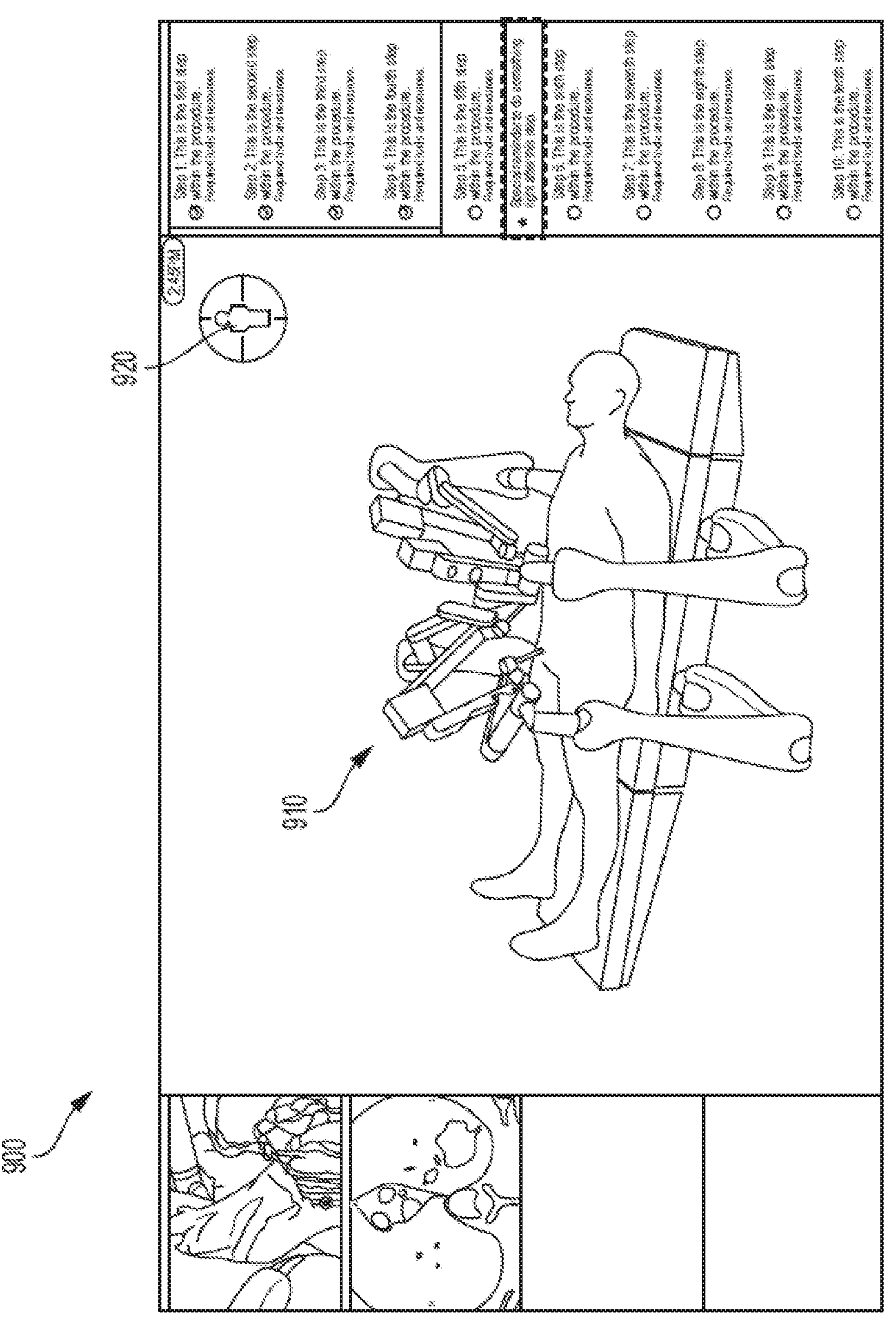
FIGS. 9A-9E are exemplary variations of a GUI including a stadium view application.

An exemplary implementation of a stadium view application is shown in FIG. 9A. As shown in FIG. 9A, a stadium view application 900 may display a 3D rendering 910 of a patient on a patient table, and a plurality of robotic arms docked to the patient. A perspective guide 920 may additionally be displayed to indicate what view of the 3D rendering is currently being displayed (e.g., perspective view, plan view, etc.). Furthermore, as shown in, for example, FIG. 9C, at least some of the robotic arms may be numerically labeled, so as to distinguish between different robotic arms (e.g., help enable better communication regarding the status of a particular arm). In another view within a stadium view application 900, additional information regarding status of the robotic system (e.g., what kinds of tools are attached to respective robotic arms, activation state of tools, etc.) may additionally be displayed proximate a rendering 910.

Figure 9B:
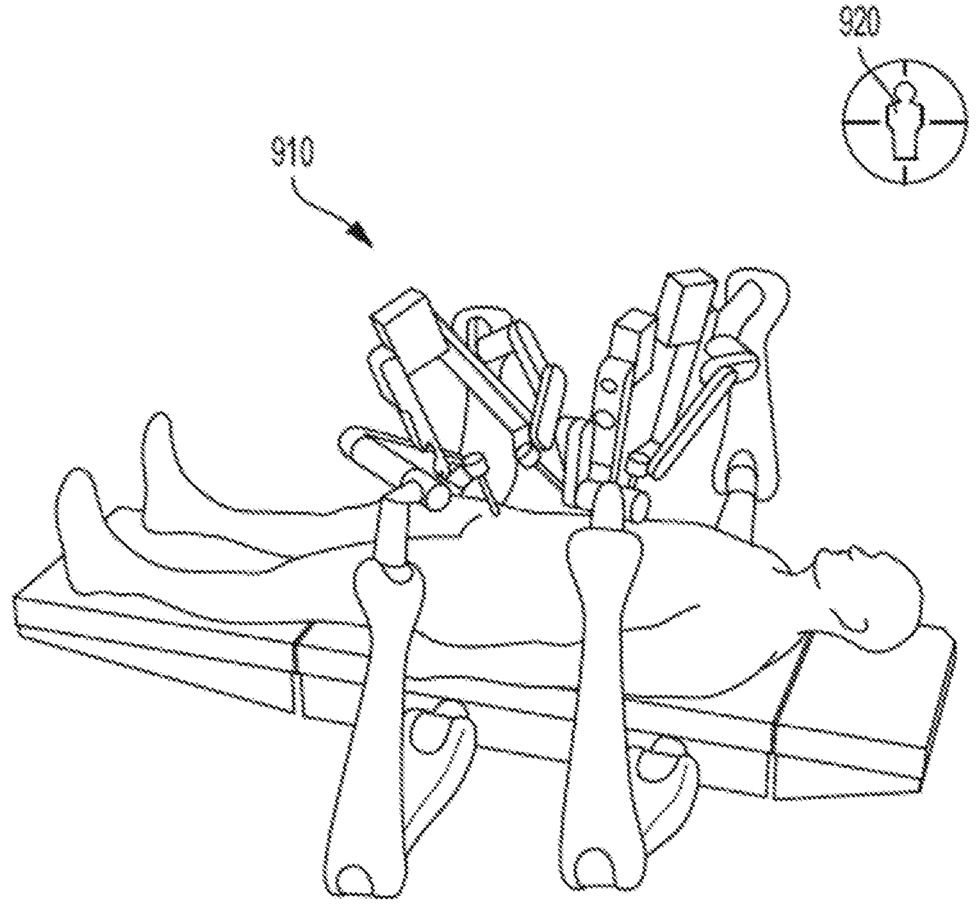
Figure 9C:
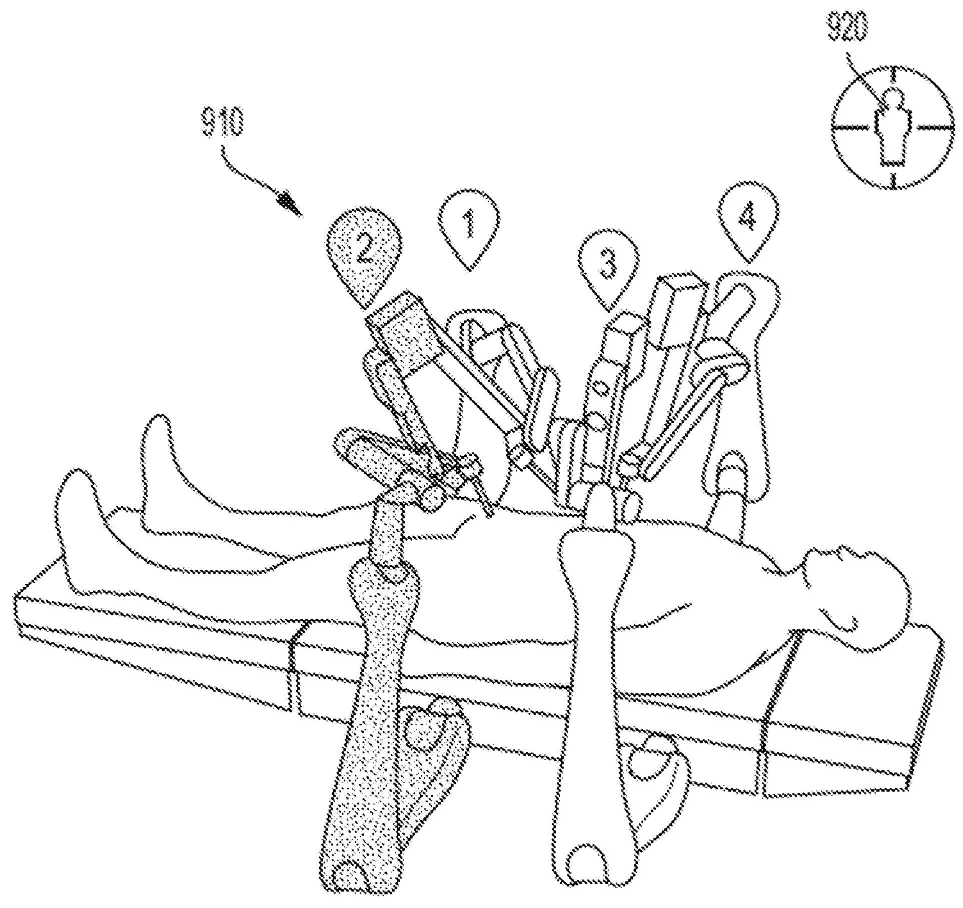

The display of the 3D rendering 910 in the stadium view application may be modified based on status of the rendered objects. For example, as shown in FIG. 9B, the rendering 910 is generally a nominal rendering, with no particular portions of the rendering 910 selected or highlighted. As shown in FIG. 9C, the stadium view application may be configured to highlight at least one of the robotic arms (labeled "2" in FIG. 9C), such as in response to a user selection of the arm. For example, a user may select a particular robotic arm and in response, the stadium view application may display information regarding status of the selected arm. As shown in, for example, FIG. 9E, in response to a user selection of an arm, the stadium view application may also display and/or highlight information relating to the selected arm and its associated tool, such as tool type (e.g., "scissors"), tool status (e.g., operation state such as "cut" or "coagulate", and/or staples remaining, etc.) and the like. As another example, a user may select a particular robotic arm such that it is highlighted in both the user's displayed GUI and in another displayed instance of the GUI (e.g., on a control tower display) to more easily communicate with other surgical staff regarding that robotic arm, thereby reducing confusion.

As another example, a user may select a robotic arm rendered in the stadium view application and move it (e.g., through a click-and-drag interaction) to effect a change in the position (pose) of the actual selected robotic arm. The movement of the selected rendered robotic arm may, for example, be communicated to a robotic arm controller that resolves the new position into a series of one or more actuator commands to actuated joints in the robotic arm such that the robotic arm position matches the new position of the rendered robotic arm. Accordingly, the stadium view application may provide a way to help enable a user in a user console "manually" reposition a robotic arm from the user console, without physically contacting the robotic arm. Similarly, the position of the patient table may be adjusted via adjustment of the rendered patient table within the stadium view app.

As another example, the rendered display of one or more portions of the robotic system may be modified to help guide a surgical team during setup and/or teardown (e.g., pre-operative and/or post-operative procedures) of the robotic surgical system. For example, a particular robotic arm may be highlighted in the stadium view application during setup of the robotic system to indicate that the next tool according to the procedure template application (described above) should be attached to that particular robotic arm. Other guidance, such as text descriptions and/or other graphical representations of tools and animations, etc., may be provided via the stadium view app to further help surgical staff set up, teardown, or otherwise tend to the system.

Figure 9D:
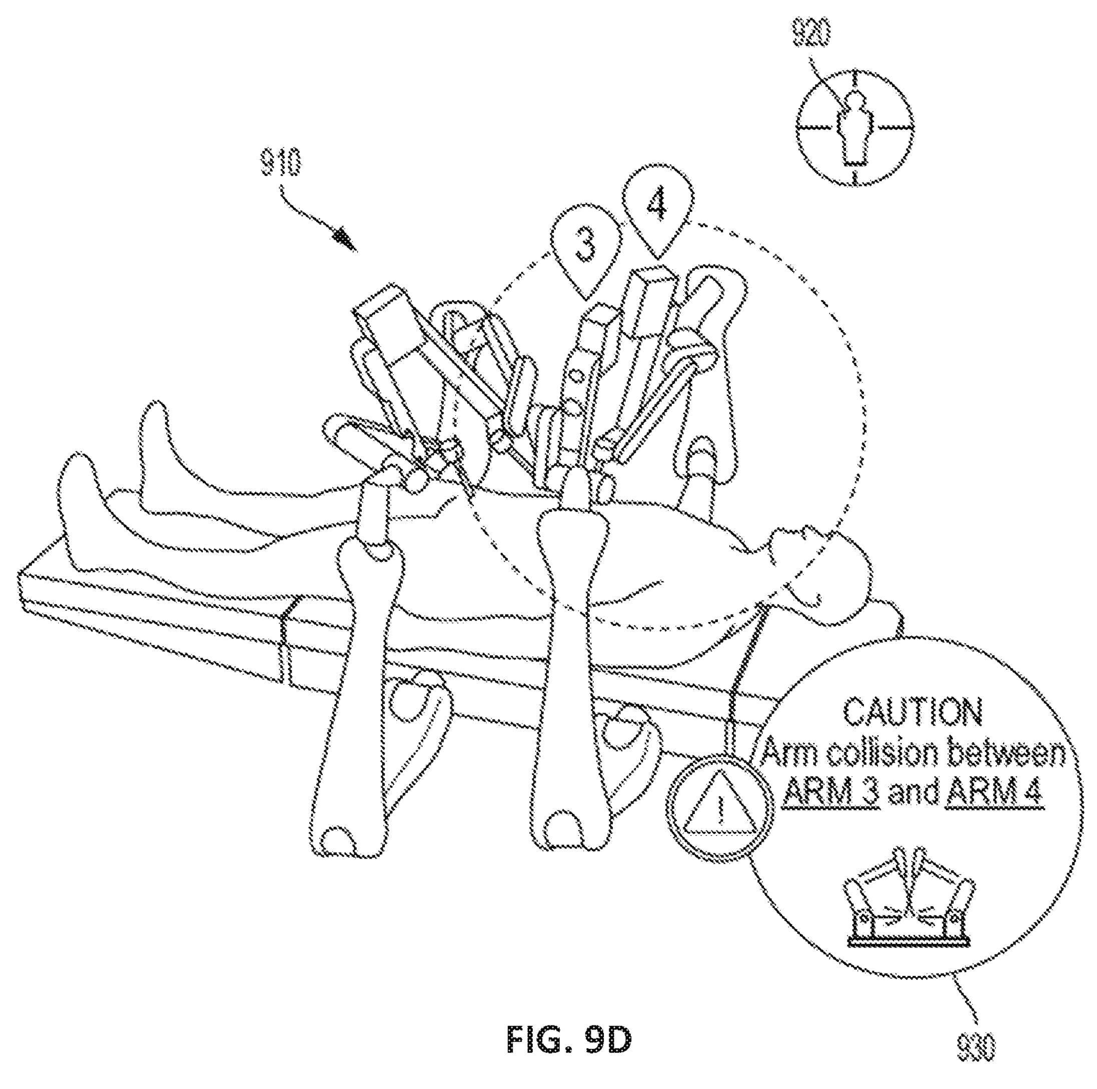
Figure 9E:
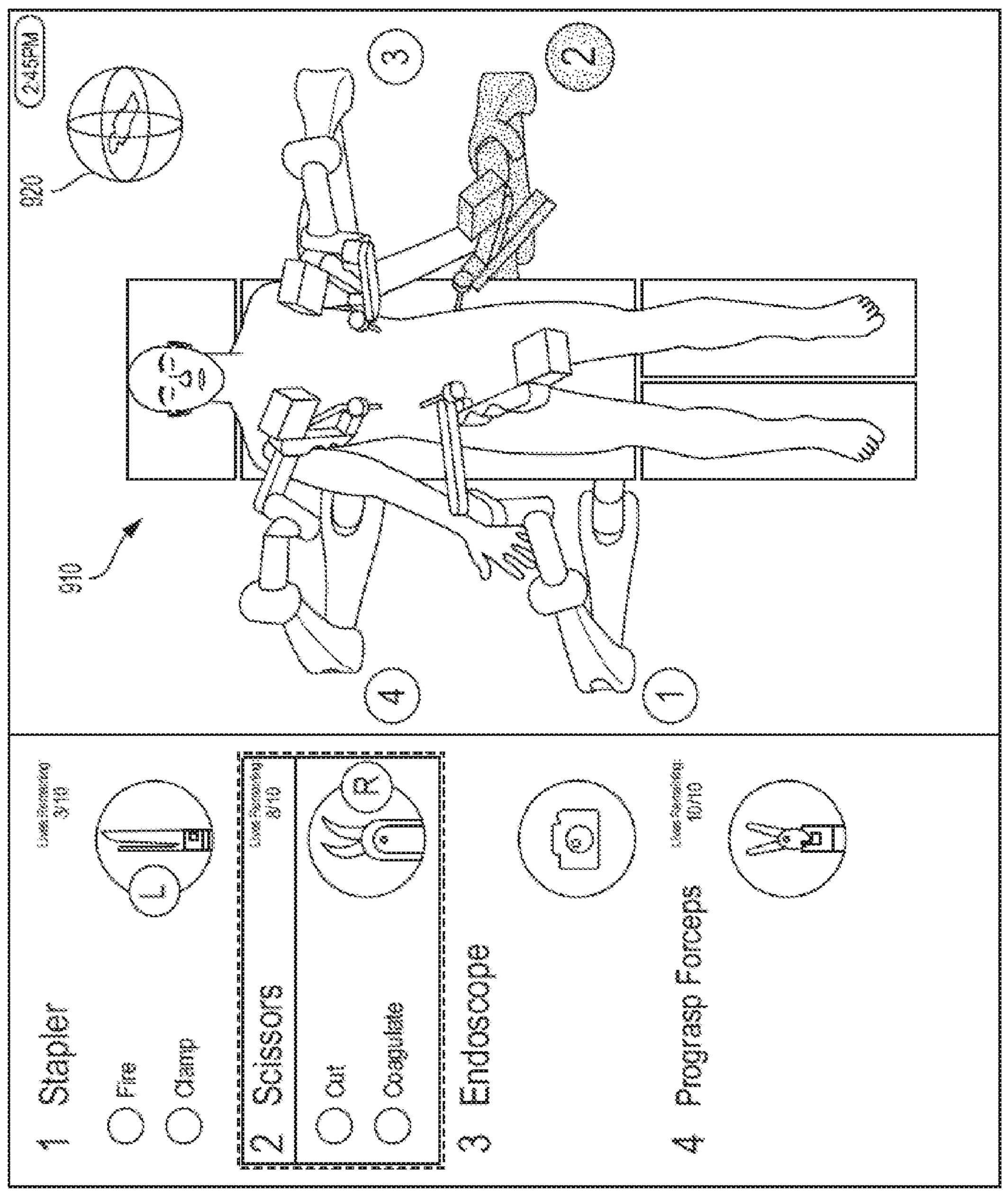

In some variations, the stadium view application may be configured to notify a user of a collision between robotic arms. In some variations, a collision (e.g., impending or occurred) may be detected based on proximity or contact sensors on robotic arms, machine vision techniques, and/or in any suitable manner. In response to receiving information indicating that a collision is impending or has occurred, the stadium view application may highlight one or more robotic arms involved in the collision. For example, as shown in FIG. 9D, one or more rendered robotic arms (labeled "3" and "4") may be highlighted. Additionally or alternatively, an alert notification 930 may be displayed explaining the collision. Audio alerts indicating a collision may additionally be provided to the user through the stadium view application. It should be understood that in other variations, the stadium view application may provide alerts or notifications for other kinds of status updates, such as surgical instrument errors, in a similar manner. For example, the rendered display of other portions of the robotic system, and/or other suitable portions of the operating room environment, may be highlighted to indicate other kinds of status changes or provide suitable updates. Notifications similar to alert notification 930 for other kinds of status updates may also be provided via the stadium view application.

Teleconferencing Application

One variation of an application for a GUI is a teleconferencing application that may enable a user to contact a colleague or other contact before, during, and/or after a surgical procedure. For example, the teleconferencing application may enable communication over a cellular network, a wired or wireless internet network (e.g., over WiFi), a direct line network connection, or in any suitable manner. In some variations, the teleconferencing application may store contact information including but not limited to name, picture, role or title, location, phone number or other contact, and the like. Through the teleconference application, a user may, for example, seek consultation with a contact for advice or other telementoring, or seek any other suitable kind of collaboration for a surgical procedure. The teleconferencing application may facilitate audio and/or visual collaboration, such as with telephone and/or video conferencing, and/or screen sharing.

One exemplary implementation of a teleconferencing application is shown in FIG. 5D in panel 510*h*. As shown in FIG. 5D, the teleconferencing application may display one or more icons associated with at least one contact, such as a thumbnail view of the person along with a name label.

Telestration Application

Another variation of an application for a GUI is a telestration application that may enable one or more users to annotate a displayed image or other aspect of the GUI. For example, a telestration application may display a palette of one or more annotation tools. The annotation tools may be used to mark up or label a displayed image such as an endoscopic image, and the annotated image may then be shared between collaborators (e.g., among different GUIs simultaneously displayed on different displays), saved for reference or future analysis, etc. For example, an annotated image may be used to more clearly communicate with a collaborator the location of lesion margins, nearby lymph nodes, and/or other critical anatomical structures (e.g., anatomical targets, tissue to avoid), etc. Collaborators may be among the same surgical team or in the same operating room, and/or may be external to the operating room (e.g., remote collaborators, such as a teleconferencing mentor).

One example of an annotation tool is a drawing tool, such as a pen or pencil tool with selectable width, color, line type, etc. Another example of an annotation tool is an erase tool, which may "undo" or erase markings of the drawing tool. As another example, an annotation tool may enable text labeling. Text labeling may be typed or dictated entries, and/or may include pre-determined template labeling (e.g., "Cut #1"). Annotation tools may be controlled, for example, with a user input device using gestures as further described below. When using an annotation tool, a graphical representation of the annotation tool may replace a cursor that is controlled by the user input device. For example, when a user is operating a drawing tool, the cursor may be a graphical representation of a pen or pencil.

Figure 10A:
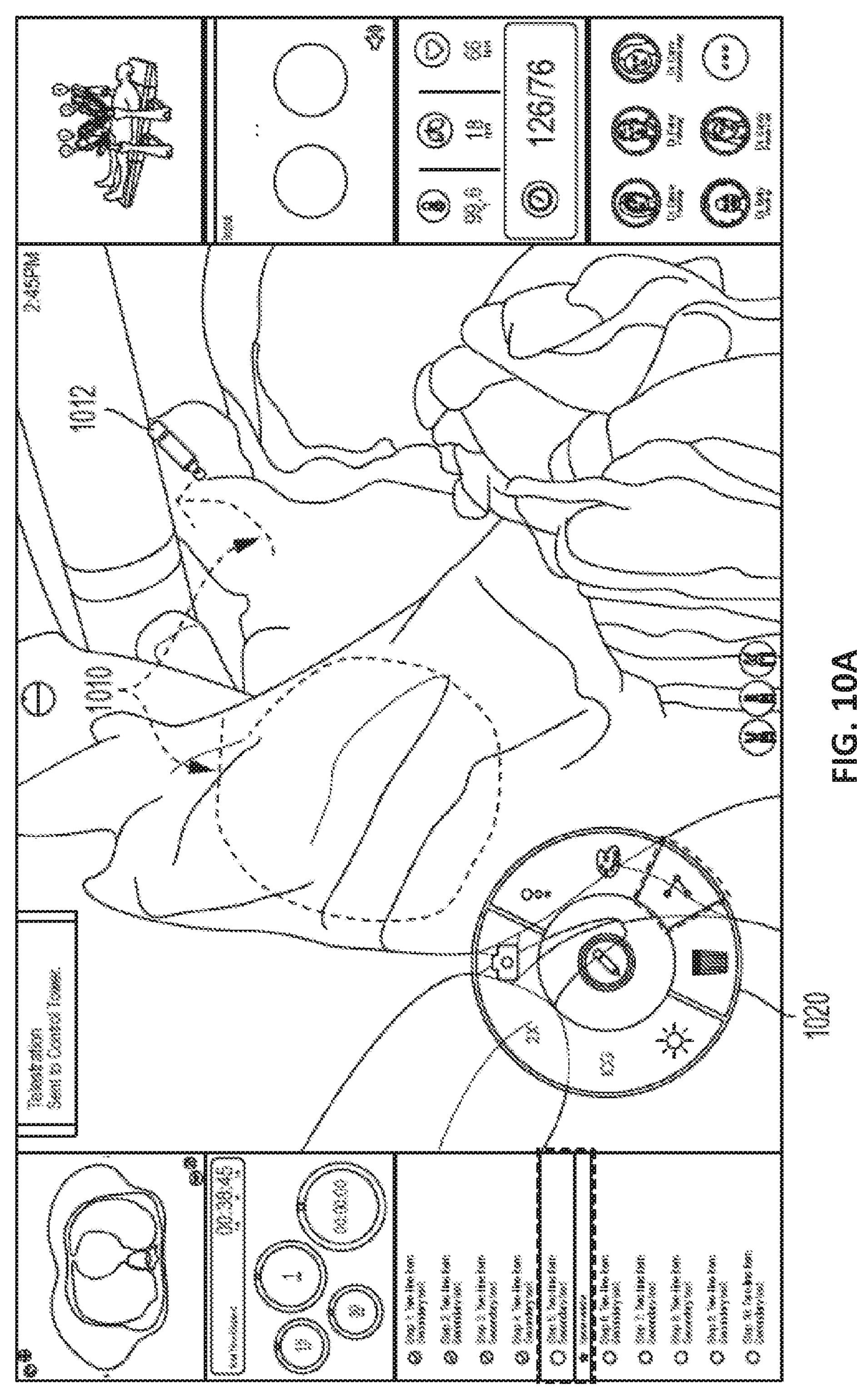
FIGS. 10A and 10B are exemplary variations of a GUI including a telestration application.
Figure 10B:
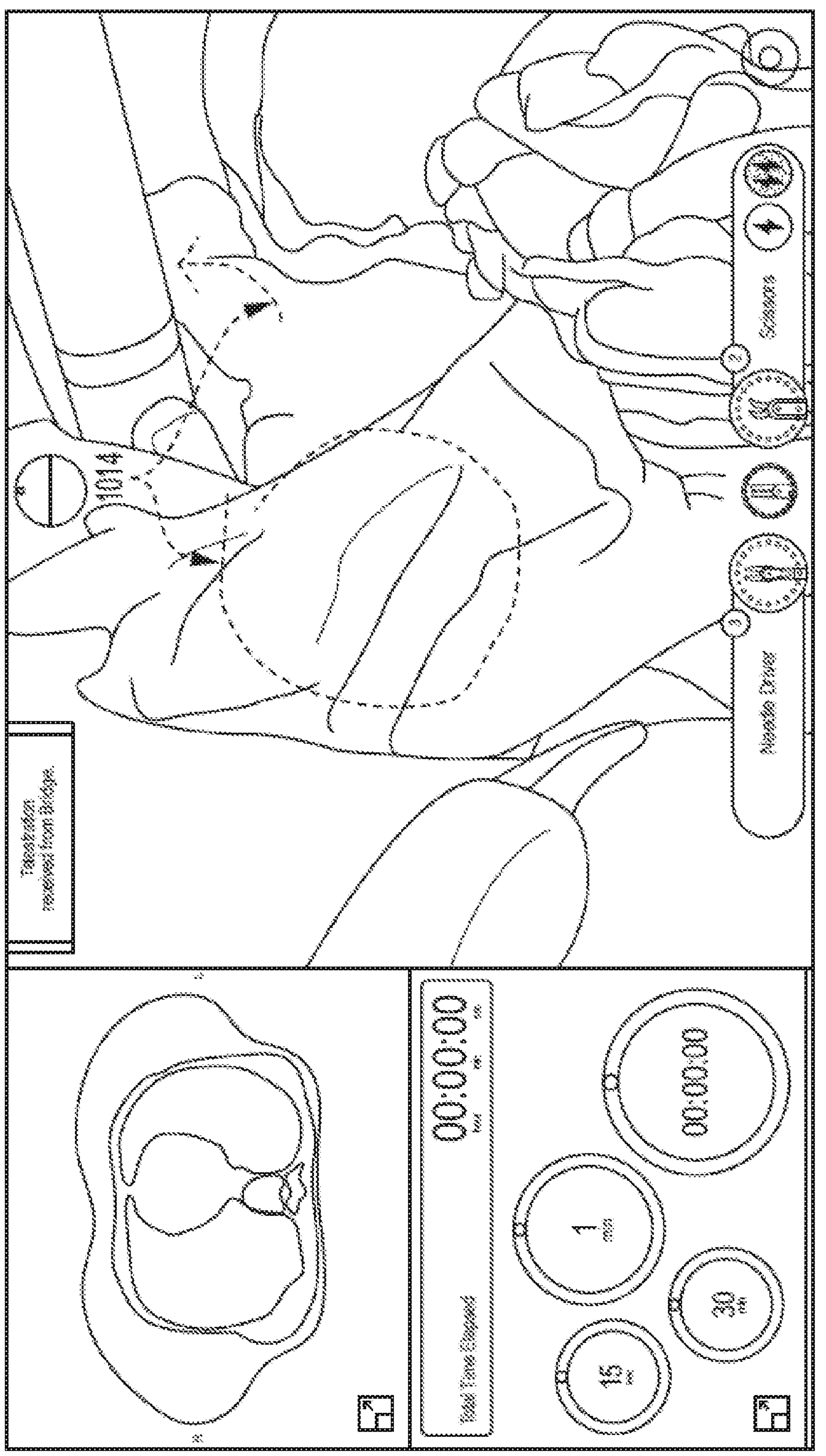

An exemplary implementation of a telestration application is shown in FIG. 10A. As shown in FIG. 10A, a user (such as a surgeon at a user console) may mark up an endoscopic image with annotations using a drawing tool (with a cursor 1012). For example, an annotation 1010 is a circle drawn around a portion of tissue to identify a region of tissue. As another example, an annotation 1012 is an arrow indicating a direction that the tissue identified in 1010 may be retracted. The annotated image (telestration) may be sent to a second display that is displaying another instance of the GUI (e.g., at a control tower where the second display may be viewable by other members of the surgical team) to help communicate a surgical plan. As shown in FIG. 10B, the second display may display the telestration with the mirrored annotations 1014. Accordingly, the telestration application may provide visual tools to help facilitate real-time collaboration with others during the surgical procedure.

Video Labeling Application

Another variation of an application for a GUI is a video labeling application. In some variations, a video recording of a surgical procedure may be obtained, such as throughout a surgical procedure. The video labeling application may include annotation tools (e.g., similar to those described above for the telestration application) that may be used to annotate or otherwise label the recorded surgical procedure videos. For example, the video labeling application may help enable users to associate a surgical procedure video with a particular patient (e.g., annotate with patient name, medical record number, etc.), in order to enable future access to the video such as for post-operative review.

In some variations, annotation tools may be manually controlled, such as by enabling typed text, overlaid drawings, etc. In some variations, annotation may additionally or alternatively be automatic or semi-automatic, such as by automatically importing patient information and tagging the video with the imported information.

Figure 24:
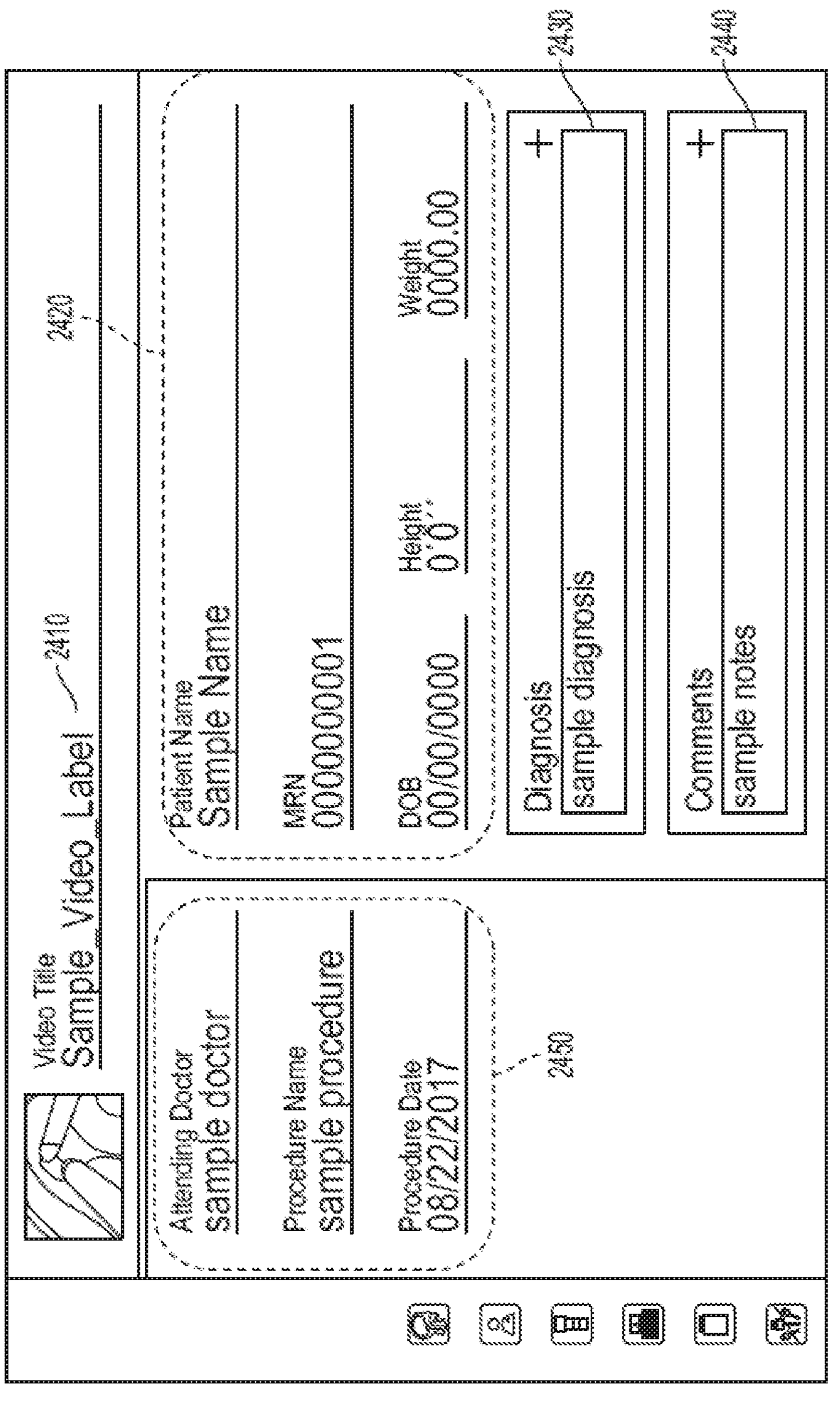
FIG. 24 is an exemplary variation of a GUI with a video labeling application.

FIG. 24 depicts an exemplary implementation of a video labeling application. The video labeling application 2400 may help enable a user to generate a video profile including video label 2410 (e.g., file name or the like), patient information 2420 (e.g., patient name, medical record number, date birth, height, weight, age, etc.), diagnostic information 2430, any notes or comments 2440 (e.g., relating to the video or the surgical procedure, etc.), surgical procedure information 2450 (e.g., name of surgeon and/or any other persons in the surgical team, name or type of surgical procedure performed and depicted in the video, surgical procedure date, etc.), name of person labeling the video, and/or other suitable information.

Video Player Application

One variation of an application for a GUI is a video player application. The video player application may, for example, be in communication with a video database such that the video player application may receive a video (or a pointer to a video) and display it on the GUI. The video player application may display, for example, an instructional or training video for a relevant surgical procedure or surgical task, or for other tasks relating to the surgical procedure (e.g., setup of ports for docking the robotic arms). In some variations, the video player application may be used by users to review videos in a pre-operative setting, such as to prepare for a surgical procedure. Additionally or alternatively, the video player application may be used to review videos in an intra-operative setting, such as to help resolve a complication that has arisen during the surgical procedure. However, other suitable videos may be played. Furthermore, it should be understood that variants of a video player application (e.g., a music player) may be provided via the GUI.

Simulator Application

Another variation of an application for a GUI is a simulator application. A simulator application may, for example, be in communication with a database storing simulated surgical robotic experiences or simulated exercises, such as to teach user-specific psychomotor skills for robotic simulation (e.g., games to practice performing a roll action of a handheld user input device and/or other skills, etc.). Simulated surgical robotic experiences may include, for example, simulation and training exercises with simulated patients. The simulator application may load such simulated experiences into the GUI, including a simulated endoscopic view and other patient parameters. The simulated experiences may further include simulated events such as robotic arm collisions, patient distress, and other suitable events that may help enable a new user (e.g., a surgeon in training) learn how to respond and resolve issues appropriately. Simulations may be generated separately from the simulator application, such as with simulation developer software, or alternatively may be generated within the simulator application itself.

In some variations, the simulator application may grade a user based on his or her performance in the simulated exercise, such as by providing a score for the user. Such scores may be tracked over time to gauge a trainee's progress and fluency in using the robotic surgical system. In some variations, the simulator application may display a user's progress throughout a set curriculum (e.g., indicating a user has completed three out of ten exercises), evaluate baseline skills of the user to tailor or adjust curriculum, and/or provide recommendations for particular simulation exercises based on the user's performance.

Ergonomic Settings Application

Another variation of an application for a GUI is an ergonomic settings application, which may, for example, be implemented in a GUI displayed at a user console with adjustable ergonomic settings. Exemplary variations of a user console with adjustable ergonomic settings are described in further detail U.S. patent application Ser. No. 15/712,052 titled "USER CONSOLE SYSTEM FOR ROBOTIC SURGERY" filed on Sep. 21, 2017, which is incorporated herein in its entirety as referenced above. The ergonomic settings application may provide an interface for a user to adjust various settings of a user console, such as seat height, seat angle, foot pedal tray angle, etc. For example, individual ergonomic settings of the user console may be manually adjusted and communicated to a user console controller to effect adjustment of those settings in the user console.

Additionally or alternatively, in another example, an ergonomic settings application may receive a user input of user information in order to recall or generate suitable ergonomic settings in the user console for the user. For example, user information may include user login that is associated with a seating profile with one or more stored ergonomic settings, where the seating profile may be recalled from a user database. As another example, an ergonomic settings application may enable a user to provide his or her anthropometric information (e.g., height, sex or gender, etc.) to automatically generate suitable ergonomic settings for the user. Similar to that described above, ergonomic settings of the user console may subsequently be communicated to a user console controller to implement the ergonomic settings in the user console.

Generator Application

In some variations, a GUI may include a generator application, which may enable control of one or more settings of a surgical instrument. For example, a GUI including a generator application at a user console may enable a surgeon sitting at the user console to control settings of a surgical instrument directly. In some situations, this may increase overall efficiency of the surgical procedure, as a surgeon at the user console may avoid having to ask another member of the surgical staff to change settings.

Figure 19:
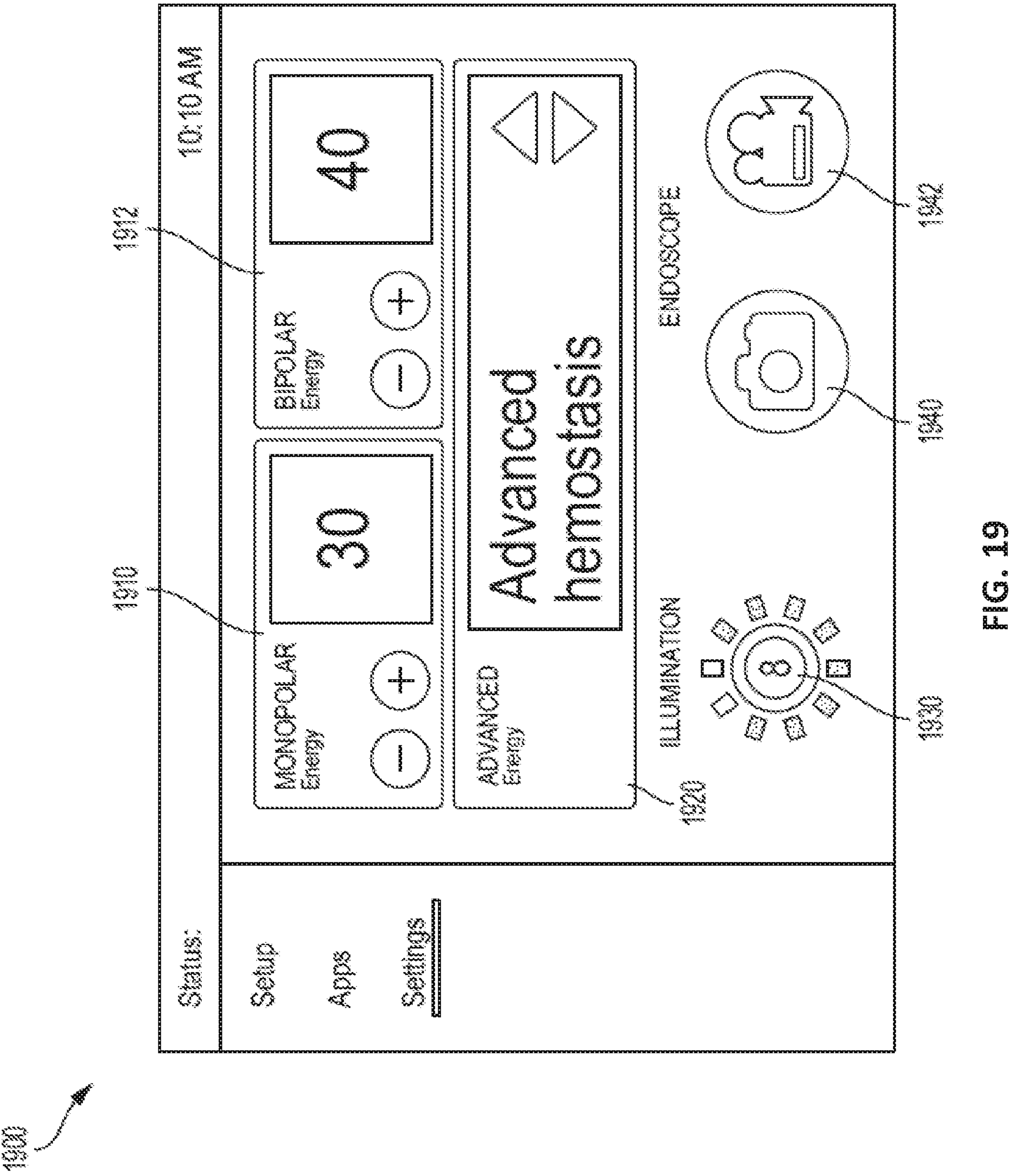

A generator application may, for example, display one or more interactive controls for adjusting energy settings of a surgical instrument. For example, as shown in FIG. 19, a generator application 1900 may include an interactive control 1910 for decreasing and increasing monopolar energy level of an electrosurgical cutting instrument, an interactive control 1912 for decreasing and increasing bipolar energy level of an electrosurgical cutting instrument. Advanced settings control 1920 may provide more specialized adjustments (e.g., to indicate an "advanced hemostasis" setting). As another example, a generator application may include an illumination control 1930 to adjust an illumination level of a surgical instrument providing a light source. Furthermore, a generator application may display one or more interactive controls to adjusting any suitable setting of a surgical instrument. For example, a generator application may include settings 1940 and/or 1942 that may be selected to toggle between a static image capture mode and a video capture mode for an endoscopic camera.

Tool Widgets

In some variations, a GUI may furthermore display one or more tool widgets configured to communicate information regarding surgical instruments in a convenient, efficient manner. For example, tool widgets may summarize high-priority information such as tool type, tool state, tool settings, and/or tool "lives" remaining (e.g., number of firings left in a cartridge, etc.). Tool widgets may be overlaid over an endoscopic image, adjacent or proximate the endoscopic image, and/or or in any other suitable portion of the displayed GUI. Exemplary illustrative variations of tool widgets are described in further detail below.

Tool Kit

Figures 11A, 11B:
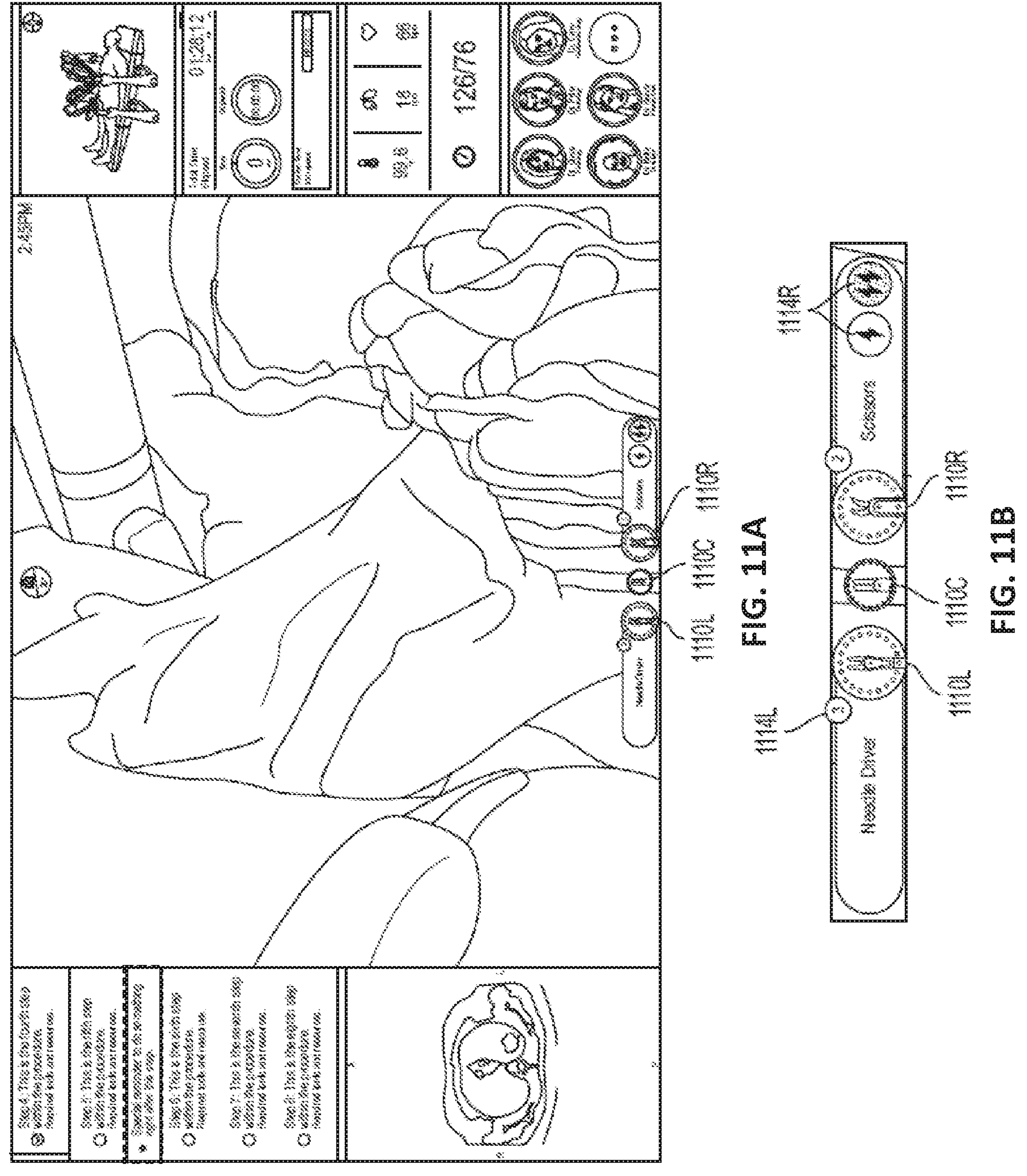
FIGS. 11A and 11B depict an exemplary variation of a GUI with docked tool widgets.

In some variations, one or more tool widgets may be arranged in a "tool kit" or tool bar that is docked at a fixed location in the GUI. The tool kit may provide a summary of tool (instrument) status. For example, as shown in FIG. 11A, a tool kit may include at least one tool widget (e.g., a left-side tool widget 1110L corresponding to a surgical instrument controlled by a left hand controller, and a right-side tool widget 1110R corresponding to a surgical instrument controlled by a right hand controller) may typically be displayed and overlaid over an endoscopic image. A tool kit may further include one or more additional tool widgets such as tool widget 1112C corresponding to other "backup" surgical instruments (e.g., instruments located off-screen relative to the displayed endoscopic image) that are readily available for control.

Figure 25:
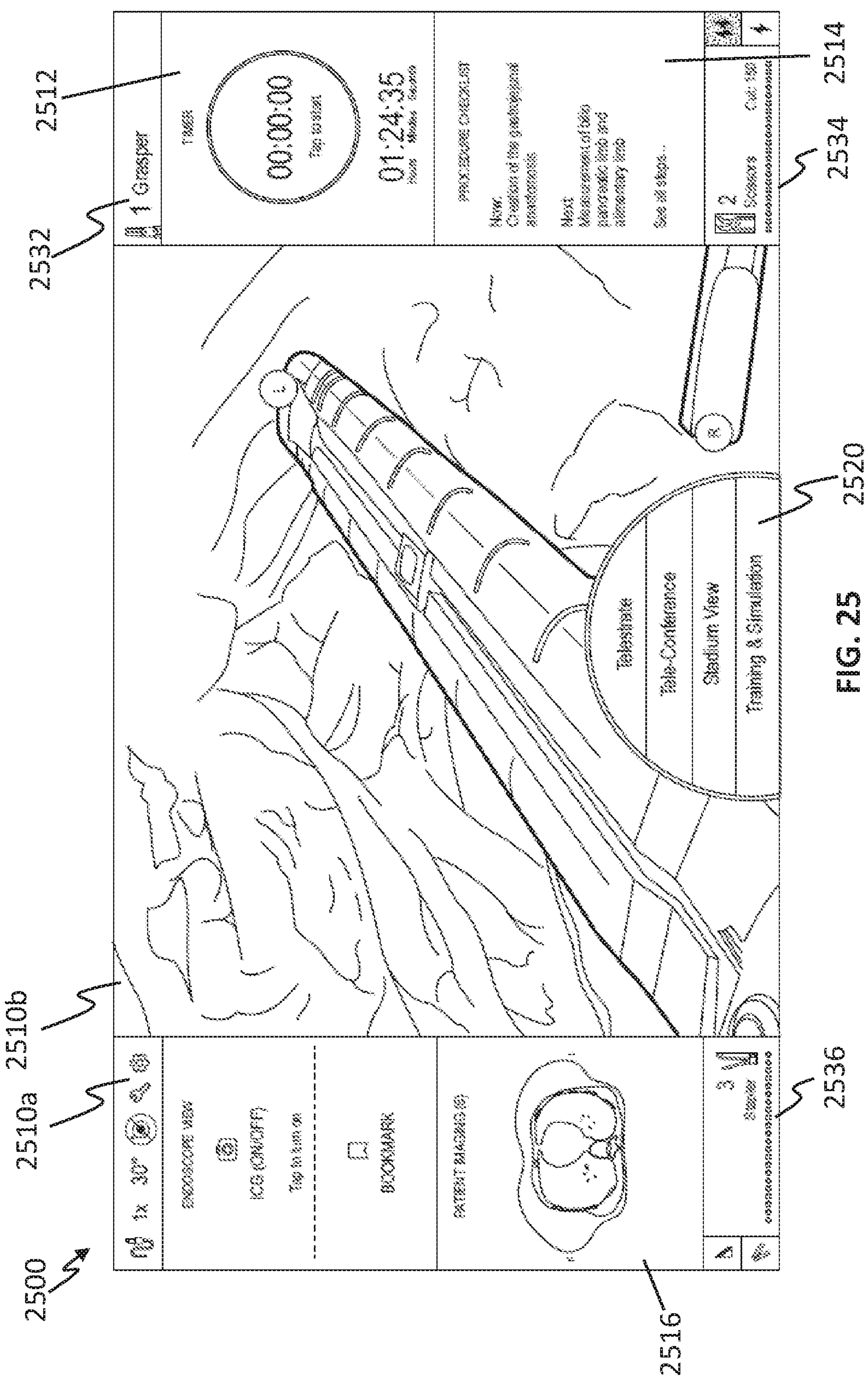
FIG. 25 is an exemplary variation of a GUI including sidebar panels.

The tool kit shown in FIG. 11A is displayed along a bottom edge of the display, although in other variations the tool kit may additionally or alternatively be displayed in any suitable location. For example, as shown in FIG. 25, the tool kit may include tool widgets 2532, 2534, and 2536 displayed on side bars of the display and corresponding to a first "backup" surgical instrument located off-screen, a second surgical instrument controlled by a right-hand controller, and a third surgical instrument controlled by a left-hand controller, respectively. The tool widget 2532, corresponding to the first "backup" surgical instrument, is displayed in an upper corner of a side bar, relatively out-of-sight. The tool widgets 2534 and 2536, corresponding to controlled second and third surgical instruments, are displayed in lower corners of right and left side bars, respectively.

While in some instances tool widgets may be generally opaque to improve visibility of the content of the tool widgets, one or more of the tool widgets may become translucent or hidden if otherwise the tool widget risks obscuring an important portion of the image. For example, the GUI may render a tool widget accordingly in response to a user input instructing that the tool widget be translucent or hidden. As another example, the GUI may render a tool widget translucent or hidden if, for example, one or more eye-tracking sensors or head-tracking sensors detect that a user is attempting to look at an image behind a tool widget. In some variations, at least a portion of the tool kit (or its equivalent tool information) may be rendered adjacent or proximate to an endoscopic image instead of being overlaid over the endoscopic image, such as to improve viewability of the entire endoscopic image without obstruction.

A tool kit may provide information relating to a tool status, such as tool type, energy levels, status, etc. For example, as shown in FIG. 11B, a left-hand tool widget 1110L may include a graphical representation of an instrument to indicate the type of surgical instrument (e.g., scissors, stapler, etc.) that is being controlled by a left-hand controller. Next to the left-hand tool widget 1110L, the tool kit may also include a text label ("Scissors—Monopolar, curved") that may explicitly describe the type of surgical instrument associated with the left-hand tool widget 1110L, as well as one or more tool status icons 1114L that may indicate additional tool information status, such as energy generator levels. In some variations, the tool kit may enable modification of tool status, such as adjustment of energy generator levels of a surgical instrument (e.g., display of one or more buttons or dials for increasing or decreasing energy generator levels). In some variations, the text label and the tool status icons 1114L may be visually grouped together with the left-hand tool widget 1110L, so as to form an extension of the left-hand tool widget 1110L, though alternatively these display components associated with the left-hand tool may be discrete. Similarly, as shown in FIG. 11B, a right-hand tool widget 1110R may include a graphical representation of an instrument to indicate the type of surgical instrument that is associated with the right-hand tool widget 1110R, and the tool kit may further include a text label and/or one or more tool status icons 1114R that may indicate additional tool information status.

Generally, any of the components of a tool kit may vary in appearance based on activities or status of its associated surgical instruments. For example, with reference to FIG. 11B, the graphical representation of the instrument in the tool widget 1110R may change in appearance according to a current operational state of the associated instrument. As another example, the color of any of the components of a tool kit may change depending on a current operational state of the associated instrument. Furthermore, in some variations, the GUI may include one or more animations in or proximate a tool kit in accordance with a current operational state of the associated instrument.

Figure 12:
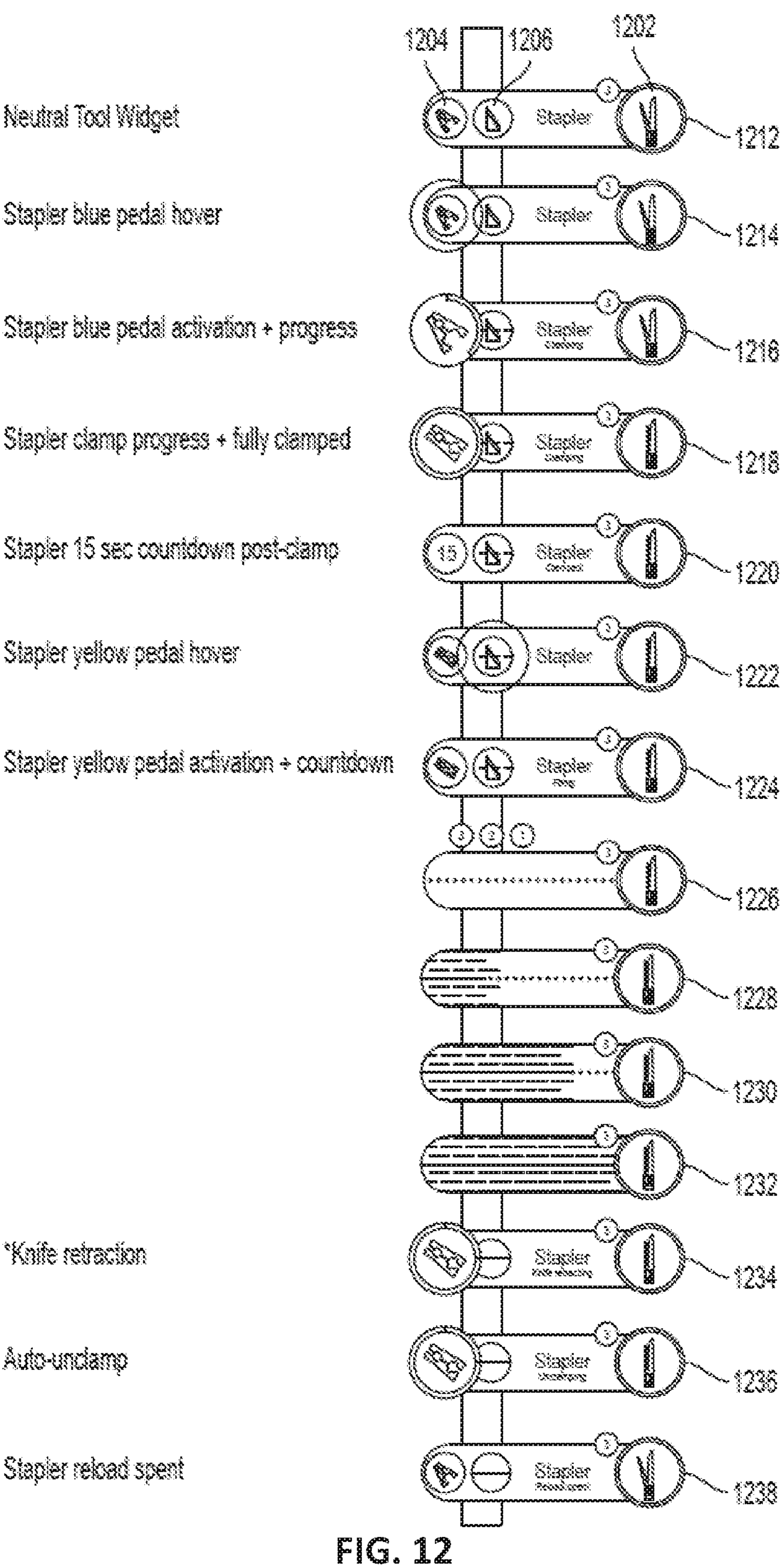
FIG. 12 is a schematic illustration of an exemplary variation of a tool widget workflow for illustrating operational status of a surgical instrument in a GUI.

In some variations, a tool kit may generally vary in appearance in accordance with a predetermined scheme or workflow for the tool widgets. One exemplary variation of a tool widget workflow is illustrated in FIG. 12 for a stapler instrument. For example, a tool kit for display in a GUI may include a tool widget 1202 including a graphical representation of a stapler, a text description of the stapler, a clamp icon 1204 configured to illustrate a clamping state of the stapler, and a fire icon 1206 configured to illustrate a firing state of the stapler. In some variations, the text description, clamp icon 1204, and fire icon 1206 may be visually grouped together with the tool widget 1202 so as to form an extension of the tool widget 1202.

In step 1212 of the tool widget workflow, the stapler is in a neutral state in that none of its functionalities are being activated. Thus, the tool kit is also in a neutral state, with the tool widget 1202 having a graphical representation of a stapler that is open (i.e., unclamped), and the clamp icon 1204 and the fire icon 1206 being in an inactive state (e.g., dimmed in display).

In step 1214 of the tool widget workflow, a user is hovering his or her foot over a foot pedal control configured to actuate a clamping state of the stapler. The user's foot may, for example, be in contact with the foot pedal (or just above it) but not fully depressing the foot pedal, and this hovering state may be detected by one or more sensors, such as an angle sensor in the foot pedal. Upon detection of the user's hovering foot, the clamp icon 1204 may grow a "halo" effect. The "halo" effect may be translucent or transparent, and/or may pulse in animation to indicate a state of clamping readiness.

In step 1216 of the tool widget workflow, the user has depressed and engaged the foot pedal control, thereby activating a clamping state of the stapler. The "halo" effect on the clamp icon 1204 may be replaced by a progress bar that "fills" to indicate elapsed time and anticipated remaining time for the clamping action. Furthermore, clamp icon 1204 may become enlarged to draw attention to clamping state of the stapler. The tool widget may additionally or alternatively include a subtext ("clamping") to explicitly indicate the current action is in progress.

In step 1218 of the tool widget workflow, the stapler has successfully completed the clamping action. A graphical icon in the clamp icon 1204 may change accordingly to mimic a clamped mechanism (e.g., a closed clothespin). Additionally, the graphical representation of a stapler in the tool widget 1202 may also mimic a clamped stapler mechanism (e.g., with stapler arms closed).

In step 1220 of the tool widget workflow, a countdown timer is displayed over the clamp icon 1204. For example, a countdown timer of 15 seconds (or any suitable period of time) may indicate when 15 seconds have elapsed and the success of the clamping action may be assessed. Once 15 seconds have elapsed, the subtext in the tool kit may indicate a successful "clamped" state of the stapler. Additionally or alternatively, the fire icon 1206 may change color and/or size to indicate a preparedness for the firing step of the stapler.

In step 1222 of the tool widget workflow, the user is again hovering their foot over the foot pedal (e.g., in a similar manner as in step 1214 described above). Upon detection of the user's hovering foot over the foot pedal (and with the known, successful "clamped" state of the stapler), the fire icon 1206 may grow a "halo" effect that is translucent or transparent, and/or may pulse in animation to indicate a state of the stapler firing readiness.

In step 1224 of the tool widget workflow, the user has depressed and engaged the foot pedal control, thereby activating a firing state of the stapler. The "halo" effect on the fire icon 1206 may cease, and the entire tool widget may change color to indicate that the stapler has begun firing.

In steps 1226-1232 of the tool widget workflow, the entire tool widget may change color. For example, the tool widget may be colored to match a stapler cartridge color (e.g., corresponding to the size of the staples in the stapler cartridge). A countdown timer (e.g., 3 seconds), beginning from pedal activation in step 1224, may be displayed on or near the tool widget to indicate progress of the stapling. Additionally or alternatively, a progress indicator, such as an animated progress bar, may travel across the tool widget to indicate progress of the stapling. For example, steps 1226-1232 indicate a progress bar animation traveling progressively across the length of the tool widget as the countdown progresses.

In step 1234 of the tool widget workflow, the firing stage has completed and the knife of the stapler (previously used to cut tissue as part of the stapling process) is being retracted. The fire icon 1206 may be dim, blank, or otherwise have a change in appearance to indicate a "spent" state. Additionally or alternatively, the subtext ("knife retracting") of the tool widget may explicitly indicate the current state.

In step 1236 of the tool widget workflow, the tissue may begin to be unclamped and released. The clamp icon 1204 may include a progress bar that "unfills" (e.g., in the opposite direction as in step 1216 during clamping) to indicate elapsed time and anticipated remaining time for the unclamping action. Furthermore, the clamp icon 1204 may become enlarged to draw attention to the unclamping state of the stapler. The tool widget may additionally or alternatively include a subtext ("unclamping") to explicitly indicate the current action is in progress. Unclamping may, in some variations, be automatically performed following completion of stapler firing.

Finally, in step 1238 of the tool widget workflow, the tissue has completed unclamping and the stapler cartridge is fully spent (empty). The graphical representation of a stapler on the tool widget 1202 may be depicted as open (e.g., stapler arms apart). The clamp icon 1204 is depicted as an open clamp mechanism (e.g., open clothespin), and the fire icon 1206 remains in a state that indicates a "spent" state.

It should be understood that FIG. 12 is an exemplary tool widget workflow described and shown for illustrative purposes only, and that a tool widget may have any other suitable kind of display changes as part of its workflow, depending on desired interactive behavior between a user and the tool widget, depending on the type of surgical instrument, etc. Additionally or alternatively, other forms of notification throughout the workflow, such as audio-based status updates of a surgical instrument operation (e.g., verbal descriptions, beeps or tones, etc.), may be provided to users.

Figure 13:
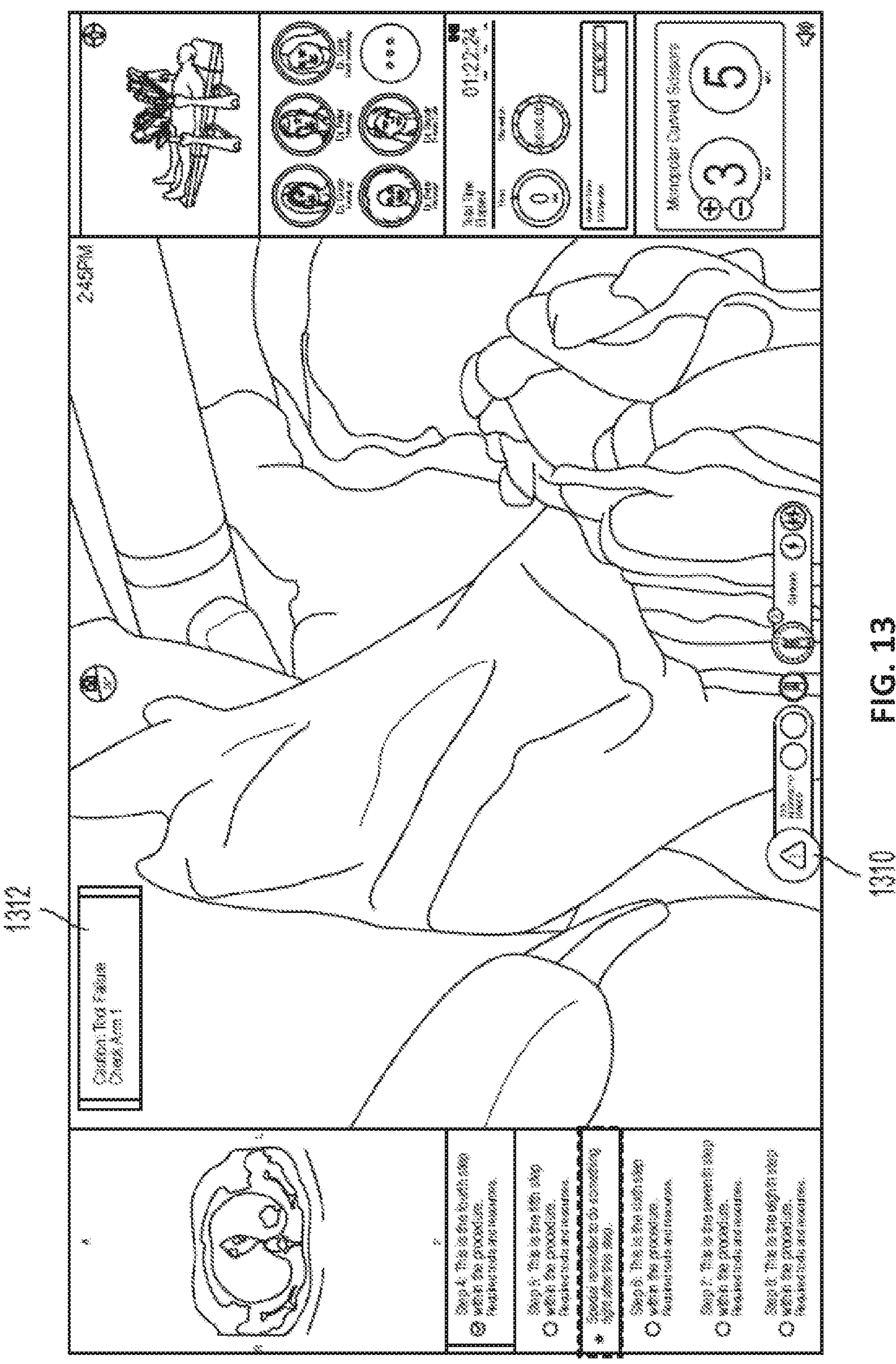
FIG. 13 is an exemplary variation of a GUI with tool notifications.

In some variations, a tool widget may display an alert or a notification in response to the detection of a trigger event occurring during a workflow. For example, as shown in FIG. 13, in the event that one or more sensors (e.g., on a tool driver) detects that an instrument is incorrectly loaded, an associated tool widget may display a text notification 1310 indicating the problem to a user. Additionally, a separate notification 1312 may be displayed elsewhere on the display. The separate notification 1312 may, for example, include additional (e.g., more detailed) information relating to the trigger event that is not displayed in the tool widget. Other examples of trigger events may include exhaustion of "lives" of an instrument (e.g., out of a predetermined number of fires of a stapler), an instrument jamming, or other instrument malfunction. Any suitable trigger event for prompting an alert of a notification may be defined. In some variations, alerts or notifications may be prioritized for display in order of urgency.

Floating Tool Widgets

In some situations, it may be impractical for a user to look away from where surgical instruments are depicted in an endoscopic image, because the user may desire to maintain eye focus on what the instruments are doing to tissue, etc. In such situations, one or more "floating" tool widgets may be overlaid over an endoscopic image near the surgical instruments as shown in the endoscopic image. By positioning the tool widget on or near the surgical instrument, a user may view status information relating to the surgical instrument while maintaining focus on the surgical instrument in the endoscopic image, and may avoid having to look toward a tool kit that may be docked in an inconvenient location in the display. Accordingly, such floating tool widgets in some variations of the GUI may help enable a user to perform a surgical procedure more efficiently, more safely, and with more confidence.

In some variations, machine vision techniques may be used to determine the location of a surgical instrument in the endoscopic image, then the GUI may be configured to display a floating tool widget associated with that tool within a predetermined distance of that tool (e.g., overlaid over or near the instrument's distal end effector, overlaid over or near a distal end of the instrument shaft, etc.). As the surgical instrument is moved around, the floating tool widget may be "sticky" or follow the surgical instrument.

Figure 14:
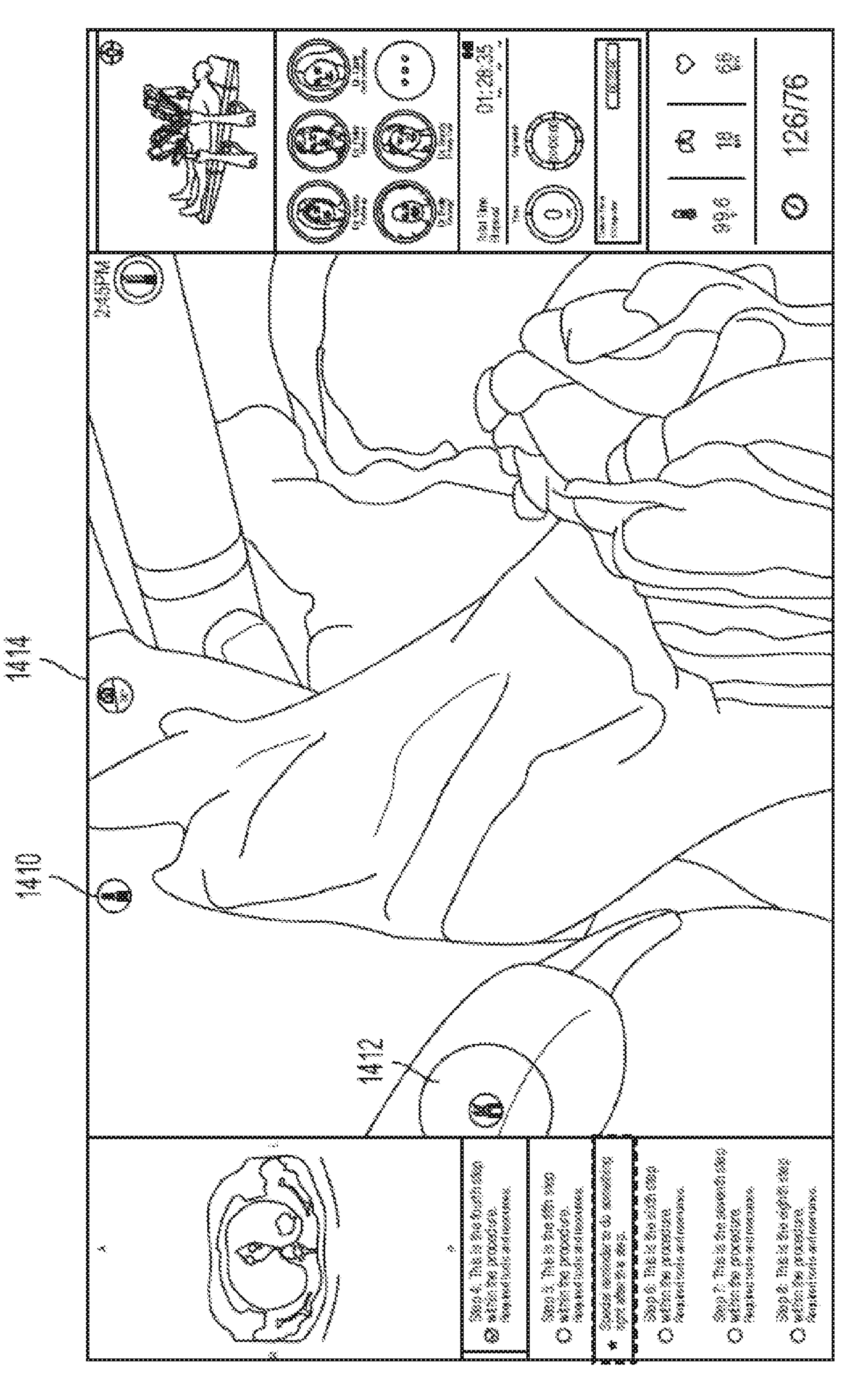
FIG. 14 is an exemplary variation of a GUI with floating tool widgets.

In other variations, a floating tool widget may be placed at other locations of the display, such as to indicate where other surgical instruments are located off-screen. For example, as shown in FIG. 14, a floating tool widget 1410 may be located at the top edge of the endoscopic image, indicating that if the endoscopic image were to pan upwards, another surgical instrument may become visible. As another example, a floating tool widget relating to an endoscopic camera providing a displayed endoscopic image may have an associated tool widget 1414 as shown in FIG. 14. In this example, floating tool widget 1414 may include a horizon line that may indicate the orientation of the endoscopic camera (e.g., relative to a 30-degree tip at the distal end of the endoscopic camera device, or any suitable range).

A floating tool widget may be substantially similar to those described above with respect to tool kits. For example, a floating tool widget may follow a tool widget workflow based on operational status of the surgical instrument, similar to that described with respect to FIG. 12. For example, as shown in FIG. 14, a floating tool widget 1412 may grow a "halo effect" with a particular color to indicate in shorthand a particular step in the tool widget workflow (e.g., blue halo to indicate that the user's foot is hovering above or resting on the blue pedal, yellow halo to indicate that the user's foot is hovering above or is resting on the yellow pedal, etc.).

Quick Access Menu

In some variations, a quick access menu may be activated and displayed to provide direct access to one or more functionalities of the GUI, such as a functionality of one or more applications. The quick access menu may, for example, reduce the amount of inadvertent and/or unnecessary movement of the user input device to engage certain functionalities of one or more applications. For example, a quick access menu may be displayed upon user request, such as in response to a particular combination of gestures detected on a user input device as described in further detail below. In one exemplary variation, the user selects options in the quick access menu by rolling and squeezing the user input device. This rolling movement may keep the user input device on the same axis as the tool end effector, thus allowing the user to more quickly clutch back into surgery (using the user input device to control surgical instruments) without having to realign the user input device to the tool end effectors.

Figure 15:
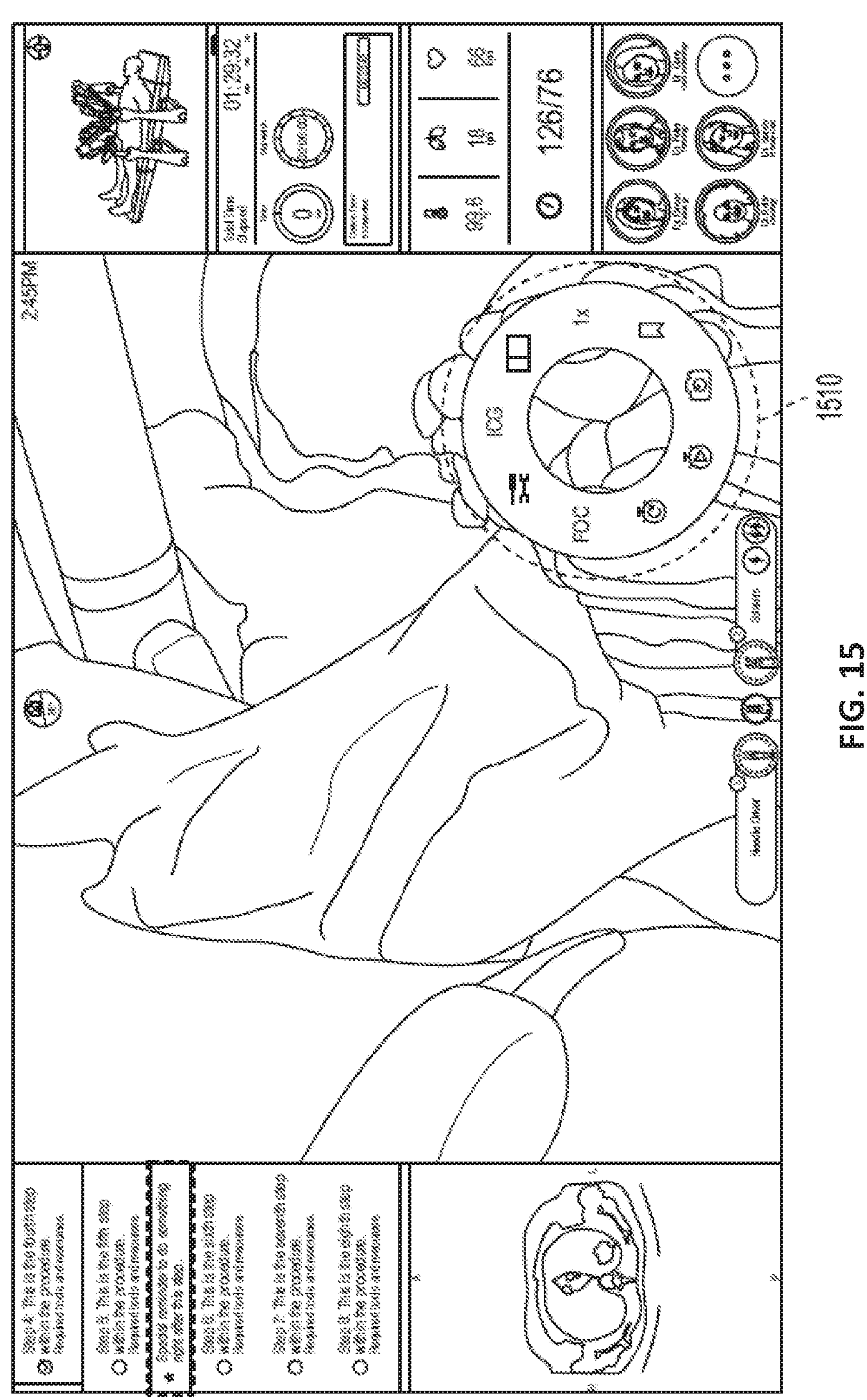
FIG. 15 is an exemplary variation of a GUI with a quick access menu.

Exemplary implementations of a quick access menu are shown in FIGS. 10A and 15, in which quick access menus 1020 and 1510, respectively, may include selectable icons arranged in a ring. At least some of the selectable icons may correspond to software applications of the GUI (e.g., telestration application, teleconference application, timer, etc.). At least some of the selectable icons may correspond to general GUI functionality, such as a "share" functionality that allows the user to share with another device the current display on one or more of the display panels, a "camera" functionality that takes a screenshot of the current display on one or more of the display panels. When a user selects an icon in the quick access menu, the user accesses a shortcut to the functionality associated with the selected icon.

The layout (e.g., content, shape, interactive form, etc.) of the quick access menu may be reconfigurable to be populated with any suitable combination of applications and/or general GUI functionalities. Similar to the panels in the multi-panel display, a user may customize the content of the quick access menu based on user input (e.g., drag and drop selections into the quick access menu). Furthermore, although FIGS. 10A and 15 depict a ring-shaped quick access menu, it should be understood that other suitable shapes and/or displayed location of a quick access menu may be implemented. For example, additionally or alternatively, a user may customize a form factor of the quick access menu (e.g., circular or ring-shaped, list such as the quick access menu 2520 variation shown in FIG. 25, rectangular or other grid of selectable icons or descriptors, drop-down list, or any suitable format). A quick access menu may be displayed in any suitable location on the display (e.g., an open display in the surgeon console). Furthermore, the quick access menu may be configured automatically based on previous effective layouts of the quick access menu for certain kinds of surgical procedures, certain kinds of users, etc.

Although particular variations of the GUI are depicted in the figures and described in accompanying description above, it should be understood that in other variations, the GUI may vary in appearance (e.g., layout) while still maintaining the suitable functionalities described herein. For example, as described above, the quick access menu 2520 is displayed in the form of a list near the bottom of the screen, instead of in the form of a ring with icons (as shown in, for example, FIG. 10A). The tool widgets 2532, 2534, and 2536 are displayed on the side bars, instead of overlaid on the endoscopic image (as shown in, for example, FIG. 11A).

Furthermore, FIG. 25 depicts an alternative GUI variation 2500 in which various applications are displayed in sidebar panels located on either side of a main panel display, where at least some of the sidebar panels may be selectively hidden, minimized, made transparent, and/or pinned depending on the user's current preference. For example, in FIG. 25, a control portion 2510*a* of the real-time video application, the timer application 2512, the procedure template application 2514, and/or the image view application 2516, are displayed on sidebar panels of the display. A video feed portion 2510*b* of the real-time video application is displayed in a main panel between the sidebar panels of the display. If a surgeon viewing the GUI 2500 wishes to view an isolated and/or enlarged view of the video feed portion 2510*b* or other content displayed in the main panel (e.g., to reduce distraction), the surgeon may have several options for accomplishing this. As one example, the surgeon may selectively hide a portion (or all) of a sidebar panel, making the sidebar panel appear to be tucked away. Furthermore, in this example, the main panel may be enlarged to occupy at least substantially the entire display (e.g., to avoid visual distractions). As another example, the surgeon may selectively minimize a portion (or all) of a sidebar panel, reducing the visible size of the sidebar panel (e.g., restricting the visible portion to the equivalent of a header or representative icon). As yet another example, the surgeon may adjust transparency of a portion (or all) of a sidebar panel and overlay the transparent sidebar panel over the main panel, thereby allowing the surgeon to view the video feed behind the sidebar panel. Conversely, if the surgeon wishes to reinstate the hidden, minimized, or transparent portion of the sidebar panel, the surgeon may do so by, for example, "hovering" over or clicking on a region of the display corresponding to the typical location of the sidebar panel. For example, while the main panel is isolated and/or enlarged (e.g., to occupy the entire display), other content such as other applications and/or one or more tool kits may appear overlaid on the main panel (e.g., pop up, "flow", etc. over the main panel). As another example, the main panel may be reduced in displayed size to accommodate for the display of one or more sidebar panels. The surgeon may pin the previously hidden, minimized, or transparent portion of the sidebar panel with a clicking gesture using the user input devices and/or other suitable selection process. Other applications not depicted in FIG. 25 may additionally or alternatively populate the sidebar panels. In some variations, applications populating the sidebar panels may be depicted in a minimalistic style (e.g., simple and clean lines, etc.) or other suitable style. Furthermore, it should be understood that aspects of the GUI and exemplary user interaction described with reference to FIG. 25 may be combined with other GUI variations and user interactions described elsewhere herein, in any suitable manner.

Illustrative GUI Variations

As described above, in some variations, the GUI may be displayed on various kinds of displays, such as in a user console, on a team display on a control tower display, on a nurse display (e.g., at a bedside of the patient), etc. In some variations, the GUI may be substantially the same across these various displays, and content in the GUI may be mirrored or repeated on all of the displays in real-time.

However, in some variations, at least some of the displays may be configured to display different variations or versions of the GUI. For example, because some surgeon-specific content of the GUI may be aimed at a surgeon sitting in a user console and controlling the robotic system, not all content of a GUI may necessarily have to be displayed on a team display or nurse display. In such variations, the team display, nurse display, and/or other displays (other than a display at the user console) may display versions of the GUI that omit surgeon-specific content, render certain applications at a larger size to increase visibility, etc. Conversely, one or more of the displays (other than a display at the user console) may display versions of the GUI that display content aimed at non-surgeon staff, such as a nurse, a remote off-site collaborator, etc. In such variations, the user console display may omit content aimed at non-surgeon staff. In some variations, for example, a display (e.g., open display, immersive display, etc.) in a surgeon console, a team display on a control tower, and a bedside nurse display may display different content tailored for their respective primary viewers. For example, the display in a surgeon console may function as the surgeon's primary visual interface for the procedure, the team display may enable surgical staff to follow the procedure (e.g., showing a procedural checklist to prepare for next steps), and the nurse display may be focused on data entry (e.g., relating to tool settings).

Figure 16:
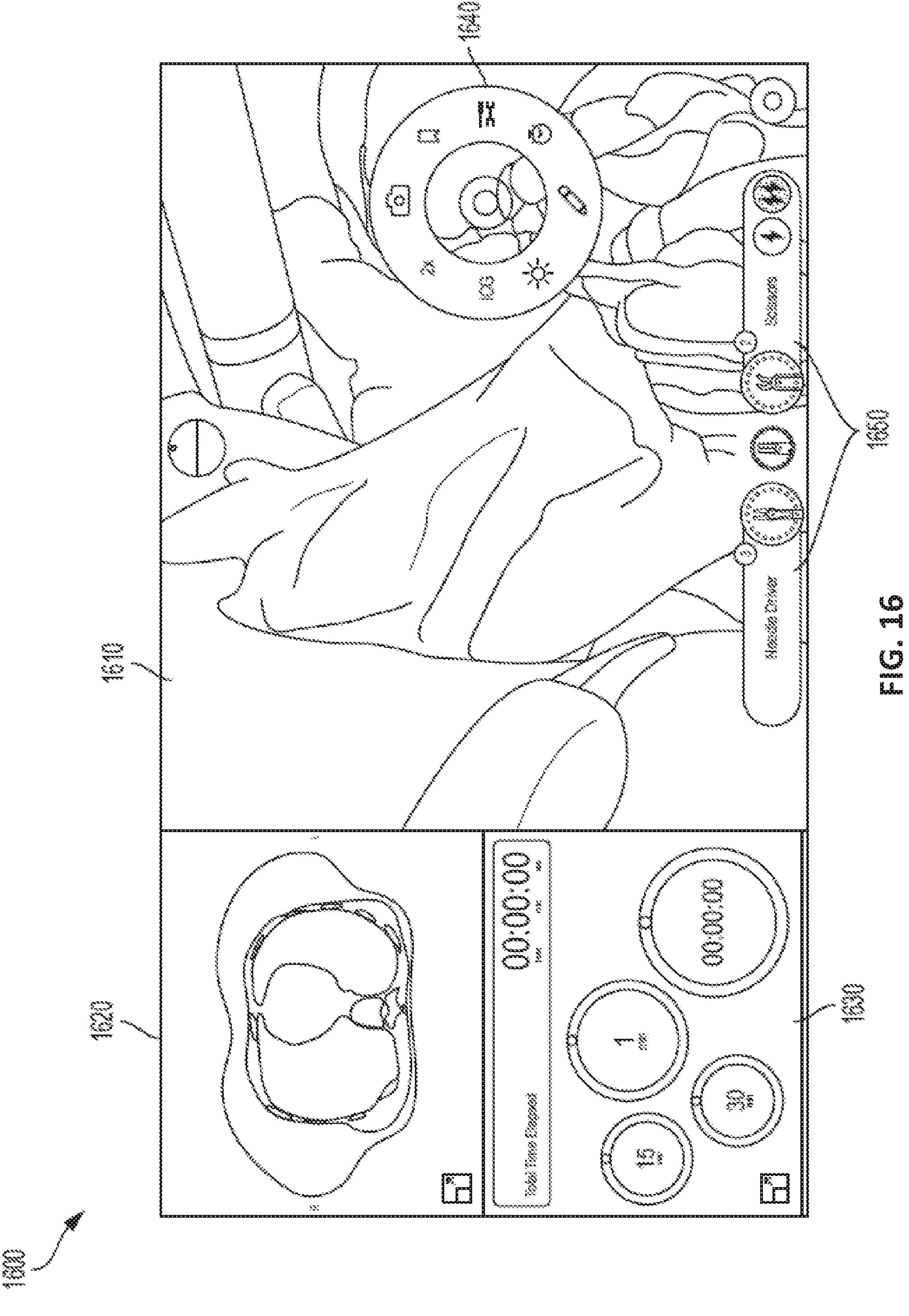
FIGS. 16 and 17 are exemplary variations of a GUI for a team display.
Figure 17:
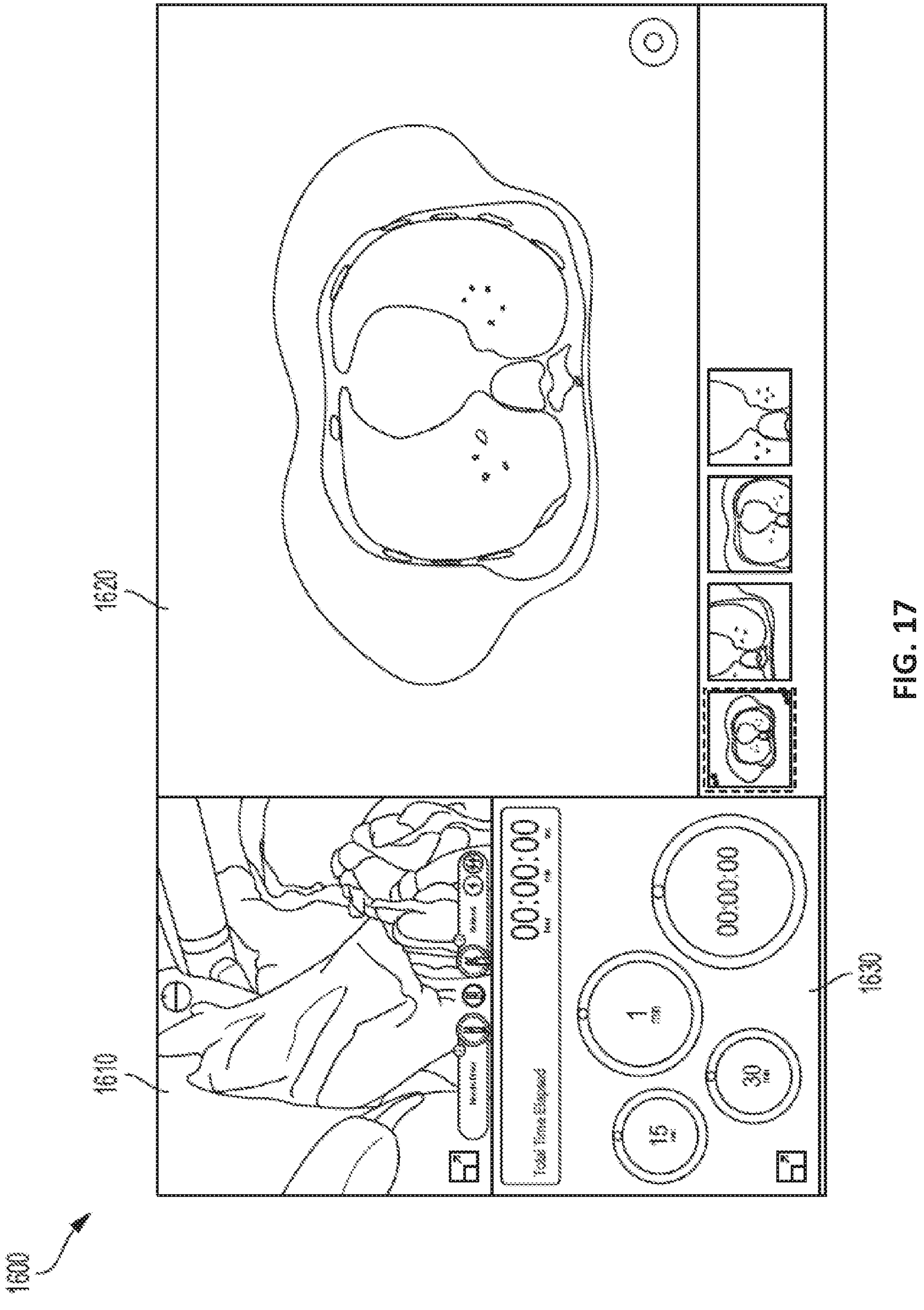

For example, FIGS. 16 and 17 shows an exemplary variation of a GUI 1600 that may be displayed at a team display on top of a control tower for the robotic system, where the team display may be intended to be viewed by a large group of people from varying distances from the display (e.g., next to the display, or across the room from the display). As shown in FIG. 16, exemplary high-priority items for a team display may include an endoscopic image 1610 displayed in a large panel (along with a quick access menu 1640, and tool widgets 1650), content from an image viewer application 1620 rendered in a medium panel, and content from a timer application 1630 rendered in a medium panel. These sources of medical data may, in some variations, be considered particularly important for all members of a surgical team to view during a surgical procedure.

At some point during a surgical procedure, the layout of the team display may dynamically change among the panels of the display. For example, the content may be automatically rearranged (e.g., to mirror rearrangement on a user console display, or based on current progress in the surgical procedure according to a procedure template application, etc.) or rearranged based on user input at the team display. For example, as shown in FIG. 17, an image viewer application 1620 may be swapped with the endoscopic image 1610, such that content from the image viewer application 1620 may be rendered in a large panel, the endoscopic image may be displayed in a medium panel, and content from a timer application 1630 may be rendered in another medium panel. However, it should be understood that the layout of the team display may vary in any suitable manner (e.g., various numbers of panels, various sizes of panels, etc.).

Figure 18:
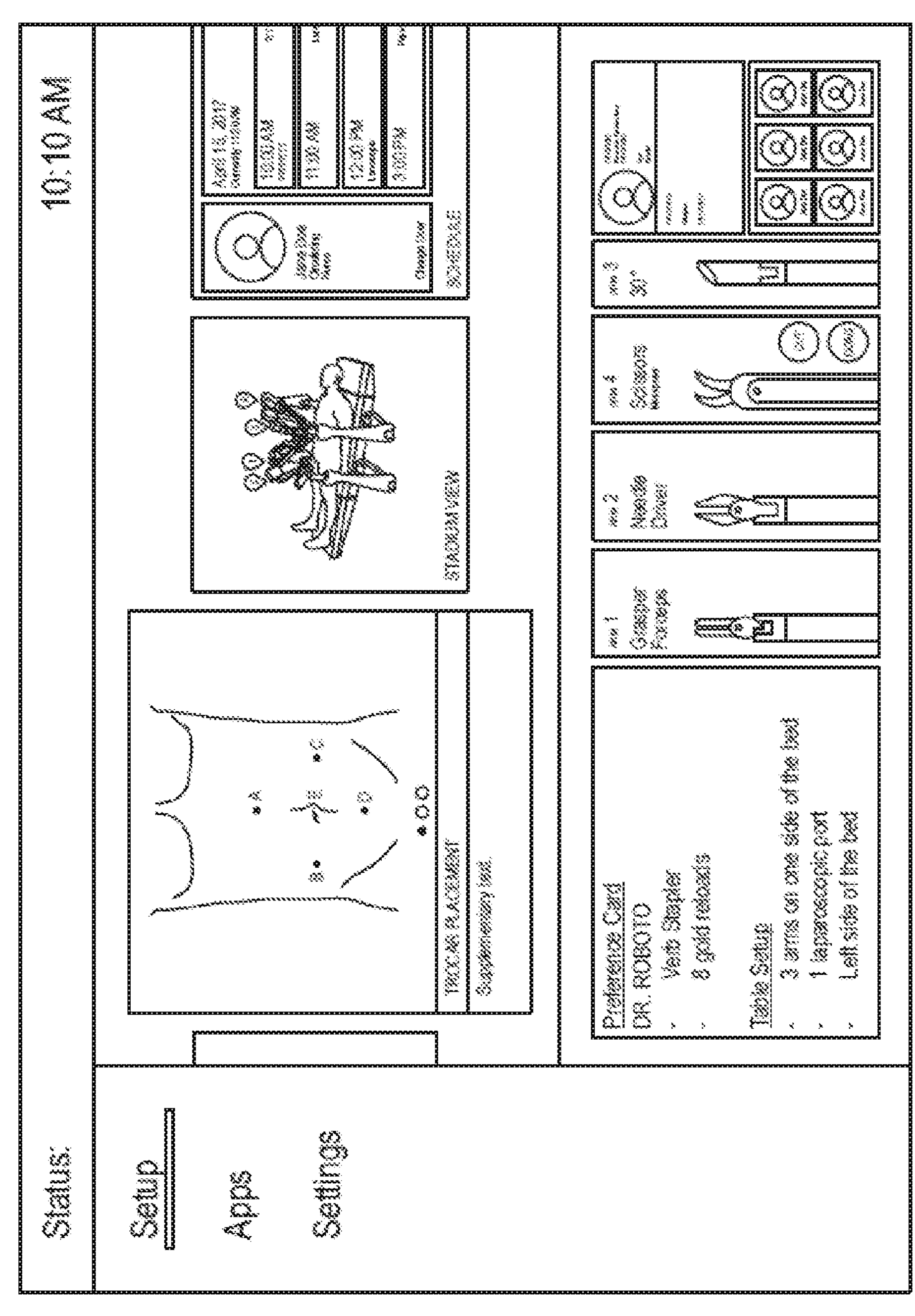
FIGS. 18 and 19 are exemplary variations of a GUI for another display such as for a nurse or other medical staff.

As another example, FIG. 18 shows an exemplary variation of a GUI 1800 that may be displayed at a nurse display, where the nurse display may be intended to be viewed by a nurse or other staff member providing assistance before, during and/or after the surgical procedure. The GUI 1800 may include content primarily targeted for the nurse display, such as information relating to setup pre-operatively (e.g., trocar placement, robotic arm setup on patient table, surgical robotic setup personalized to a particular surgeon) or teardown post-operatively. As another example, the GUI 1800 may include administrative content such as a schedule of upcoming cases for the operating room (and/or for the surgical staff, possibly in other operating rooms). The GUI 1800 may, in some variations, be toggled between other variations of the GUI such as one similar to the team display GUI 1600 described above, such as after setup is complete.

FIG. 19 shows another exemplary variation of at least part of a GUI including a generator application 1900 as described above. For example, a GUI at a nurse display may render a generator application 1900 in a large panel such that a nurse or other staff member may adjust energy settings and other settings of surgical instruments via the generator application 1900.

FIGS. 22 and 23 shows additional exemplary variations of at least part of a GUI including examples of a procedure template application. As shown in FIG. 22, a surgical task checklist 2210 and a surgical instrument list 2220 may be enlarged to fill a large panel of a nurse display or other suitable display. Similarly, as shown in FIG. 23, a schematic diagram of port placement may be enlarged to fill a large panel of a nurse display or other suitable display.

As yet another example, FIG. 24 shows another exemplary variation of at least part of a GUI including a video labeling application 2400. As shown in FIG. 24, the video labeling application may be enlarged to fill a large panel of a nurse display or other suitable display.

GUI Interaction

As described above, the GUI may include one or more interactive graphical objects that may be controlled, selected, or otherwise interacted with by a user. In some variations, a user may interact with the GUI via a user input device such as a touchscreen, mouse, keyboard, etc. or other communication schemes (e.g., voice command, eye tracking, etc.). In variations in which the GUI is displayed on a display in a user console that is used to control a robotic surgical system (e.g., by a surgeon), at least some of the interactive graphical objects may be controlled, selected, or otherwise interacted with via one or more user controls that are also used to control an aspect of the surgical system (e.g., surgical instrument). For example, a user may use one or more handheld user input devices and/or one or more foot pedals to selectively control an aspect of the robotic surgical system and selectively interact with the GUI. By enabling control of both the robotic surgical system and the GUI with the same user controls, the user may advantageously avoid having to switch between two different kinds of user controls. Enabling the user to use the same input devices to control the robotic system and the GUI streamlines the surgical procedure and increases efficiency, as well as helps the user maintain sterility throughout a surgical procedure.

For example, during a surgical procedure, a user may use one or more controls such as at least one handheld user input device or at least one foot pedal. Exemplary variations of controls for a robotic surgical system are described in further detail in U.S. Patent Application Ser. No. 62/432,528 titled "USER INTERFACE DEVICES FOR USE IN ROBOTIC SURGERY" filed Dec. 9, 2016, and U.S. patent application Ser. No. 15/476,454 titled "MULTI-FUNCTIONAL FOOT PEDAL ASSEMBLY FOR CONTROLLING A ROBOTIC SURGICAL SYSTEM" filed Mar. 31, 2017, each of which is incorporated herein in its entirety by this reference.

Figures 20A, 20B:
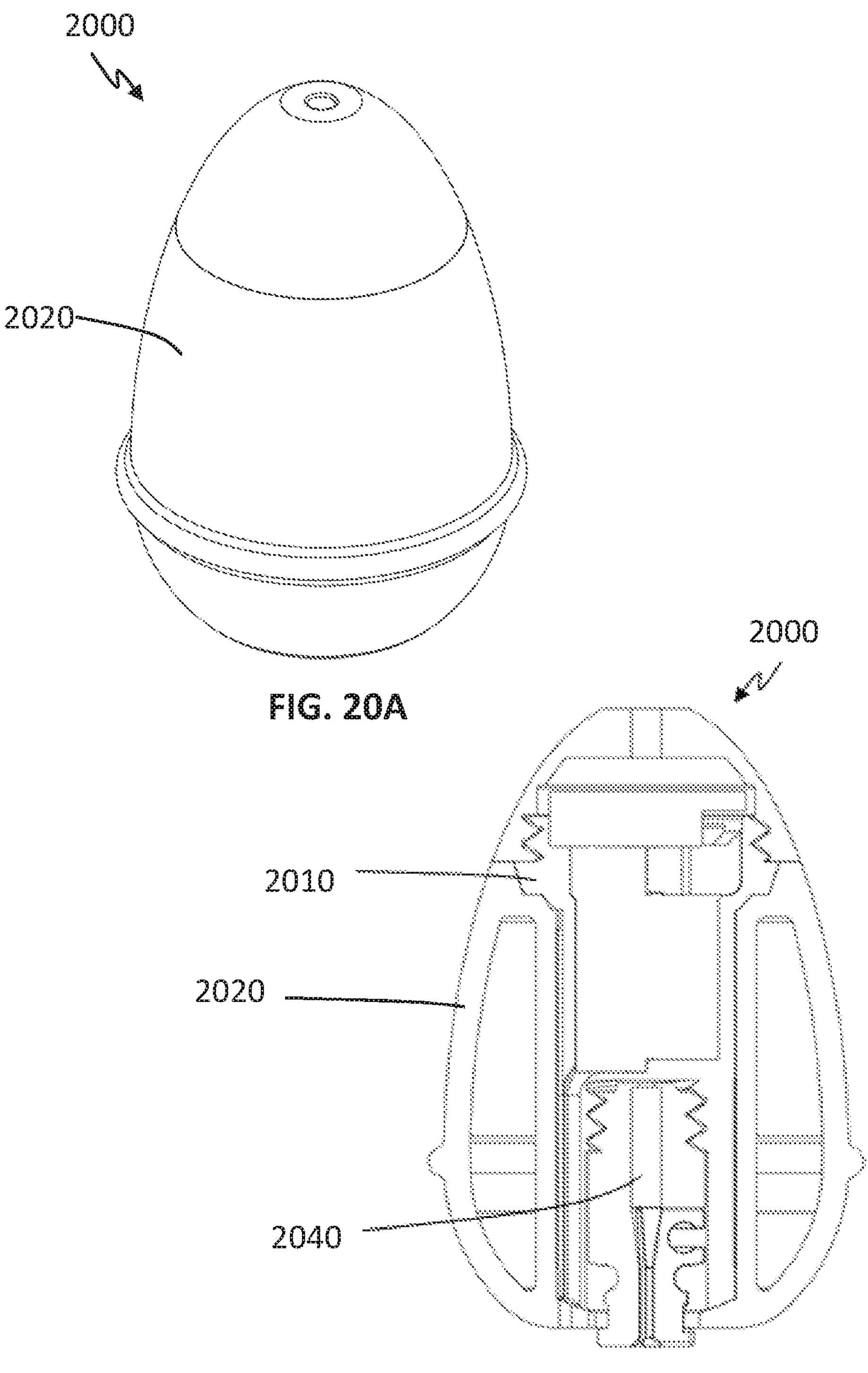
FIGS. 20A and 20B are perspective and longitudinal cross-sectional views, respectively, of one exemplary variation of a handheld user input device.

As shown generally in FIGS. 20A and 20B, an exemplary variation of a handheld user input device 2000 for controlling a robotic system may include a member 2010, a housing 2020 at least partially disposed around the member and configured to be held in the hand of a user, and a tracking sensor system 2040 configured to detect at least position and/or orientation of at least a portion of the device. The housing 2020 may be flexible (e.g., made of silicone). In some instances, the detected position and/or orientation of the device may be correlatable to a control of the robotic system. For example, the user input device 2000 may control at least a portion of a robotic arm, an end effector or tool (e.g., graspers or jaws) coupled to a distal end of the robotic arm, a GUI, or other suitable aspect or feature of a robotic surgical system. Additionally, in some instances, the detected position and/or orientation of the device may be correlatable to a control of a GUI. Furthermore, in some variations, the user input device 2000 may include one or more sensors for detecting other manipulations of the user input device 2000, such as squeezing of the housing 2020 (e.g., via one or more pressure sensors, one or more capacitive sensors, etc.).

Generally, a user interface for controlling a robotic surgical system may include at least one handheld user input device 2000, or may include at least two handheld user input devices 2000 (e.g., a first user input device to be held by a left hand of the user, and a second user input device to be held by a right hand of the user), or any suitable number. Each user input device 2000 may be configured to control one or more different aspects or features of the robotic system. For example, a user input device held in the left hand of the user may be configured to control an end effector represented on a left side of a camera view provided to the user, while a user input device held in the right hand of the user may be configured to control an end effector represented on a right side of the camera view. As another example, a user input device 2000 may "clutch" between different modes for controlling different aspects or features of the robotic system, such as that described below.

In some variations, the handheld user input device 2000 may be a groundless user input device configured to be held in the hand and manipulated in free space. For example, the user input device 2000 may be configured to be held between the fingers of a user, and moved about freely (e.g., translated, rotated, tilted, etc.) by the user as the user moves his or her arms, hands, and/or fingers. Additionally or alternatively, the handheld user input device 2000 may be a body-grounded user input device, in that the user input device 2000 may be coupled to a portion of the user (e.g., to fingers, hand, and/or arms of a user) directly or via any suitable mechanism such as a glove, hand strap, sleeve, etc. Such a body-grounded user input device may still enable the user to manipulate the user input device in free space. Accordingly, in variations in which the user input device 2000 is groundless or body-grounded (as opposed to permanently mounted or grounded to a fixed console or the like), the user input device 2000 may be ergonomic and provide dexterous control, such as by enabling the user to control the user input device with natural body movements unencumbered by the fixed nature of a grounded system.

The handheld user input device 2000 may include wired connections that, for example, may provide power to the user input device 2000, carry sensor signals (e.g., from the tracking sensor assembly and/or other sensors such as a capacitive sensor, optical sensor, etc. Alternatively, the user input device may be wireless as shown in FIG. 20A and communicate commands and other signals via wireless communication such as radiofrequency signals (e.g., WiFi or short-range such as 400-500 mm range, etc.) or other suitable wireless communication protocol such as Bluetooth. Other wireless connections may be facilitated with optical reader sensors and/or cameras configured to detect optical markers on the user input device 2000 infrared sensors, ultrasound sensors, or other suitable sensors.

The handheld user input device may include a clutch mechanism for switching between controlling a robotic arm or end effector and controlling a graphical user interface, etc., and/or between other control modes. One or more of the various user inputs described in further detail below may, in any suitable combination, function as a clutch. For example, touching a gesture touch region of the device, squeezing the housing, flicking or rotating the user input device, etc. may function to engage a clutch. As another example, a combination of squeezing and holding the user input device, and rotating the user input device, may function as a clutch. However, any suitable combination of gestures may function as a clutch. Additionally or alternatively, user input to other user input devices (e.g., foot pedal assembly) may, alone or in combination with user input to a handheld user input device, function as a clutch.

In some variations, engagement and disengagement of a clutch mechanism may enable transition between use of a handheld user input device as a control for the robotic system and use of the handheld user input device as a control for the GUI (e.g., to operate a cursor displayed on the screen). When a clutch mechanism is engaged such that the user input devices are used to control the GUI, positions or poses of the robotic arms may be substantially locked in place to "pause" operation of the robotic system, such that subsequent movement of the user input devices while the clutch is engaged will not inadvertently cause movement of the robotic arms.

As shown in FIG. 21A, a left-hand user input device and a right-hand user input device may provide control of a left-hand cursor icon 2100L and a right-hand cursor icon 2100R, respectively. The cursor icons may, in some variations, be stylized graphical representations of the handheld user input devices. For example, the exemplary user input devices 2000 may be generally egg-shaped as shown in FIG. 20A. Accordingly, they may be used to operate a cursor that is generally egg-shaped as shown in FIG. 21A, with additional points indicating directionality and/or handedness of the cursor icons. The cursor icons may, in some variations, move along an X-Y plane within a display of the GUI, and may overlap each other on the screen.

When the user input device is used as a control for the GUI, its detected changes in position and/or orientation of the device may be correlatable to one or more actions for interacting the GUI. For example, FIG. 21B illustrates exemplary control schemes correlating movements of a handheld user input device with actions suitable for control of the GUI. For example, orthogonal flicks (e.g., a directional point that is brief in duration, followed by a return to a center point) in left, right, downward, and upward directions may indicate left, right, down, and up GUI actions, such as for scrolling. As another example, a twist of a user input device, such as around a central axis of the device, may be used to adjust GUI items such as virtual sliders and virtual knobs.

In some variations, flicks may be effectively constrained in one or more directions, such as for scrolling purposes within a GUI. For example, only horizontal directional components of movement of a user input device may be used for correlation to control of a GUI, while vertical directional components may be ignored. Alternatively, only vertical directional components of movement of a user input device may be used for correlation to control of a GUI, while horizontal directional components are ignored.

Additionally or alternatively, a squeeze input may be interpreted in one or more manners as control input for a GUI. For example, as shown in FIG. 21B, a single squeeze of the housing of the user input device may be correlated to a selection operation (e.g., akin to "enter" on a keyboard). A double squeeze in rapid succession may be correlated to a "go back" or "undo" operation. As another example, a squeeze and holding of the user input device for an extended period of time (e.g., 3 seconds) may be used as a specialized operation, such as to clutch "out" of the GUI and return to using the user input devices to control the robotic system.

Furthermore, relative position and/or orientation of a left-hand user input device and a right-hand user input device may be correlated to additional kinds of control of the GUI. For example, a user may use both devices to manipulate 3D objects (e.g., in rotation), or zoom in and out of a displayed image (e.g., by moving the devices closer together to zoom out, and moving the devices farther apart to zoom in). Additionally or alternatively, the relative position and/or orientation of the devices to each other may be correlated to control of the GUI in any suitable manner.

The foregoing description, for purposes of explanation, used specific nomenclature to provide a thorough understanding of the invention. However, it will be apparent to one skilled in the art that specific details are not required in order to practice the invention. Thus, the foregoing descriptions of specific embodiments of the invention are presented for purposes of illustration and description. They are not intended to be exhaustive or to limit the invention to the precise forms disclosed; obviously, many modifications and variations are possible in view of the above teachings. The embodiments were chosen and described in order to best explain the principles of the invention and its practical applications, they thereby enable others skilled in the art to best utilize the invention and various embodiments with various modifications as are suited to the particular use contemplated. It is intended that the following claims and their equivalents define the scope of the invention.

The invention claimed is:

1. A robotic surgical system, comprising:

a robotic arm with an end effector;

an input device configured to control movement of the robotic arm with the end effector while a housing of the input device is in a hand of a user and while the robotic surgical system is in teleoperation;

an endoscopic camera configured to capture one or more endoscopic images of a surgical site during a surgical procedure that is performed while the robotic surgical system is in teleoperation;

a display configured to display a graphical user interface (GUI);

at least one processor; and memory having instructions which when executed by the at least one processor causes the robotic surgical system to:

display the one or more endoscopic images in the GUI on the display;

determine whether a surgical task of the surgical procedure has been completed based on the one or more endoscopic images;

responsive to a determination that the surgical task is complete, switch the input device from controlling the movement of the robotic arm to controlling a user interface (UI) item in the GUI displayed on the display; and receive, via the input device, an input to control the UI item, wherein the input includes a rotational movement of the housing of the input device that is received about a same axis as the end effector.

2. The robotic surgical system of claim 1, wherein the rotational movement is received about the same axis as the end effector such that the input device remains aligned with the end effector while the input device controls the UI item.

3. The robotic surgical system of claim 1, wherein the input is a first input, wherein the memory has further instructions to receive, via the input device, a second input that is different than the first input, wherein the switching of the input device from controlling the movement to controlling the UI item occurs and is maintained while the second input is received via the input device.

4. The robotic surgical system of claim 3, wherein the input device comprises a clutch mechanism, wherein the memory has further instructions to pause robotic arm movement while the second input is received via the clutch mechanism of the input device.

5. The robotic surgical system of claim 1, wherein the UI item comprises a menu with a plurality of selectable items that are arranged in a ring, wherein the rotational movement of the housing allows the user to navigate through the plurality of selectable items.

6. The robotic surgical system of claim 1, wherein the GUI includes a display panel that includes the one or more endoscopic images of the surgical site captured by the endoscopic camera during the surgical procedure, wherein the GUI further includes a floating UI item at an edge of the display panel that indicates that a surgical instrument is out of a field of view of the endoscopic camera and is at a location of the surgical site based on the edge at which the floating UI item is located.

7. The robotic surgical system of claim 6, wherein the floating UI item comprises a line that indicates an orientation of the endoscopic camera.

8. The robotic surgical system of claim 1, wherein the one or more endoscopic images of the surgical site includes a surgical instrument, and a floating UI item overlaid on top of the one or more endoscopic images, wherein the memory has further instructions to:

determine, based on the one or more endoscopic images, that the surgical instrument is moving within a field of view of the endoscopic camera; and move the floating UI item to mirror the movement of the surgical instrument such that the floating UI item maintains a distance from the surgical instrument in the one or more endoscopic images.

9. The robotic surgical system of claim 1, wherein the one or more endoscopic images are displayed in a primary panel in the GUI, wherein the memory has further instructions to switch the one or more endoscopic images with visual content of a software application that is displayed in a secondary panel in the GUI such that the visual content is displayed in the primary panel and the one or more endoscopic images are displayed in the secondary panel, responsive to determining that the surgical task is complete.

10. The robotic surgical system of claim 1, wherein the instructions to determine that the surgical task is complete includes instructions to perform a machine vision algorithm upon the one or more endoscopic images that includes the surgical site to identify completion of the surgical task.

11. A method performed by a robotic surgical system that includes a robotic arm with an end effector and a display, the method comprising:

displaying, in a graphical user interface (GUI) in the display, one or more endoscopic images captured by an endoscopic camera during a surgical procedure that is performed while the robotic surgical system is in teleoperation, wherein the one or more endoscopic images comprises a surgical site;

determining whether a surgical task of the surgical procedure has been completed based on the one or more endoscopic images;

responsive to determining that the surgical task is complete, switching an input device from controlling movement of the robotic arm to controlling a user interface (UI) item in the GUI displayed on the display; and receiving, via the input device, an input to control the UI item, wherein the input includes a rotational movement of the input device that is received about a same axis as the end effector.

12. The method of claim 11, wherein the rotational movement is received about the same axis as the end effector such that the input device remains aligned with the end effector while the input device controls the UI item.

13. The method of claim 11, wherein the input is a first input, wherein the method further comprises receiving, via the input device, a second input that is different than the first input, wherein the switching of the input device from controlling the movement to controlling the UI item occurs and is maintained while the second input is received via the input device.

14. The method of claim 13, wherein the input device comprises a clutch mechanism, wherein the method further comprises pausing robotic arm movement while the second input is received via the clutch mechanism of the input device.

15. The method of claim 11, wherein the UI item comprises a menu with a plurality of selectable items that are arranged in a ring, wherein the rotational movement of the input device allows a user of the input device to navigate through the plurality of selectable items.

16. The method of claim 11, wherein the GUI includes a display panel that includes the one or more endoscopic images of the surgical site captured by the endoscopic camera during the surgical procedure, wherein the GUI further includes a floating UI item at an edge of the display panel that indicates that a surgical instrument is out of a field of view of the endoscopic camera and is at a location of the surgical site based on the edge at which the floating UI item is located.

17. The method of claim 16, wherein the floating UI item comprises a line that indicates an orientation of the endoscopic camera.

18. The method of claim 11, wherein the one or more endoscopic images of the surgical site includes a surgical instrument, and a floating UI item overlaid on top of the one or more endoscopic images, wherein the method further comprises:

determining, based on the one or more endoscopic images, that the surgical instrument is moving within a field of view of the endoscopic camera; and moving the floating UI item to mirror the movement of the surgical instrument such that the floating UI item maintains a distance from the surgical instrument in the one or more endoscopic images.

19. The method of claim 11, wherein the one or more endoscopic images are displayed in a primary panel in the GUI, wherein the method further comprises switching the one or more endoscopic images with visual content of a software application that is displayed in a secondary panel in the GUI such that the visual content is displayed in the primary panel and the one or more endoscopic images are displayed in the secondary panel, responsive to determining that the surgical task is complete.

20. The method of claim 11, wherein determining that the surgical task is complete comprises performing a machine vision algorithm upon the one or more endoscopic images that includes the surgical site to identify completion of the surgical task.

* * * * *